(12) United States Patent
Callen et al.

(10) Patent No.: US 7,273,740 B2
(45) Date of Patent: Sep. 25, 2007

(54) ENZYMES HAVING ALPHA AMYLASE ACTIVITY AND METHODS OF USE THEREOF

(75) Inventors: Walter Callen, San Diego, CA (US); Toby Richardson, San Diego, CA (US); Gerhard Frey, San Diego, CA (US); Carl Miller, Raleigh, NC (US); Martin Kazaoka, San Diego, CA (US); Jay M. Short, Rancho Santa Fe, CA (US); Eric Mathur, Carlsbad, CA (US)

(73) Assignee: Verenium Corporation, San Diego, CA (US)

( * ) Notice: Subject to any disclaimer, the term of this patent is extended or adjusted under 35 U.S.C. 154(b) by 681 days.

(21) Appl. No.: 10/081,739

(22) Filed: Feb. 21, 2002

(65) Prior Publication Data

US 2003/0170634 A1   Sep. 11, 2003

Related U.S. Application Data

(60) Provisional application No. 60/270,495, filed on Feb. 21, 2001, provisional application No. 60/270,496, filed on Feb. 21, 2001, provisional application No. 60/291,122, filed on May 14, 2001.

(51) Int. Cl.
| | |
|---|---|
| *C12N 9/26* | (2006.01) |
| *C07H 21/04* | (2006.01) |
| *C12P 21/06* | (2006.01) |
| *C12P 19/34* | (2006.01) |

(52) U.S. Cl. .............................. 435/201; 435/4; 435/6; 435/69.1; 435/183; 435/200; 435/41; 435/91.1; 435/440; 536/23.2; 536/23.4; 536/23.5; 536/23.7; 536/24.31

(58) Field of Classification Search .................... 435/4, 435/6, 69.1, 183, 200, 252.34, 320.1; 536/23–24
See application file for complete search history.

(56) References Cited

FOREIGN PATENT DOCUMENTS

| EP | 0648843 | 4/1995 |
|---|---|---|
| FR | 2778412 | 11/1999 |
| WO | WO97/44361 | 11/1997 |
| WO | WO98/45417 | 10/1998 |

OTHER PUBLICATIONS

Imanaka et al. (Gen Bank Acc No. E13334, Apr. 27, 1998).*

Database GenBank, US National Library of Medicine (Bethesda, MD, USA) No. AF068225, Leveque et al., May 2000.
Database GenBank, US National Library of Medicine, (Bethesda, MD, USA) No. D83793, Tachibana, et al., Feb. 2000.
Database GenBank, US National Library of Medicine (Bethesda, MD, USA) No. E13334, Imanaka, et al., Jun. 1998.
Database GenBank, US National Library of Medicine (Bethesda, MD, USA) No. AAW34998, Lam, et al., May 1998.
Database GenBank, US National Library of Medicine (Bethesda, MD, USA) No. AAW26131, Imanaka, et al., Nov. 1997.
Database GenBank, US National Library of Medicine (Bethesda, MD, USA) No. AAY53917, Leveque, et al., Mar. 2000.
Database GenBank, US National Library of Medicine (Bethesda, MD, USA) No. AAR72603, Asada, et al., Oct. 1995.
Database GenBank, US National Library of medicine (Bethesda, MD, USA) No. AAR72602, Asada, et al., Oct. 1995.
Database GenBank, US National Library of Medicine, (Bethesda, MD, USA) No. AAW70536, Dong, et al., Jan. 1999.
Dong et al., Applied and Environmental Microbiology 63(9):3569-3576 (1997).
Jorgensen et al., Journal of Biological Chemistry 272(26):16335-16342 (1997).
Leveque et al., FEMS Microbiology Letters 186(1):67-71 (2000).
Patent Abstracts of Japan vol. 1997, No. 11, JP 9173077 A (Jul. 8, 1997).
Supplementary European Search Report mailed on Sep. 6, 2004 for European patent application No. EP 02706401, 5 pages.
Tachibana et al., Journal of Fermentation and Bioengineering 82(3):224-232 (1996).
Bork, P. (2000). Genome Research 10:348-400.
Broun et al. (1998). Science 282:1315-1317.
Fox et al. (1991). Anal. Biochem. 195(1):93-96.
Seffernick et al. (2001). J. of Bacteriol. 183(8):2405-2410.
Van de Loo et al. (1995). Proc. Natl. Acad. Sci. 92(15):6743-6747.
Witkowski et al. (1999). Biochemistry 38:11643-11650.
Wong et al. (2000). J. Agric. Food Chem., 48(10):4540-4543.
Database Uniprot 'Online! (2000). Alpha amylase-pyrococcus woesei, XP002317659 retrieved from EBI, Database Accession No. Q9P9LO.
Jones et al. (1999). Journal of Applied Microbiology 86(1):93-107 XP002317658.
Supplementary Partial European Search Report mailed on Mar. 11, 2005, for European Patent application No. 02723192.7, based on PCT/US02/05068 filed on Feb. 21, 2002.
Guo et al., PNAS USA (2004) 101(25):9205-9210.

\* cited by examiner

*Primary Examiner*—Manjunath Rao
(74) *Attorney, Agent, or Firm*—Morrison & Foerster LLP

(57) ABSTRACT

The invention relates to alpha amylases and to polynucleotides encoding the alpha amylases. In addition methods of designing new alpha amylases and methods of use thereof are also provided. The alpha amylases have increased activity and stability at increased pH and temperature.

38 Claims, 14 Drawing Sheets

Figure 5: Example Standard Curve of the assay of Example 2.
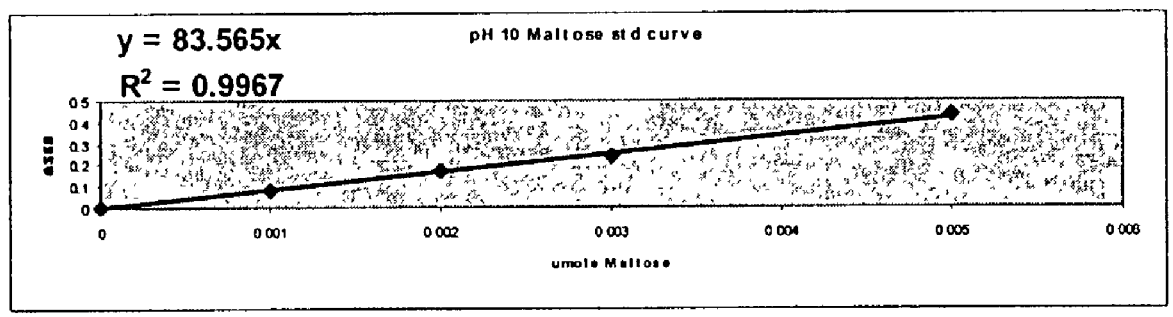

Figure 7:

SEQ ID NO:1
atggccaagtactccgagctggaaaagggcggggtcataatgcaggcgttctactgggacgtgccttcaggaggaatatggtgggacacaat
acggcagaagataccggagtggtacgatgccggaatctccgcaatatggattccccggcgagcaagggcatgggcggcgccattcgatg
ggctacgacccctacgacttctttgacctcggtgagtacgaccagaagggaacggtagagacgcgctttggctccaagcaggagctcgtgaa
catgataaacaccgcccacgcctatggcatgaaggtaatagccgatatagtcatcaaccaccgcgccggcggtgacctggagtggaaccoctt
cgtgaacgactatacctggaccgacttctcaaaggtcgcgtcgggtaaatacacggccaactacctcgacttccacccgaacgagctccatgc
gggcgattccggaacatttggaggctatcccgacatatgccacgacaagagctgggaccagtactggctctgggccagccaggagagctac
gcggcatatctcaggagcatcggcatcgatgcctggcgcttcgactacgtcaagggctatgctccctgggtcgtcaaggactggctgaactggt
ggggaggctgggcggttggagagtactgggacaccaacgtcgacgctgttctcaactgggcatactcgagcggtgccaaggtctttgacttcg
ccctctactacaagatggatgaggcctttgacaacaaaaacattccagcgctcgtctctgcccttcagaacggccagactgttgtctcccgcgac
ccgttcaaggccgtaacctttgtagcaaaccacgacaccgatataatctggaacaagtatccagcctacgcgttcatcctcacctacgagggcc
agccgacaatattctaccgcgactacgaggagtggctcaacaaggataagctcaagaacctcatctggatacatgagaacctcgccggagga
agcaccgacatagtctactacgataacgatgaactcatcttcgtcaggaacggctacggggacaagccggggcttataacctacatcaacctag
gctcgagcaaggccggaaggtgggtttatgtgccgaagttcgcgggcgcgtgcatccacgagtatactggtaacctcggaggctgggtagac
aagtacgtctactcaagcggctgggtctatctcgaagctccagcttacgaccctgccaacgggcagtatggctactccgtgtggagctactgcg
gggtgggctga SEQ ID NO:2
Met Ala Lys Tyr Ser Glu Leu Glu Lys Gly Gly Val Ile Met Gln Ala Phe Tyr Trp Asp Val Pro Ser
Gly Gly Ile Trp Trp Asp Thr Ile Arg Gln Lys Ile Pro Glu Trp Tyr Asp Ala Gly Ile Ser Ala Ile Trp
Ile Pro Pro Ala Ser Lys Gly Met Gly Gly Ala Tyr Ser Met Gly Tyr Asp Pro Tyr Asp Phe Phe Asp
Leu Gly Glu Tyr Asp Gln Lys Gly Thr Val Glu Thr Arg Phe Gly Ser Lys Gln Glu Leu Val Asn
Met Ile Asn Thr Ala His Ala Tyr Gly Met Lys Val Ile Ala Asp Ile Val Ile Asn His Arg Ala Gly Gly
Asp Leu Glu Trp Asn Pro Phe Val Asn Asp Tyr Thr Trp Thr Asp Phe Ser Lys Val Ala Ser Gly Lys
Tyr Thr Ala Asn Tyr Leu Asp Phe His Pro Asn Glu Leu His Ala Gly Asp Ser Gly Thr Phe Gly Gly
Tyr Pro Asp Ile Cys His Asp Lys Ser Trp Asp Gln Tyr Trp Leu Trp Ala Ser Gln Glu Ser Tyr Ala
Ala Tyr Leu Arg Ser Ile Gly Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr Trp Asp Thr Asn Val Asp Ala
Val Leu Asn Trp Ala Tyr Ser Ser Gly Ala Lys Val Phe Asp Phe Ala Leu Tyr Tyr Lys Met Asp Glu
Ala Phe Asp Asn Lys Asn Ile Pro Ala Leu Val Ser Ala Leu Gln Asn Gly Gln Thr Val Val Ser Arg
Asp Pro Phe Lys Ala Val Thr Phe Val Ala Asn His Asp Thr Asp Ile Ile Trp Asn Lys Tyr Pro Ala
Tyr Ala Phe Ile Leu Thr Tyr Glu Gly Gln Pro Thr Ile Phe Tyr Arg Asp Tyr Glu Glu Trp Leu Asn
Lys Asp Lys Leu Lys Asn Leu Ile Trp Ile His Glu Asn Leu Ala Gly Gly Ser Thr Asp Ile Val Tyr
Tyr Asp Asn Asp Glu Leu Ile Phe Val Arg Asn Gly Tyr Gly Asp Lys Pro Gly Leu Ile Thr Tyr Ile
Asn Leu Gly Ser Ser Lys Ala Gly Arg Trp Val Tyr Val Pro Lys Phe Ala Gly Ala Cys Ile His Glu
Tyr Thr Gly Asn Leu Gly Gly Trp Val Asp Lys Tyr Val Tyr Ser Ser Gly Trp Val Tyr Leu Glu Ala
Pro Ala Tyr Asp Pro Ala Asn Gly Gln Tyr Gly Tyr Ser Val Trp Ser Tyr Cys Gly Val Gly SEQ ID NO: 3
atgttcctgctcgcgttttgctcactgcctcgctgttctgcccaacaggacagcccgccaaggctgccgcaccgtttaacggcaccatgatgca
gtattttgaatggtacttgccggatgatggcacgttatggaccaaagtggccaatgaagccaacaacttatccagccttggcatcaccgctctttg
gctgccgcccgcttacaaaggaacaagccgcagcgacgtagggtacggagtatacgacttgtatgacctcggcgaattcaatcaaaaaggga
ccgtccgcacaaaatacggaacaaaagctcaatatcttcaagccattcaagccgcccacgccgctggaatgcaagtgtacgccgatgtcgtgtt
cgaccataaaggcggcgctgacggcacggaatgggtggacgccgtcgaagtcaatccgtccgaccgcaaccaagaaatctcgggcacctat
caaatccaagcatggacgaaatttgattttcccggcgggggcaacacctactccagcttaagtggcgctggtaccattttgacggcgttgattgg
gacgaaagccgaaaattgagccgcatttacaaattccgcggcatcggcaaagcgtgggattgggaagtagacacggaaaacggaaactatg
actacttaatgtatgccgaccttgatatggatcatcccgaagtcgtgaccgagctgaaaaactggggaaatggtatgtcaacacaacgaacatt
gatgggttccggcttgatgccgtcaagcatattaagttcagtttttttcctgattggttgtcgtatgtgcgttctcagactggcaagccgctatttaccg
tcggggaatattggagctatgacatcaacaagttgcacaattacattacgaaaacagacggaacgatgtctttgtttgatgccccgttacacaaca aattttataccgcttccaaatcaggggcgcatttgatatgcgcacgttaatgaccaatactctcatgaaagatcaaccgacattggccgtcaccttcgttgataatcatgacaccgaacccggccaagcgctgcagtcatgggtcgacccatggttcaaaccgttggcttacgcctttattctaactcggcaggaaggatacccgtgcgtcttttatggtgactattatggcattccacaatataacattccttcgctgaaaagcaaaatcgatccgctcctcatcgcgcgcagggattatgcttacggaacgcaacatgattatcttgatcactccgacatcatcgggtggacaagggaaggggtcactgaaaaaccaggatccgggctggccgcactgatcaccgatgggccgggaggaagcaaatggatgtactgttggcaaacaacacgctggaaaagtgttctatga SEQ ID NO: 4
atgaaacaacaaaaacggctttacgcccgattgctgacgctgttatttgcgctcatcttcttgctgcctcattctgcagcagcggcggcaaatcttaatgggacgctgatgcagtattttgaatggtacatgcccaatgacggccaacattggaagcgcttgcaaaacgactcggcatatttggctgaacacggtattactgccgtctggattccccggcatataagggaacgagccaagcggatgtgggctacggtgcttacgacctttatgatttaggggagtttcatcaaaaagggacggttcggacaaagtacggcacaaaggagagctgcaatctgcgatcaaaagtcttcattcccgcgacattaacgtttacggggatgtggtcatcaaccacaaaggcggcgctgatgcgaccgaagatgtaaccgcggttgaagtcgatcccgctgaccgcaaccgcgtaattcaggagaacaccgaattaaagcctggacacattttcattttccggggcgcggcagcacatacagcgattttaaatggcattggtaccattttgacggaaccgattgggacgagtcccgaaagctgaaccgcatctataagtttcaaggaaaggcttgggattgggaagtttccaatgaaaacggcaactatgattatttgatgtatgccgacatcgattatgaccatcctgatgtcgcagcagaaattaagagatggggcacttggtatgccaatgaactgcaattggacggttccgtcttgatgctgtcaaacacattaaattttcttttttgcgggattgggttaatcatgtcagggaaaaaacggggaaggaaatgtttacggtagctgaatattggcagaatgacttggcgcgctggaaaactatttgaacaaaacaaattttaatcattcagtgtttgacgtgccgcttcattatcagttccatgctgcatcgacacagggaggcggctatgatatgaggaaattgctgaacggtacggtcgtttccaagcatccgttgaaagcggtacatttgtcgataaccatgatacacagccggggcaatcgcttgagtcgactgtccaaacatggtttaagccgcttgcttacgctttcattctcacaagggaatctggatacccctcaggttttctacggggatatgtacgggacgaaaggagactcccagcgcgaaattcctgccttgaaacacaaaattgaaccgatcttaaaagcgagaaaacagtatgcgtacggagcacagcatgattatttcgaccaccatgacattgtcggctggacaagggaaggcgacagctcggttgcaaattcaggtttggcggcattaataacagacggacccggtggggcaaagcgaatgtatgtcggccggcaaaacgccggtgagacatggcatgacattaccggaaaccgttcggagccggttgtcatcaattcggaaggctggggagagtttcacgtaaacggcgggtcggtttcaatttatgttcaaagatag SEQ ID NO: 5
gtggtgcacatgaagttgaagtaccttgccttagttttgttggctgtggcttcgataggcctactctcgactccagtgggtgctgccaagtactccgaactcgaagagggcggtgttataatgcaggccttctactgggatgttcccggaggggggaatctggtgggacaccataagacagaaaatcccggagtggtacgacgctggaatctcggcgatatggattcctccagctagcaaaggatgggcggtggttattccatgggctacgatccctacgatttcttttgacctcggcgagtactatcagaagggaacagttgagacgcgcttcggctcaaaggaggaactggtgaacatgataaacaccgcacactcctatggcataaaggtgatagcggacatagtcataaaccaccgcgccggtggagaccttgagtggaacccctttgtaaacaactatacttggacagacttctccaaggtcgcctccggtaaatacacggccaactaccttgacttccacccaaacgaggtcaagtgctgcgatgagggtacatttggtgacttttccggacatcgcccacgagaagagctgggatcagtactggctctgggcaagcaatgagagctacgccgcatatctccggagcataggatcgatgcatggcgtttcgactacgtcaaaggttacggagcgtgggttgttaatgactggctcagctggtggggaggctgggccgttggagagtactgggacacgaacgttgatgcactccttaactgggcatacgacagcggtgccaaggtctttgacttccgctctactacaagatggacgaagcctttgacaacaccaacatcccgcttggtttacgccctccagaacggaggaacagtcgtttcccgcgatcccttcaaggcagtaactttcgttgccaaccacgatacagatataatctggaacaagtatccggcttatgcgttcatccttacctatgagggacagcctgttatattttaccgcgactacgaggagtggctcaacaaggataagcttaacaaccttatctggatacacgagcaccttgccggaggaagtaccaagatcctctactacgataacgatgagctaatattcatgagggagggctacgggagcaagccgggcctcataacctacataaacctcggaaacgactgggccgagcgctgggtgaacgtcggctcaaagtttgccggctacacaatccatgaatacacaggcaatctcggtggctgggttgacaggtgggttcagtacgatggatgggttaaactgacggcacctcctcatgatccagccaacggatattacggctactcagtctggagctacgcaggcgtcggatga SEQ ID NO.: 6
atgaagaagtttgtcgccctgttcataaccatgtttttcgtagtgagcatggcagtcgttgcacagccagctagcgccgcaaagtattccgagctcgaagaaggcggcgttataatgcaggccttctactgggacgtcccaggtggaggaatctggtgggacaccatcaggagcaagataccggagtggtacgaggcgggaatatccgccatttggattccgccagccagcaaggggatgagcggcggttactcgatgggctacgatccctacgatttctttgacctcggcgagtacaaccagaagggaaccatcgaaacgcgctttggctctaaacaggagctcatcaatatgataaacacggcccatgcctacggcataaaggtcatagcggacatcgtcataaaccaccgcgcaggcggagacctcgagtggaacccgttcgttggggactacacctggacggacttctcaaaggtggcctcgggcaaatatactgccaactacctcgacttccacccaacgaggtcaagtgctgtgacgagggcacatttggaggcttcccagacatagcccacgagaagagctggaccagcactggctctgggcgagcgatgagagctacgccgcctacctaaggagcatcggcgttgatgcctggcgctttgactacgtgaagggctacggagcgtgggtcgtcaaggactggctcaactggtggggcggctggccgttggc gagtactgggacaccaacgttgatgcactcctcaactgggcctactcgagcggcgccaaggtcttcgacttcccgctctactacaagatggatg
aggcctttgacaacaaaaacattccagcgctcgtctctgcccttcagaacggccagactgttgtctcccgcgacccgttcaaggccgtaaccttt
gtagcaaaccacgacaccgatataatctggaacaagtaccttgcttatgctttcatcctcacctacgaaggccagcccgtcatattctaccgcgac
tacgaggagtggctcaacaaggacaggttgaacaacctcatatggatacacgaccacctcgcaggtggaagcacgagcatagtctactacga
cagcgacgagatgatcttcgtgaggaacggctatggaagcaagcctggcctttataacttacatcaacctcggctcgagcaaggttggaaggtg
ggtttatgtgccgaagttcgcgggcgcgtgcatccacgagtatactggtaacctcggaggctgggtagacaagtacgtctactcaagcggctg
ggtctatctcgaagctccagcttacgaccctgccaacgggcagtatggctactccgtgtggagctattgcggtgttgggtga SEQ ID NO: 7
Met Phe Leu Leu Ala Phe Leu Leu Thr Ala Ser Leu Phe Cys Pro Thr Gly Gln Pro Ala Lys Ala Ala
Ala Pro Phe Asn Gly Thr Met Met Gln Tyr Phe Glu Trp Tyr Leu Pro Asp Asp Gly Thr Leu Trp Thr
Lys Val Ala Asn Glu Ala Asn Asn Leu Ser Ser Leu Gly Ile Thr Ala Leu Trp Leu Pro Pro Ala Tyr
Lys Gly Thr Ser Arg Ser Asp Val Gly Tyr Gly Val Tyr Asp Leu Tyr Asp Leu Gly Glu Phe Asn Gln
Lys Gly Thr Val Arg Thr Lys Tyr Gly Thr Lys Ala Gln Tyr Leu Gln Ala Ile Gln Ala Ala His Ala
Ala Gly Met Gln Val Tyr Ala Asp Val Val Phe Asp His Lys Gly Gly Ala Asp Gly Thr Glu Trp Val
Asp Ala Val Glu Val Asn Pro Ser Asp Arg Asn Gln Glu Ile Ser Gly Thr Tyr Gln Ile Gln Ala Trp
Thr Lys Phe Asp Phe Pro Gly Arg Gly Asn Thr Tyr Ser Ser Phe Lys Trp Arg Trp Tyr His Phe Asp
Gly Val Asp Trp Asp Glu Ser Arg Lys Leu Ser Arg Ile Tyr Lys Phe Arg Gly Ile Gly Lys Ala Trp
Asp Trp Glu Val Asp Thr Glu Asn Gly Asn Tyr Asp Tyr Leu Met Tyr Ala Asp Leu Asp Met Asp
His Pro Glu Val Val Thr Glu Leu Lys Asn Trp Gly Lys Trp Tyr Val Asn Thr Thr Asn Ile Asp Gly
Phe Arg Leu Asp Ala Val Lys His Ile Lys Phe Ser Phe Phe Pro Asp Trp Leu Ser Tyr Val Arg Ser
Gln Thr Gly Lys Pro Leu Phe Thr Val Gly Glu Tyr Trp Ser Tyr Asp Ile Asn Lys Leu His Asn Tyr
Ile Thr Lys Thr Asp Gly Thr Met Ser Leu Phe Asp Ala Pro Leu His Asn Lys Phe Tyr Thr Ala Ser
Lys Ser Gly Gly Ala Phe Asp Met Arg Thr Leu Met Thr Asn Thr Leu Met Lys Asp Gln Pro Thr
Leu Ala Val Thr Phe Val Asp Asn His Asp Thr Glu Pro Gly Gln Ala Leu Gln Ser Trp Val Asp Pro
Trp Phe Lys Pro Leu Ala Tyr Ala Phe Ile Leu Thr Arg Gln Glu Gly Tyr Pro Cys Val Phe Tyr Gly
Asp Tyr Tyr Gly Ile Pro Gln Tyr Asn Ile Pro Ser Leu Lys Ser Lys Ile Asp Pro Leu Leu Ile Ala Arg
Arg Asp Tyr Ala Tyr Gly Thr Gln His Asp Tyr Leu Asp His Ser Asp Ile Ile Gly Trp Thr Arg Glu
Gly Val Thr Glu Lys Pro Gly Ser Gly Leu Ala Ala Leu Ile Thr Asp Gly Pro Gly Gly Ser Lys Trp
Met Tyr Cys Trp Gln Thr Thr Arg Trp Lys Ser Val Leu SEQ ID NO: 8
Met Lys Gln Gln Lys Arg Leu Tyr Ala Arg Leu Leu Thr Leu Leu Phe Ala Leu Ile Phe Leu Leu Pro
His Ser Ala Ala Ala Ala Asn Leu Asn Gly Thr Leu Met Gln Tyr Phe Glu Trp Tyr Met Pro Asn
Asp Gly Gln His Trp Lys Arg Leu Gln Asn Asp Ser Ala Tyr Leu Ala Glu His Gly Ile Thr Ala Val
Trp Ile Pro Pro Ala Tyr Lys Gly Thr Ser Gln Ala Asp Val Gly Tyr Gly Ala Tyr Asp Leu Tyr Asp
Leu Gly Glu Phe His Gln Lys Gly Thr Val Arg Thr Lys Tyr Gly Thr Lys Gly Glu Leu Gln Ser Ala
Ile Lys Ser Leu His Ser Arg Asp Ile Asn Val Tyr Gly Asp Val Val Ile Asn His Lys Gly Gly Ala
Asp Ala Thr Glu Asp Val Thr Ala Val Glu Val Asp Pro Ala Asp Arg Asn Arg Val Ile Ser Gly Glu
His Arg Ile Lys Ala Trp Thr His Phe His Phe Pro Gly Arg Gly Ser Thr Tyr Ser Asp Phe Lys Trp
His Trp Tyr His Phe Asp Gly Thr Asp Trp Asp Glu Ser Arg Lys Leu Asn Arg Ile Tyr Lys Phe Gln
Gly Lys Ala Trp Asp Trp Glu Val Ser Asn Glu Asn Gly Asn Tyr Asp Tyr Leu Met Tyr Ala Asp Ile
Asp Tyr Asp His Pro Asp Val Ala Ala Glu Ile Lys Arg Trp Gly Thr Trp Tyr Ala Asn Glu Leu Gln
Leu Asp Gly Phe Arg Leu Asp Ala Val Lys His Ile Lys Phe Ser Phe Leu Arg Asp Trp Val Asn His
Val Arg Glu Lys Thr Gly Lys Glu Met Phe Thr Val Ala Glu Tyr Trp Gln Asn Asp Leu Gly Ala
Leu Glu Asn Tyr Leu Asn Lys Thr Asn Phe Asn His Ser Val Phe Asp Val Pro Leu His Tyr Gln Phe
His Ala Ala Ser Thr Gln Gly Gly Gly Tyr Asp Met Arg Lys Leu Leu Asn Gly Thr Val Val Ser Lys
His Pro Leu Lys Ala Val Thr Phe Val Asp Asn His Asp Thr Gln Pro Gly Gln Ser Leu Glu Ser Thr
Val Gln Thr Trp Phe Lys Pro Leu Ala Tyr Ala Phe Ile Leu Thr Arg Glu Ser Gly Tyr Pro Gln Val
Phe Tyr Gly Asp Met Tyr Gly Thr Lys Gly Asp Ser Gln Arg Glu Ile Pro Ala Leu Lys His Lys Ile
Glu Pro Ile Leu Lys Ala Arg Lys Gln Tyr Ala Tyr Gly Ala Gln His Asp Tyr Phe Asp His His Asp Ile Val Gly Trp Thr Arg Glu Gly Asp Ser Ser Val Ala Asn Ser Gly Leu Ala Ala Leu Ile Thr Asp
Gly Pro Gly Gly Ala Lys Arg Met Tyr Val Gly Arg Gln Asn Ala Gly Glu Thr Trp His Asp Ile Thr
Gly Asn Arg Ser Glu Pro Val Val Ile Asn Ser Glu Gly Trp Gly Glu Phe His Val Asn Gly Gly Ser
Val Ser Ile Tyr Val Gln Arg SEQ ID NO: 9
Val Val His Met Lys Leu Lys Tyr Leu Ala Leu Val Leu Leu Ala Val Ala Ser Ile Gly Leu Leu Ser
Thr Pro Val Gly Ala Ala Lys Tyr Ser Glu Leu Glu Glu Gly Gly Val Ile Met Gln Ala Phe Tyr Trp
Asp Val Pro Gly Gly Gly Ile Trp Trp Asp Thr Ile Arg Gln Lys Ile Pro Glu Trp Tyr Asp Ala Gly Ile
Ser Ala Ile Trp Ile Pro Pro Ala Ser Lys Gly Met Gly Gly Gly Tyr Ser Met Gly Tyr Asp Pro Tyr
Asp Phe Phe Asp Leu Gly Glu Tyr Tyr Gln Lys Gly Thr Val Glu Thr Arg Phe Gly Ser Lys Glu Glu
Leu Val Asn Met Ile Asn Thr Ala His Ser Tyr Gly Ile Lys Val Ile Ala Asp Ile Val Ile Asn His Arg
Ala Gly Gly Asp Leu Glu Trp Asn Pro Phe Val Asn Asn Tyr Thr Trp Thr Asp Phe Ser Lys Val Ala
Ser Gly Lys Tyr Thr Ala Asn Tyr Leu Asp Phe His Pro Asn Glu Val Lys Cys Cys Asp Glu Gly Thr
Phe Gly Asp Phe Pro Asp Ile Ala His Glu Lys Ser Trp Asp Gln Tyr Trp Leu Trp Ala Ser Asn Glu
Ser Tyr Ala Ala Tyr Leu Arg Ser Ile Gly Ile Asp Ala Trp Arg Phe Asp Tyr Val Lys Gly Tyr Gly
Ala Trp Val Val Asn Asp Trp Leu Ser Trp Trp Gly Gly Trp Ala Val Gly Glu Tyr Trp Asp Thr Asn
Val Asp Ala Leu Leu Asn Trp Ala Tyr Asp Ser Gly Ala Lys Val Phe Asp Phe Pro Leu Tyr Tyr Lys
Met Asp Glu Ala Phe Asp Asn Thr Asn Ile Pro Ala Leu Val Tyr Ala Leu Gln Asn Gly Gly Thr Val
Val Ser Arg Asp Pro Phe Lys Ala Val Thr Phe Val Ala Asn His Asp Thr Asp Ile Ile Trp Asn Lys
Tyr Pro Ala Tyr Ala Phe Ile Leu Thr Tyr Glu Gly Gln Pro Val Ile Phe Tyr Arg Asp Tyr Glu Glu
Trp Leu Asn Lys Asp Lys Leu Asn Asn Leu Ile Trp Ile His Glu His Leu Ala Gly Gly Ser Thr Lys
Ile Leu Tyr Tyr Asp Asn Asp Glu Leu Ile Phe Met Arg Glu Gly Tyr Gly Ser Lys Pro Gly Leu Ile
Thr Tyr Ile Asn Leu Gly Asn Asp Trp Ala Glu Arg Trp Val Asn Val Gly Ser Lys Phe Ala Gly Tyr
Thr Ile His Glu Tyr Thr Gly Asn Leu Gly Gly Trp Val Asp Arg Trp Val Gln Tyr Asp Gly Trp Val
Lys Leu Thr Ala Pro Pro His Asp Pro Ala Asn Gly Tyr Tyr Gly Tyr Ser Val Trp Ser Tyr Ala Gly
Val Gly SEQ ID NO.: 10
Met Lys Lys Phe Val Ala Leu Phe Ile Thr Met Phe Phe Val Val Ser Met Ala Val Val Ala Gln Pro
Ala Ser Ala Ala Lys Tyr Ser Glu Leu Glu Glu Gly Gly Val Ile Met Gln Ala Phe Tyr Trp Asp Val
Pro Gly Gly Gly Ile Trp Trp Asp Thr Ile Arg Ser Lys Ile Pro Glu Trp Tyr Glu Ala Gly Ile Ser Ala
Ile Trp Ile Pro Pro Ala Ser Lys Gly Met Ser Gly Gly Tyr Ser Met Gly Tyr Asp Pro Tyr Asp Phe
Phe Asp Leu Gly Glu Tyr Asn Gln Lys Gly Thr Ile Glu Thr Arg Phe Gly Ser Lys Gln Glu Leu Ile
Asn Met Ile Asn Thr Ala His Ala Tyr Gly Ile Lys Val Ile Ala Asp Ile Val Ile Asn His Arg Ala Gly
Gly Asp Leu Glu Trp Asn Pro Phe Val Gly Asp Tyr Thr Trp Thr Asp Phe Ser Lys Val Ala Ser Gly
Lys Tyr Thr Ala Asn Tyr Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp Leu Trp Ala Ser Asp Glu Ser
Tyr Ala Ala Tyr Leu Arg Ser Ile Gly Val Asp Ala Trp Arg Phe Asp Tyr Val Lys Gly Tyr Gly Ala
Trp Val Val Lys Asp Trp Leu Asn Trp Trp Gly Gly Trp Ala Val Gly Glu Tyr Trp Asp Thr Asn Val
Asp Ala Leu Leu Asn Trp Ala Tyr Ser Ser Gly Ala Lys Val Phe Asp Phe Pro Leu Tyr Tyr Lys Met
Asp Glu Ala Phe Asp Asn Lys Asn Ile Pro Ala Leu Val Ser Ala Leu Gln Asn Gly Gln Thr Val Val
Ser Arg Asp Pro Phe Lys Ala Val Thr Phe Val Ala Asn His Asp Thr Asp Ile Ile Trp Asn Lys Tyr
Leu Ala Tyr Ala Phe Ile Leu Thr Tyr Glu Gly Gln Pro Val Ile Phe Tyr Arg Asp Tyr Glu Glu Trp
Leu Asn Lys Asp Arg Leu Asn Asn Leu Ile Trp Ile His Asp His Leu Ala Gly Gly Ser Thr Ser Ile
Val Tyr Tyr Asp Ser Asp Glu Met Ile Phe Val Arg Asn Gly Tyr Gly Ser Lys Pro Gly Leu Ile Thr
Tyr Ile Asn Leu Gly Ser Ser Lys Val Gly Arg Trp Val Tyr Val Pro Lys Phe Ala Gly Ala Cys Ile
His Glu Tyr Thr Gly Asn Leu Gly Gly Trp Val Asp Lys Tyr Val Tyr Ser Ser Gly Trp Val Tyr Leu
Glu Ala Pro Ala Tyr Asp Pro Ala Asn Gly Gln Tyr Gly Tyr Ser Val Trp Ser Tyr Cys Gly Val Gly SEQ ID NO: 66
atggctctggaagagggcgggcttataatgcaggcattctactgggacgtccccatgggaggaatctggtgggacacgatagcccagaagat
acccgactgggcaagcgccgggatttcggcgatatggattcccccgcgagcaagggtatgagcggcggctattcgatgggctacgacccct
acgattattttgacctcggtgagtactaccagaagggaacggtggaaacaagattcggctcaaagcaggagctcataaacatgataaacaccg
cccacgcctatggcatgaaggtaatagccgatatagtcatcaaccaccgcgccggcggcgatctggagtggaaccccttcgtgaacgactata
cctggaccgacttctcgaaggtcgcgtcgggtaaatacacggccaactacctcgacttccacccgaacgagctccacgcgggcgattccgga
acatttggaggctatcccgacatatgccacgacaagagctgggaccagtactggctctgggccagccaggagagctacgcggcctatctcag
gagcatcggcatcgacgcctggcgcttcgactacgtcaagggctatgctccctgggtcgtcagggactggctgaactggtggggaggctggg
cagttggagagtactgggacaccaacgtcgacgctgttctcaactgggcatactcgagcggtgccaaggtctttgacttcgccctctactacaag
atggacgaggccttcgataacaacaacattcccgccctggtggacgccctcagatacggccagacagtggtcagccgcgaccgttcaaggc
tgtgacgtttgtagccaaccacgataccgacataatctggaacaagtatccagcctacgcgttcatcctcacctacgagggccagccgacaatat
tctaccgcgactacgaggagtggctcaacaaggacaagctcaagaacctcatctggatacatgacaacctcgccggagggagcactgacatc
gtttactacgacaacgacgagctgatattcgtgagaaacggctacggaagcaagccgggactgataacatacatcaacctcggctcaagcaaa
gccggaaggtgggtttacgttccgaagttcgcaggctcgtgcatacacgagtacaccggcaacctcggcggctgggtggacaagtgggtgga
ctcaagcggctgggtttacctcgaggctcctgcccacgacccggccaacggccagtacggctactccgtttggagctattgcggtgttgggtga SEQ ID NO: 67
Met Ala Leu Glu Glu Gly Gly Leu Ile Met Gln Ala Phe Tyr Trp Asp Val Pro Met Gly Gly Ile Trp
Trp Asp Thr Ile Ala Gln Lys Ile Pro Asp Trp Ala Ser Ala Gly Ile Ser Ala Ile Trp Ile Pro Pro Ala
Ser Lys Gly Met Ser Gly Gly Tyr Ser Met Gly Tyr Asp Pro Tyr Asp Tyr Phe Asp Leu Gly Glu Tyr
Tyr Gln Lys Gly Thr Val Glu Thr Arg Phe Gly Ser Lys Gln Glu Leu Ile Asn Met Ile Asn Thr Ala
His Ala Tyr Gly Met Lys Val Ile Ala Asp Ile Val Ile Asn His Arg Ala Gly Gly Asp Leu Glu Trp
Asn Pro Phe Val Asn Asp Tyr Thr Trp Thr Asp Phe Ser Lys Val Ala Ser Gly Lys Tyr Thr Ala Asn
Tyr Leu Asp Phe His Pro Asn Glu Leu His Ala Gly Asp Ser Gly Thr Phe Gly Gly Tyr Pro Asp Ile
Cys His Asp Lys Ser Trp Asp Gln Tyr Trp Leu Trp Ala Ser Gln Glu Ser Tyr Ala Ala Tyr Leu Arg
Ser Ile Gly Ile Asp Ala Trp Arg Phe Asp Tyr Val Lys Gly Tyr Ala Pro Trp Val Val Arg Asp Trp
Leu Asn Trp Trp Gly Gly Trp Ala Val Gly Glu Tyr Trp Asp Thr Asn Val Asp Ala Val Leu Asn Trp
Ala Tyr Ser Ser Gly Ala Lys Val Phe Asp Phe Ala Leu Tyr Tyr Lys Met Asp Glu Ala Phe Asp Asn
Asn Asn Ile Pro Ala Leu Val Asp Ala Leu Arg Tyr Gly Gln Thr Val Val Ser Arg Asp Pro Phe Lys
Ala Val Thr Phe Val Ala Asn His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu Trp Leu Asn Lys Asp Lys Leu
Lys Asn Leu Ile Trp Ile His Asp Asn Leu Ala Gly Gly Ser Thr Asp Ile Val Tyr Tyr Asp Asn Asp
Glu Leu Ile Phe Val Arg Asn Gly Tyr Gly Ser Lys Pro Gly Leu Ile Thr Tyr Ile Asn Leu Gly Ser Ser
Lys Ala Gly Arg Trp Val Tyr Val Pro Lys Phe Ala Gly Ser Cys Ile His Glu Tyr Thr Gly Asn Leu
Gly Gly Trp Val Asp Lys Trp Val Asp Ser Ser Gly Trp Val Tyr Leu Glu Ala Pro Ala His Asp Pro
Ala Asn Gly Gln Tyr Gly Tyr Ser Val Trp Ser Tyr Cys Gly Val Gly SEQ ID NO: 68
atgaagcctgcgaaactcctcgtctttgtgctcgtagtctctatcctcgcggggctctacgcccagcccgcggggggcggccaagtacctggagc
tcgaagagggcggcgtcataatgcaggcgttctactgggacgtgccttcaggaggaatatggtgggacacaatacggcagaagataccgga
gtggtacgatgccggaatctccgcaatatggattcccccggcgagcaagggcatgggcggcgccattcgatgggctacgaccccctacgactt
ctttgacctcggtgagtacgaccagaagggaacggtagagacgcgctttggctccaagcaggagctcgtgaacatgataaacaccgccacg
cctacggcatcaaggtcatcgcagacatagtaatcaaccaccgcgccggaggagaccttgagtggaacccccttcgtcaatgactacacctgga
cggacttctcgaaggtcgcttccggcaagtacacggccaactacctcgacttccaccccaacgaggtcaagtgctgcgacgagggcaccttg
gagggttcccggacatagcccacgagaagagctgggaccagtactggctctgggcgagcaacgagagctacgccgcctacctcaggagca
tcggcgttgacgcatggcgcttcgactacgtcaagggctacggagcgtggtcgtcaaggactggctggactggtggggaggctgggccgt
cgggggagtactgggacacaaacgttgatgcactgctcaactgggcctactcgagcgatgcaaaagtcttcgacttcccgctctactacaagatg
gacgcggcctttgacaacaagaacattcccgcactcgtcgaggccctcaagaacgggggcacagtcgtcagccgcgacccgtttaaggccgt
aaccttcgttgcaaaccacgacacggacataatttggaacaagtacccggcctacgccttcatcctcacctacgagggccagccgacgatattc
taccgcgactacgaggagtggctcaacaaggacaggctcaagaacctcatctggatacacgaccacctcgccggtggaagcaccgacatag tctactacgataacgatgaactcatcttcgtcaggaacggctacggggacaagccggggcttataacctacatcaacctaggctcgagcaagg
ccgggaggtgggtctacgttccgaagttcgcgggagcgtgcatccacgagtacaccggcaacctcggcggctgggtggacaagtgggtgga
ctcaagcgggtgggtgtacctcgaggcccctgcccacgacccggccaacggctattacggctactccgtctggagctactgcggggtgggct
ga SEQ ID NO: 69
Met Lys Pro Ala Lys Leu Leu Val Phe Val Leu Val Val Ser Ile Leu Ala Gly Leu Tyr Ala Gln Pro
Ala Gly Ala Ala Lys Tyr Leu Glu Leu Glu Glu Gly Gly Val Ile Met Gln Ala Phe Tyr Trp Asp Val
Pro Ser Gly Gly Ile Trp Trp Asp Thr Ile Arg Gln Lys Ile Pro Glu Trp Tyr Asp Ala Gly Ile Ser Ala
Ile Trp Ile Pro Pro Ala Ser Lys Gly Met Gly Gly Ala Tyr Ser Met Gly Tyr Asp Pro Tyr Asp Phe
Phe Asp Leu Gly Glu Tyr Asp Gln Lys Gly Thr Val Glu Thr Arg Phe Gly Ser Lys Gln Glu Leu Val
Asn Met Ile Asn Thr Ala His Ala Tyr Gly Ile Lys Val Ile Ala Asp Ile Val Ile Asn His Arg Ala Gly
Gly Asp Leu Glu Trp Asn Pro Phe Val Asn Asp Tyr Thr Trp Thr Asp Phe Ser Lys Val Ala Ser Gly
Lys Tyr Thr Ala Asn Tyr Leu Asp Phe His Pro Asn Glu Val Lys Cys Cys Asp Glu Gly Thr Phe
Gly Gly Phe Pro Asp Ile Ala His Glu Lys Ser Trp Asp Gln Tyr Trp Leu Trp Ala Ser Asn Glu Ser
Tyr Ala Ala Tyr Leu Arg Ser Ile Gly Val Asp Ala Trp Arg Phe Asp Tyr Val Lys Gly Tyr Gly Ala
Trp Val Val Lys Asp Trp Leu Asp Trp Trp Gly Gly Trp Ala Val Gly Glu Tyr Trp Asp Thr Asn Val
Asp Ala Leu Leu Asn Trp Ala Tyr Ser Ser Asp Ala Lys Val Phe Asp Phe Pro Leu Tyr Tyr Lys Met
Asp Ala Ala Phe Asp Asn Lys Asn Ile Pro Ala Leu Val Glu Ala Leu Lys Asn Gly Gly Thr Val Val
Ser Arg Asp Pro Phe Lys Ala Val Thr Phe Val Ala Asn His Asp Thr Asp Ile Ile Trp Asn Lys Tyr
Pro Ala Tyr Ala Phe Ile Leu Thr Tyr Glu Gly Gln Pro Thr Ile Phe Tyr Arg Asp Tyr Glu Glu Trp
Leu Asn Lys Asp Arg Leu Lys Asn Leu Ile Trp Ile His Asp His Leu Ala Gly Gly Ser Thr Asp Ile
Val Tyr Tyr Asp Asn Asp Glu Leu Ile Phe Val Arg Asn Gly Tyr Gly Asp Lys Pro Gly Leu Ile Thr
Tyr Ile Asn Leu Gly Ser Ser Lys Ala Gly Arg Trp Val Tyr Val Pro Lys Phe Ala Gly Ala Cys Ile
His Glu Tyr Thr Gly Asn Leu Gly Gly Trp Val Asp Lys Trp Val Asp Ser Ser Gly Trp Val Tyr Leu
Glu Ala Pro Ala His Asp Pro Ala Asn Gly Tyr Tyr Gly Tyr Ser Val Trp Ser Tyr Cys Gly Val Gly

ENZYMES HAVING ALPHA AMYLASE ACTIVITY AND METHODS OF USE THEREOF

RELATED APPLICATION DATA

This application claims priority of U.S. Provisional Application No. 60/270,495, filed Feb. 21, 2001, now pending; U.S. Provisional Application No. 60/270,496, filed Feb. 21, 2001, now pending; and U.S. Provisional Application No. 60/291,122, filed May 14, 2001, now pending, all of which are herein incorporated by reference in their entirety.

FIELD OF THE INVENTION

This invention relates generally to enzymes, polynucleotides encoding the enzymes, the use of such polynucleotides and polypeptides, and more specifically to enzymes having alpha amylase activity.

BACKGROUND

Starch is a complex carbohydrate often found in the human diet. The structure of starch is glucose polymers linked by α-1,4 and α-1,6 glucosidic bonds. Amylase is an enzyme that catalyzes the hydrolysis of starches into sugars. Amylases hydrolyze internal α-1,4-glucosidic linkages in starch, largely at random, to produce smaller molecular weight malto-dextrins. The breakdown of starch is important in the digestive system and commercially. Amylases are of considerable commercial value, being used in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper; and in animal feed. Amylases are also useful in textile desizing, brewing processes, starch modification in the paper and pulp industry and other processes described in the art.

Amylases are produced by a wide variety of microorganisms including Bacillus and Aspergillus, with most commercial amylases being produced from bacterial sources such as Bacillus licheniformis, Bacillus amyloliquefaciens, Bacillus subtilis, or Bacillus stearothermophilus. In recent years, the enzymes in commercial use have been those from Bacillus licheniformis because of their heat stability and performance, at least at neutral and mildly alkaline pHs.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by amylase. A starch granule is composed of: 69-74% amylopectin, 26-31% amylose, 11-14% water, 0.2-0.4% protein, 0.5-0.9% lipid, 0.05-0.1% ash, 0.02-0.03% phosphorus, 0.1% pentosan. Approximately 70% of a granule is amorphous and 30% is crystalline.

A common enzymatic liquefaction process involves adjusting the pH of a granular starch slurry to between 6.0 and 6.5, the pH optimum of alpha-amylase derived from Bacillus licheniformis, with the addition of calcium hydroxide, sodium hydroxide or sodium carbonate. The addition of calcium hydroxide has the advantage of also providing calcium ions which are known to stabilize the alpha-amylase against inactivation. Upon addition of alpha-amylase, the suspension is pumped through a steam jet to instantaneously raise the temperature to between 80 degree-115 degrees C. The starch is immediately gelatinized and, due to the presence of alpha-amylase, depolymerized through random hydrolysis of a (1-4) glycosidic bonds by alpha-amylase to a fluid mass which is easily pumped.

In a second variation to the liquefaction process, alpha-amylase is added to the starch suspension, the suspension is held at a temperature of 80-100 degrees C. to partially hydrolyze the starch granules, and the partially hydrolyzed starch suspension is pumped through a jet at temperatures in excess of about 105 degrees C. to thoroughly gelatinize any remaining granular structure. After cooling the gelatinized starch, a second addition of alpha-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using alpha amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of alpha-amylase until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Corn wet milling is a process which produces corn oil, gluten meal, gluten feed and starch. Often, alkaline-amylase is used in the liquefaction of starch and glucoamylase is used in saccharification, producing glucose. Corn, a kernel of which consists of a outer seed coat (fiber), starch, a combination of starch and glucose and the inner germ, is subjected to a four step process, which results in the production of starch. The corn is steeped, de-germed, de-fibered, and finally the gluten is separated. In the steeping process, the solubles are taken out. The product remaining after removal of the solubles is de-germed, resulting in production of corn oil and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification to produce glucose.

Staling of baked products (such as bread) has been recognized as a problem which becomes more serious as more time lies between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. The increase in crumb firmness, which is considered as the most important aspect of staling, is recognized by the consumer a long time before the bread product has otherwise become unsuitable for consumption.

The preparation of syrup process contains proportions of polymers with degrees of polymerisation (DP) greater than or equal to 4, which could be troublesome. U.S. Pat. No. 5,141,859 proposed a process for the preparation of a syrup with a high maltose content employing two successive saccharification steps. This document advocates, in fact, a process comprising a first saccharification step in the presence of a beta amylase and a subsequent saccharification step in the presence of a maltogenic alpha amylase. According to this document, the maltogenic alpha amylase is used after the first saccharification step with beta amylase to hydrolyse the oligosaccharides (from DP3 to DP7) and essentially the maltotriose (trisaccharide) to maltose and glucose.

There is therefore a need in the industry for the identification and optimization of acid amylases, useful for commercial cornstarch liquefaction processes. These second generation acid amylases will offer improved manufacturing and/or performance characteristics over the industry standard enzymes.

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

The invention provides an isolated nucleic acid having a sequence as set forth in SEQ ID NO:1 and variants thereof having at least 50% sequence identity to SEQ ID NO:1 and encoding polypeptides having alpha amylase activity.

One aspect of the invention is an isolated nucleic acid having a sequence as set forth in SEQ ID NO:1, sequences substantially identical thereto, and sequences complementary thereto.

Another aspect of the invention is an isolated nucleic acid including at least 10 consecutive bases of a sequence as set forth in SEQ ID NO:1 nucleic acid sequences, sequences substantially identical thereto, and the sequences complementary thereto.

In yet another aspect, the invention provides an isolated nucleic acid encoding a polypeptide having a sequence as set forth in SEQ ID NO.: 2 and variants thereof encoding a polypeptide having alpha amylase activity and having at least 50% sequence identity to such sequences.

Another aspect of the invention is an isolated nucleic acid encoding a polypeptide or a functional fragment thereof having a sequence as set forth in SEQ ID NO:2 and sequences substantially identical thereto.

Another aspect of the invention is an isolated nucleic acid encoding a polypeptide having at least 10 consecutive amino acids of a sequence as set forth in SEQ ID NO:2 amino acid sequences, and sequences substantially identical thereto.

In yet another aspect, the invention provides a purified polypeptide having a sequence as set forth in SEQ ID NO:2 amino acid sequences, and sequences substantially identical thereto.

Another aspect of the invention is an isolated or purified antibody that specifically binds to a polypeptide having a sequence as set forth in SEQ ID NO:2 amino acid sequences, and sequences substantially identical thereto.

Another aspect of the invention is an isolated or purified antibody or binding fragment thereof, which specifically binds to a polypeptide having at least 10 consecutive amino acids of one of the polypeptides of SEQ ID NO:2 amino acid sequences, and sequences substantially identical thereto.

Another aspect of the invention is a method of making a polypeptide having a sequence as set forth in SEQ ID NO:2 amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in SEQ ID NO:2 amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in SEQ ID NO:1 nucleic acid sequences, sequences substantially identical thereto, sequences complementary to the sequences of SEQ ID NO:1 nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in SEQ ID NO:1 nucleic acid sequences, and sequences substantially identical thereto, or a polypeptide sequence as set forth in SEQ ID NO:2 amino acid sequences, and sequences substantially identical thereto.

Another aspect of the invention is a computer system including a processor and a data storage device wherein the data storage device has stored thereon a sequence as set forth in SEQ ID NO:1 nucleic acid sequences, and sequences substantially identical thereto, or a polypeptide having a sequence as set forth in SEQ ID NO:2 amino acid sequences, and sequences substantially identical thereto.

Another aspect of the invention is a method for comparing a first sequence to a reference sequence wherein the first sequence is a nucleic acid having a sequence as set forth in SEQ ID NO:1 nucleic acid sequences, and sequences substantially identical thereto, or a polypeptide code of SEQ ID NO:2 amino acid sequences, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in SEQ ID NO:1 nucleic acid sequences, and sequences substantially identical thereto, or a polypeptide having a sequence as set forth in SEQ ID NO:2 amino acid sequences, and sequences substantially identical thereto, including reading the sequence through the use of a computer program which identifies features in sequences; and identifying features in the sequence with the computer program.

Another aspect of the invention is an assay for identifying fragments or variants of SEQ ID NO:2 amino acid sequences, and sequences substantially identical thereto, which retain the enzymatic function of the polypeptides of SEQ ID NO:2 amino acid sequences, and sequences substantially identical thereto. The assay includes contacting the polypeptide of SEQ ID NO:2 amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase.

The use of the amylase in accordance with the present invention provides an improved anti-staling effect as measured by, e.g. less crumb firming, retained crumb elasticity, improved slice-ability (e.g. fewer crumbs, non-gummy crumb), improved palatability or flavor.

BRIEF DESCRIPTION OF THE DRAWINGS

The following drawings are illustrative of embodiments of the invention and are not meant to limit the scope of the invention as encompassed by the claims.

FIG. 5 illustrates a sample Standard Curve of the assay of Example 2.

FIG. 7 is the sequences of the invention.

DETAILED DESCRIPTION OF THE INVENTION

The present invention relates to alpha amylases and polynucleotides encoding them. As used herein, the term "alpha amylase" encompasses enzymes having alpha amylase activity, for example, enzymes capable of hydrolyzing starch to sugars. Unlike many known amylases, the exemplary amylase of the invention, set forth in SEQ ID NO:2, is not a calcium-dependent enzyme.

It is highly desirable to be able to decrease the Ca2+ dependency of an alpha amylase. Accordingly, one aspect of the invention provides an amylase enzyme that has a decreased Ca2+ dependency as compared to commercial or parent amylases. Decreased Ca2+ dependency will in general have the functional consequence that the variant exhibits a satisfactory amylolytic activity in the presence of a lower concentration of calcium ion in the extraneous medium than is necessary for a commercial or parent enzyme. It will further often have the consequence that the variant is less sensitive to calcium ion-depleting conditions such as those obtained in media containing calcium-complexing agents (such as certain detergent builders).

The polynucleotides of the invention have been identified as encoding polypeptides having alpha amylase activity. An exemplary alpha amylase enzyme of the invention is shown in SEQ ID NO:2, also referred to herein as SEQ ID NO:2. Such amylases of the invention are particularly useful in corn-wet milling processes, detergents, baking processes, beverages and in oilfields (fuel ethanol).

Alterations in properties which may be achieved in variants of the invention are alterations in, e.g., substrate specificity, substrate binding, substrate cleavage pattern, thermal stability, pH/activity profile, pH/stability profile, such as increased stability at low (e.g. pH<6, in particular pH<5) or high (e.g. pH>9) pH values], stability towards oxidation, Ca2+ dependency, specific activity, and other properties of interest. For instance, the alteration may result in a variant which, as compared to the parent amylase, has a reduced Ca2+ dependency and/or an altered pH/activity profile.

Figure 6A:
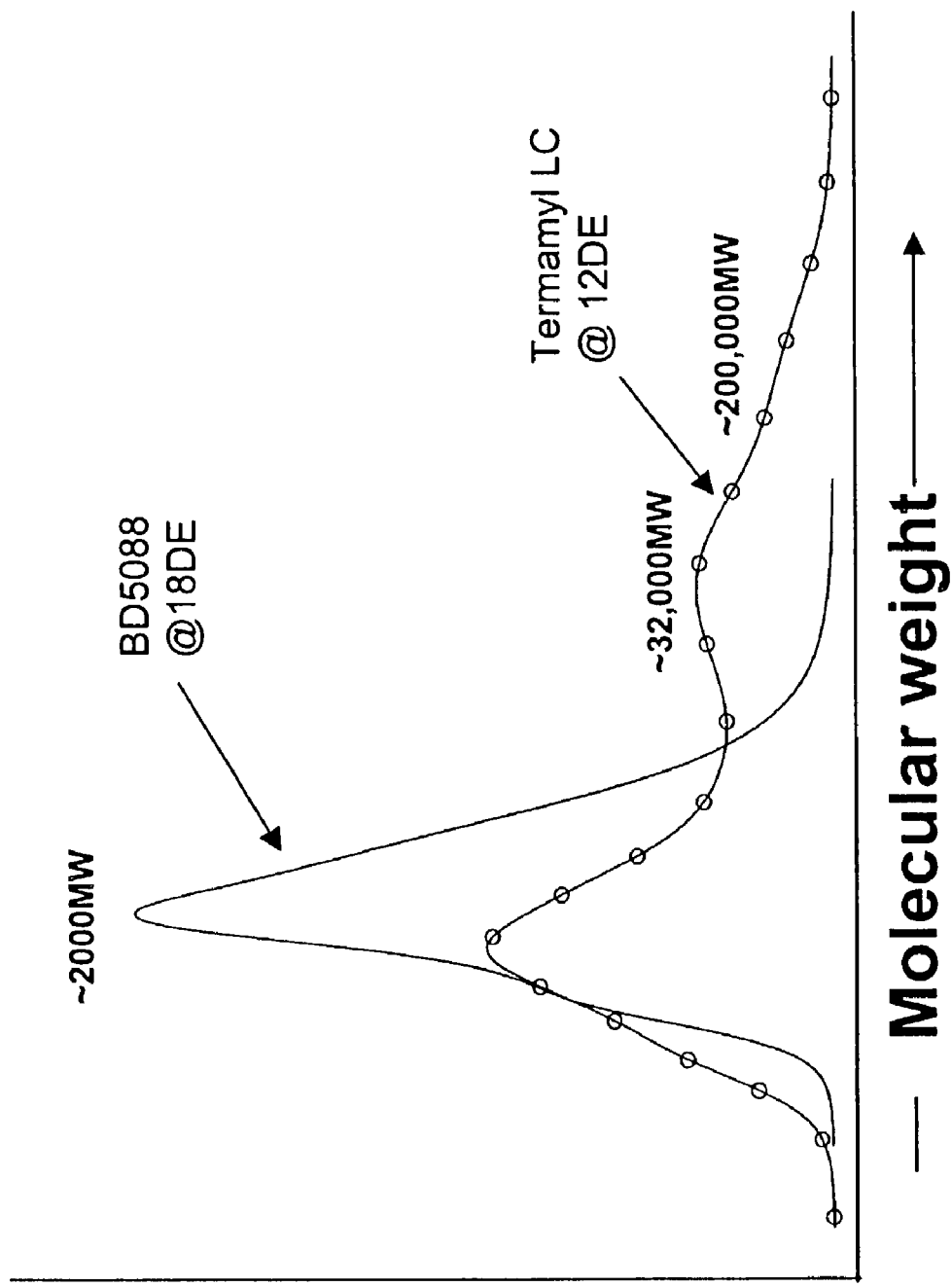
FIGS. 6a and 6b show the molecular weight fragments in syrups using enzymes of the invention and commercial enzymes.
Figure 6B:
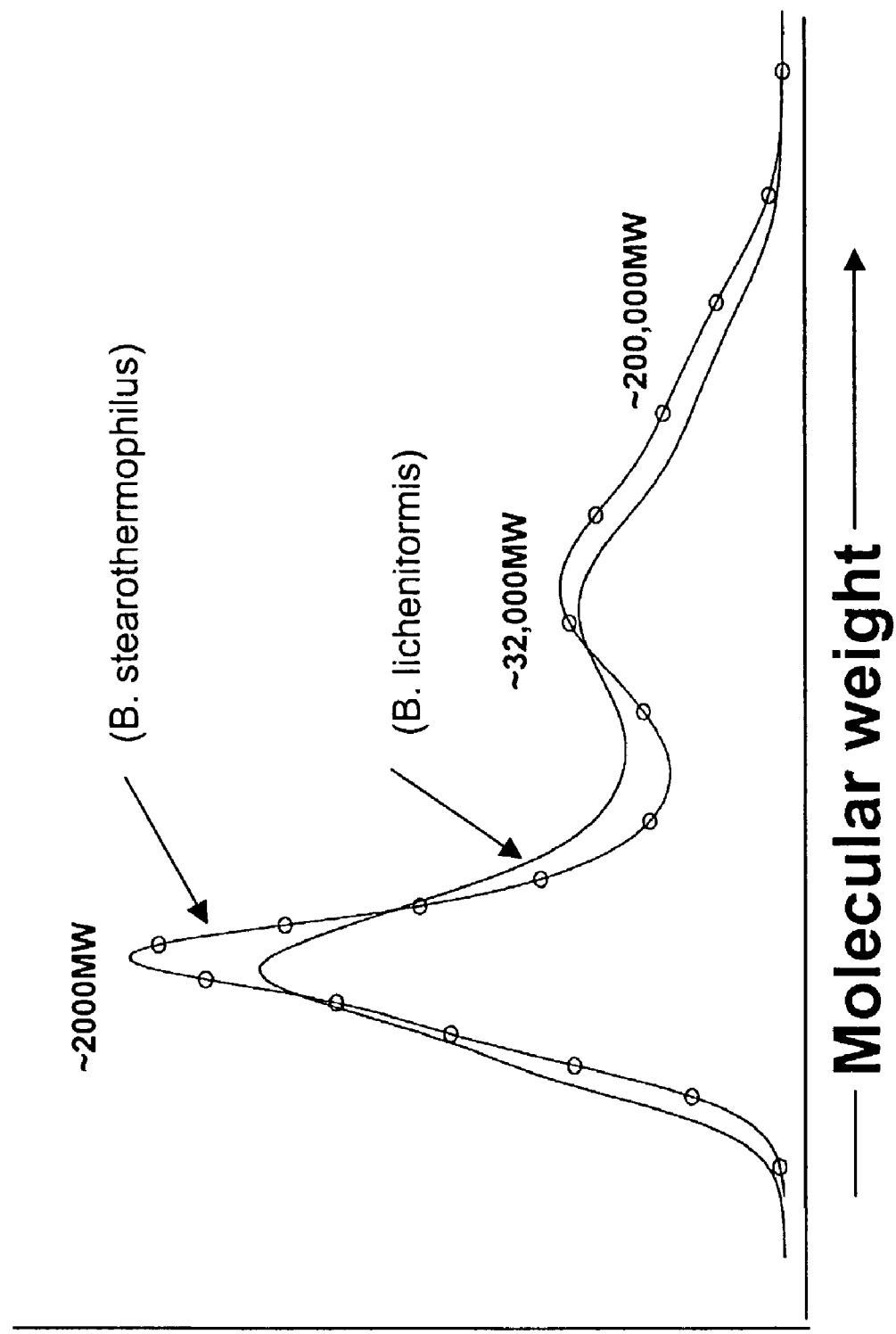
Figure 8:
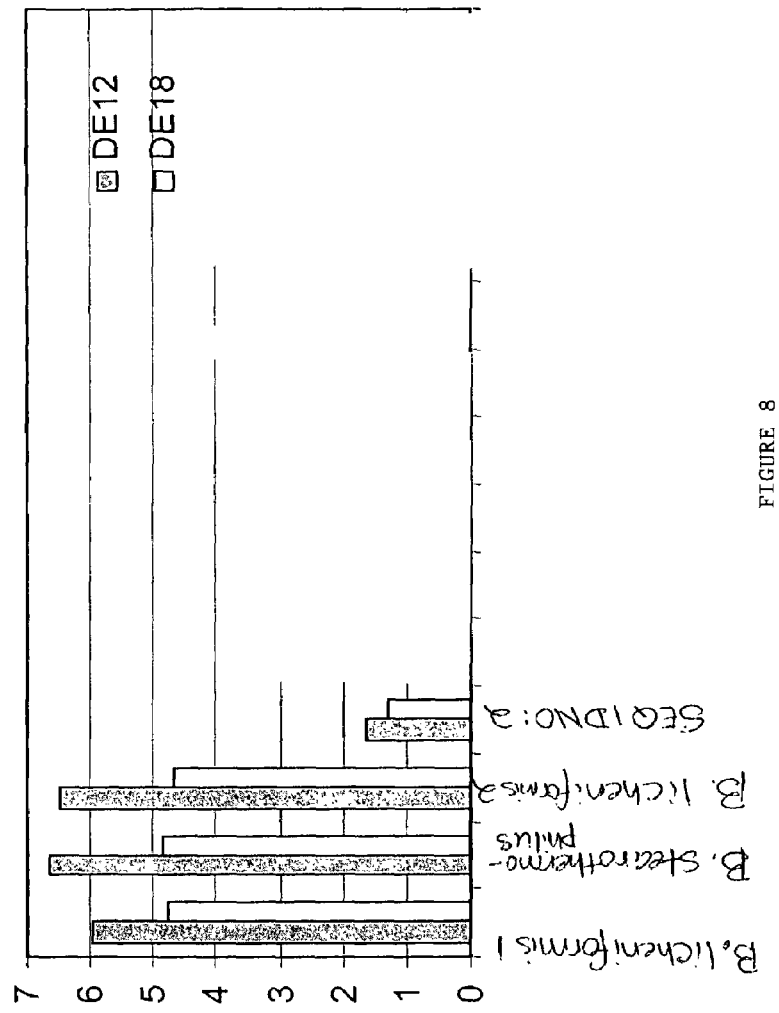
FIG. 8 shows a comparison of oligosaccharide profiles for SEQ ID No: 2 and commercial amylases.

Corn wet milling is a process which produces corn oil, gluten meal, gluten feed and starch. Amylases of the invention, including SEQ ID NO:2, are used in the liquefaction of starch and glucoamylase is used in saccharification, producing glucose. The properties of the amylases of the present invention are unique in that they allow production of liquefied syrups which can be converted to higher dextrose levels than a conventional Bacillus amylase liquefied syrup. As can be seen in FIGS. 6a-6b and in the Examples, the molecular weight profile of liquefied starch produced by commercial amylases derived from *Bacillus licheniformis* and *Bacillus stearothermophilus* exhibit a bimodal distribution with a primary peak at 1000-2000 MW representing approximately 60% of the mass with a secondary peak at 30,000-40,000 MW. In addition, there is a substantial fraction at greater than 100,000 MW. The amylases of the invention exhibit a homogeneous MW distribution centered at 1000-2000 MW with less than 10% of the mass greater than 25,000 MW. The higher MW oligosaccharides are not fully converted to glucose during saccharification. Consequently, the commercial amylases will contain less dextrose than saccharified syrups from the liquefaction process carried out by amylase enzymes of the present invention, such as that represented in SEQ ID NO:2 and functional equivalents thereof.

Maltodextrins are utilized in a wide variety of food and coating applications. Amylases from Archeal sources generate an extremely uniform maltodextrin composition (see also Leveque et al., Enzyme and Microbial Technology 26:3-14, 2000, herein incorporated by reference). The use of the amylases of the invention to liquefy corn starch results in a uniform maltodextrin composition. The liquefaction can be performed at a pH of about 4.5-6.5, and preferably around pH 5.0 and at temperatures of up to 105 degrees C. or higher.

In addition to the benefits demonstrated in saccharification, the liquefied syrups can be carbon treated, spray dried and utilized as food additives, thickeners, low caloric bulking agents, film forming agents, etc. It is anticipated (but not yet proven) that the homogenous molecular weight profile maltodextrins will have performance advantages vs. the bimodal distribution maltodextrins produced by the conventional Baccilus enzymes.

"Liquefaction" or "liquefy" means a process by which starch is converted to shorter chain and less viscous dextrins. Generally, this process involves gelatinization of starch simultaneously with or followed by the addition of alpha amylase. In commercial processes, it is preferred that the granular starch is derived from a source comprising corn, wheat, milo, sorghum, rye or bulgher. However, the present invention applies to any grain starch source which is useful in liquefaction, e.g., any other grain or vegetable source known to produce starch suitable for liquefaction.

"Granular starch" or "starch granules" means a water-insoluble component of edible grains which remains after removal of the hull, fiber, protein, fat, germ, and solubles through the steeping, mechanical cracking, separations, screening, countercurrent rinsing and centrifugation steps typical of the grain wet-milling process. Granular starch comprises intact starch granules containing, almost exclusively, packed starch molecules (i.e., amylopectin and amylose). In corn, the granular starch component comprises about 99% starch; the remaining 1% being comprised of protein, fat, ash, fiber and trace components tightly associated with the granules. The packing structure of granular starch severely retards the ability of .alpha.-amylase to hydrolyze starch. Gelatinization of the starch is utilized to disrupt the granules to form a soluble starch solution and facilitate enzymatic hydrolysis.

"Starch solution" means the water soluble gelatinized starch which results from heating granular starch. Upon heating of the granules to above about 72 degrees C., granular starch dissociates to form an aqueous mixture of loose starch molecules. This mixture comprising, for example, about 75% amylopectin and 25% amylose in yellow dent corn forms a viscous solution in water. In commercial processes to form glucose or fructose, it is the starch solution which is liquefied to form a soluble dextrin solution. "alpha amylase" means an enzymatic activity which cleaves or hydrolyzes the alpha (1-4) glycosidic bond, e.g., that in starch, amylopectin or amylose polymers. Suitable alpha amylases are the naturally occurring alpha amylases as well as recombinant or mutant amylases which are useful in liquefaction of starch. Techniques for producing variant amylases having activity at a pH or temperature, for example, that is different from the wild-type amylase, are included herein.

The temperature range of the liquefaction is generally any liquefaction temperature which is known to be effective in liquefying starch. Preferably, the temperature of the starch is between about 80 degrees C. to about 115 degrees C., more preferably from about 100 degrees C. to about 110 degrees C., and most preferably from about 105 degrees C. to about 108 degrees C.

In one embodiment, the signal sequences of the invention are identified following identification of novel amylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The sequences vary in length from 13 to 36 amino acid residues. Various methods of recognition of signal sequences are known to those of skill in the art. In one embodiment, the peptides are identified by a method referred to as SignalP. SignalP uses a combined neural network which recognizes both signal peptides and their cleavage sites. (Nielsen, H., Engelbrecht, J., Brunalk, S., von Heijne, G., "Identification of prokaryotic and eukaryotic signal peptides and prediction of their cleavage sites." Protein Engineering, vol. 10, no. 1, p. 1-6 (1997), hereby incorporated by reference.) It should be understood that some of the amylases of the invention may not have signal sequences. It may be desirable to include a nucleic acid sequence encoding a signal sequence from one amylase operably linked to a nucleic acid sequence of a different amylase or, optionally, a signal sequence from a non-amylase protein may be desired.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Creighton, T.E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least 104-106 fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an alpha amylase polypeptide, resulting in modification of the structure of the polypeptide, without significantly altering its biological activity. For example, amino- or carboxyl-terminal amino acids that are not required for alpha amylase biological activity can be removed. Modified polypeptide sequences of the invention can be assayed for alpha amylase biological activity by any number of methods, including contacting the modified polypeptide sequence with an alpha amylase substrate and determining whether the modified polypeptide decreases the amount of specific substrate in the assay or increases the bioproducts of the enzymatic reaction of a functional alpha amylase polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an alpha amylase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM™ and any combination thereof. Techniques for producing variant amylases having activity at a pH or temperature, for example, that is different from the wild-type amylase, are included herein.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

In one aspect, the invention includes a method for liquefying a starch containing composition comprising contacting the starch with a polypeptide of the invention (e.g., a purified polypeptide selected from polypeptides having an amino acid sequence selected from the group consisting of: SEQ ID NO:2; variants having at least about 50% homology to at least one of SEQ ID NO:2, over a region of at least about 100 residues, as determined by analysis with a sequence comparison algorithm or by visual inspection; sequences complementary to SEQ ID NO:2; and sequences complementary to variants having at least about 50% homology to SEQ ID NO:2 over a region of at least about 100 residues, as determined by analysis with a sequence comparison algorithm or by visual inspection; and polypeptides having at least 10 consecutive amino acids of a polypeptide having a sequence selected from the group consisting of SEQ ID NO:2). In one preferred embodiment, the polypeptide is set forth in SEQ ID NO:2. The starch may be from a material selected from rice, germinated rice, corn, barley, wheat, legumes and sweet potato. A glucose syrup produced by the method of the invention is included herein and is described in the examples. Such a syrup can be a maltose syrup, a glucose syrup, or a combination thereof. In particular, the syrups produced using the amylases of the invention there is a higher level of DP2 fraction and a higher level of DP3 (maltotriose and/or panose) and less of the greater than DP7 fragments as compared to the syrups produced by commercial enzymes (see Example 5). This is consistent with the liquefaction profile since less of the large fragments are in the invention liquefied syrups (see Example 5).

The invention also provides a method for removing starch containing stains from a material comprising contacting the material with a polypeptide of the invention. In one aspect, the invention provides a method for washing an object comprising contacting the object with a polypeptide of the invention under conditions sufficient for washing. A polypeptide of the invention may be included as a detergent additive for example. The invention also includes a method for textile desizing comprising contacting the textile with a polypeptide of the invention under conditions sufficient for desizing.

The invention also provides a method of reducing the staling of bakery products comprising addition of a polypeptide of the invention to the bakery product, prior to baking.

The invention also provides a method for the treatment of lignocellulosic fibers, wherein the fibers are treated with a polypeptide of the invention, in an amount which is efficient for improving the fiber properties. The invention includes a for enzymatic deinking of recycled paper pulp, wherein the polypeptide is applied in an amount which is efficient for effective deinking of the fiber surface.

Any of the methods described herein include the possibility of the addition of a second alpha amylase or a beta amylase or a combination thereof. Commercial amylases or other enzymes suitable for use in combination with an enzyme of the invention are known to those of skill in the art.

The invention also includes a method of increasing the flow of production fluids from a subterranean formation by removing a viscous, starch-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds.

Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174, herein incorporated by reference in its entirety).

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The alpha amylases of the present invention can be mutagenized in accordance with the methods described herein.

Thus according to one aspect of the invention, the sequences of a plurality of progenitor nucleic acid templates (e.g., polynucleotides of SEQ ID NO:1 nucleic acid sequences) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made, intron-containing gene and a nucleic acid, which serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins through recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid alpha amylases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, such as alpha amylases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases; (b) ester bonds, i.e., amylases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several amylases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;

2) growing the host cell under conditions which promote sequence reorganization resulting in a hybrid polynucleotide in operable linkage;

3) expressing a hybrid polypeptide encoded by the hybrid polynucleotide;

4) screening the hybrid polypeptide under conditions which promote identification of enhanced biological activity; and 5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artifidial chomosomes, yeast plasmids, yeast artificial chromosomes, and any other vectors specific for specific hosts of interest (such as *bacillus, Aspergillus* and *yeast*). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBLUESCRIPT™ plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:

1) The use of vectors only stably maintained when the construct is reduced in complexity.

2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, viron, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acelylated or deacetylated 4'-fluro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl) phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polyp eptides in which a full range of single amino acid substitutions is represented at each amino acid position Gene Site Saturation Mutagenesis™ (GSSM™)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e. a degenerate (N,N,N)n sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of SEQ ID NO:1 nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a SEQ ID NO:1 nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the SEQ ID NO:1 nucleic acid sequences, and sequences substantially identical thereto, may be used to prepare one of the polypeptides of a SEQ ID NO:2 amino acid sequence, and sequences substantially identical thereto, or fragments comprising at least 5, 10, 15, 20, 25, 30, 35, 40, 50, 75, 100, or 150 consecutive amino acids of one of the polypeptides of SEQ ID NO:2 amino acid sequences, and sequences substantially identical thereto.

Accordingly, another aspect of the invention is an isolated nucleic acid which encodes one of the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids of one of the polypeptides of the SEQ ID NO:2 amino acid sequences. The coding sequences of these nucleic acids may be identical to one of the coding sequences of one of the nucleic acids of SEQ ID NO:1 nucleic acid sequences, or a fragment thereof or may be different coding sequences which encode one of the polypeptides of SEQ ID NO:2 amino acid sequences, sequences substantially identical thereto, and fragments having at least 5, 10, 15, 20, 25, 30, 35, 40, 50, 75, 100, or 150 consecutive amino acids of one of the polypeptides of SEQ ID NO:2 amino acid sequences, as a result of the redundancy or degeneracy of the genetic code. The genetic code is well known to those of skill in the art and can be obtained, for example, on page 214 of B. Lewin, Genes VI, Oxford University Press, 1997, the disclosure of which is incorporated herein by reference.

The isolated nucleic acid which encodes one of the polypeptides of SEQ ID NO:2 amino acid sequences, and sequences substantially identical thereto, may include, but is not limited to: only the coding sequence of one of SEQ ID NO:1 nucleic acid sequences, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of SEQ ID NO:1 nucleic acid sequences, and sequences substantially identical thereto, may be mutagenized using conventional techniques, such as site directed mutagenesis, or other techniques familiar to those skilled in the art, to introduce silent changes into the polynucleotides of SEQ ID NO:1 nucleic acid sequences, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of SEQ ID NO:2 amino acid sequences, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of SEQ ID NO:1 nucleic acid sequences, and sequences substantially identical thereto (or the sequences complementary thereto) under conditions of high, moderate, or low stringency as provided herein.

The isolated nucleic acids of SEQ ID NO:1 nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of SEQ ID NO:1 nucleic acid sequences, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. (1997) and Sambrook et al., Molecular Cloning: A Laboratory Manual 2nd Ed., Cold Spring Harbor Laboratory Press (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", PCR Methods and Applications 1:5-16, 1991; E. Fahy et al., "Self-sustained Sequence Replication (3SR): An Isothermal Transcription-based Amplification System Alternative to PCR", PCR Methods and Applications 1:25-33, 1991; and Walker G. T. et al., "Strand Displacement Amplification-an Isothermal in vitro DNA Amplification Technique", Nucleic Acid Research 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an interculator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of SEQ ID NO:1 nucleic acid sequences, and sequences substantially identical thereto, may also be used in chromosome walking procedures to identify clones containing genomic sequences located adjacent to the sequences of SEQ ID NO:1 nucleic acid sequences, and sequences substantially identical thereto. Such methods allow the isolation of genes which encode additional proteins from the host organism.

The isolated nucleic acids of SEQ ID NO:1 nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of SEQ ID NO:1 nucleic acid sequences, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10× Denhardt's, and 0.5 mg/ml polyriboadenylic acid. Approximately 2×10^7 cpm (specific activity 4-9×10^8 cpm/ug) of 32P end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM Na2EDTA) containing 0.5% SDS, followed by a 30 minute wash in fresh 1× SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following formulas:

For probes between 14 and 70 nucleotides in length the melting temperature (Tm) is calculated using the formula: Tm=81.5+16.6(log [Na+])+0.41(fraction G+C)−(600/N) where N is the length of the probe.

If the hybridization is carried out in a solution containing formamide, the melting temperature may be calculated using the equation: Tm=81.5+16.6(log [Na+])+0.41 (fraction G+C)−(0.63% formamide)−(600/N) where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 70%, at least 65%, at least 60%, at least 55%, or at least 50% homology to a nucleic acid sequence selected from the group consisting of one of the sequences of SEQ ID NO:1 nucleic acid sequences, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of SEQ ID NO:1 nucleic acid sequences or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide having the sequence of one of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of SEQ ID NO:1 nucleic acid sequences, and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene.

In some embodiments, the nucleic acid encoding one of the polypeptides of SEQ ID NO:2 amino acid sequences, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2nd Ed., Cold Spring Harbor Laboratory Press (1989), the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, 2nd Ed., Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBLUE-SCRIPT II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as *yeast*, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of SEQ ID NO:2 amino acid sequences, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11-15, 1989) and Caldwell, R. C. & Joyce G. F., PCR Methods Applic., 2:28-33, 1992, the disclosure of which is incorporated herein by reference in its entirety. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747-10751, 1994, the disclosure of which is incorporated herein by reference. Briefly, in such procedures a plurality of nucleic acids to be recombined are digested with DNAse to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548-1552, 1993, the disclosure of which incorporated herein by reference in its entirety. Random and site-directed mutagenesis are described in Arnold, F. H., Current Opinion in Biotechnology, 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of SEQ ID NO:2 amino acid sequences may be variants in which one or more of the amino acid residues of the polypeptides of the SEQ ID NO:2 amino acid sequences are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the SEQ ID NO:2 amino acid sequences includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NO:2 amino acid sequences, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of SEQ ID NO:2 amino acid sequences, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO:2 amino acid sequences, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO:2 amino acid sequences, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of SEQ ID NO:2 amino acid sequences, and sequences substantially identical thereto, which retain the enzymatic function of the polypeptides of SEQ ID NO:2 amino acid sequences, and sequences substantially identical thereto. For example the fragments or variants of said polypeptides, may be used to catalyze biochemical reactions, which indicate that the fragment or variant retains the enzymatic activity of the polypeptides in the SEQ ID NO:2 amino acid sequences.

The assay for determining if fragments of variants retain the enzymatic activity of the polypeptides of SEQ ID NO:2 amino acid sequences, and sequences substantially identical thereto includes the steps of: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of SEQ ID NO:2 amino acid sequences, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of SEQ ID NO:2 amino acid sequences, and sequences substantially identical thereto or polynucleotides encoding such polypeptides for hydrolyzing glycosidic linkages. In such procedures, a substance containing a glycosidic linkage (e.g., a starch) is contacted with one of the polypeptides of SEQ ID NO:2 amino acid sequences, or sequences substantially identical thereto under conditions which facilitate the hydrolysis of the glycosidic linkage.

The polypeptides of SEQ ID NO:2 amino acid sequences, and sequences substantially identical thereto or fragments comprising at least 5, 10, 15, 20, 25, 30, 35, 40, 50, 75, 100, or 150 consecutive amino acids thereof, may also be used in the liquefaction and saccharification of starch. Using the polypeptides or fragments thereof of this invention, liquefaction may be carried out at a lower pH than with previous enzymes. In one embodiment, liquefaction is performed at a pH of 4.5. Additionally, the polypeptides or fragments thereof of this invention are less calcium dependent than enzymes previously used in these processes. In liquefaction amylases are used to hydrolyze starch. In a preferred embodiment, the polypeptides or fragments thereof of this invention are thermostable at 90-95° C.

The polypeptides of SEQ ID NO:2 amino acid sequences, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of SEQ ID NO:2 amino acid sequences, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of SEQ ID NO:2 amino acid sequences, and sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", Methods in Enzymology, Vol 160, pp. 87-116, which is hereby incorporated by reference in its entirety.

As used herein the term "nucleic acid sequence as set forth in SEQ ID NO.: 1" encompasses the nucleotide sequences of SEQ ID NO:1 nucleic acid sequences, and sequences substantially identical thereto, as well as sequences homologous to SEQ ID NO:1 nucleic acid sequences, and fragments thereof and sequences complementary to all of the preceding sequences. The fragments include portions of SEQ ID NO.: 1, comprising at least 10, 15, 20, 25, 30, 35, 40, 50, 75, 100, 150, 200, 300, 400, or 500 consecutive nucleotides of SEQ ID NO:1 nucleic acid sequences, and sequences substantially identical thereto. Homologous sequences and fragments of SEQ ID NO:1 nucleic acid sequences, and sequences substantially identical thereto, refer to a sequence having at least 99%, 98%, 97%, 96%, 95%, 90%, 85%, 80%, 75%, 70%, 65%, 60%, 55% or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the SEQ ID NO:1 nucleic acid sequences. The homologous sequences may be obtained using any of the procedures described herein or may result from the correction of a sequencing error. It will be appreciated that the nucleic acid sequences as set forth in SEQ ID NO:1 nucleic acid sequences, and sequences substantially identical thereto, can be represented in the traditional single character format (See the inside back cover of Stryer, Lubert. Biochemistry, 3rd Ed., W.H Freeman & Co., New York.) or in any other format which records the identity of the nucleotides in a sequence.

As used herein the term "a polypeptide sequence as set forth in SEQ ID NO:2" encompasses the polypeptide sequence of SEQ ID NO:2 amino acid sequences, and sequences substantially identical thereto, which are encoded by a sequence as set forth in SEQ ID NO:2, polypeptide sequences homologous to the polypeptides of SEQ ID NO:2 amino acid sequences, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75%, 70%, 65%, 60%, 55% or 50% homology to one of the polypeptide sequences of the SEQ ID NO:2 amino acid sequences. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of SEQ ID NO:2 amino acid sequences, and sequences substantially identical thereto. It will be appreciated that the polypeptide codes as set forth in SEQ ID NO:2 amino acid sequences, and sequences substantially identical thereto, can be represented in the traditional single character format or three letter format (See the inside back cover of Stryer, Lubert. Biochemistry, 3rd Ed., W.H Freeman & Co., New York.) or in any other format which relates the identity of the polypeptides in a sequence.

It will be appreciated by those skilled in the art that a nucleic acid sequence as set forth in SEQ ID No.: 1 and a polypeptide sequence as set forth in SEQ ID No.: 2 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in SEQ ID NO:1 nucleic acid sequences, and sequences substantially identical thereto, one or more of the polypeptide sequences as set forth in SEQ ID NO:2 amino acid sequences, and sequences substantially identical thereto. Another aspect of the invention is a computer readable medium having recorded thereon at least 2, 5, 10, 15, or 20 nucleic acid sequences as set forth in SEQ ID NO:1 nucleic acid sequences, and sequences substantially identical thereto.

Another aspect of the invention is a computer readable medium having recorded thereon one or more of the nucleic acid sequences as set forth in SEQ ID NO:1 nucleic acid sequences, and sequences substantially identical thereto. Another aspect of the invention is a computer readable medium having recorded thereon one or more of the polypeptide sequences as set forth in SEQ ID NO:2 amino acid sequences, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 1:
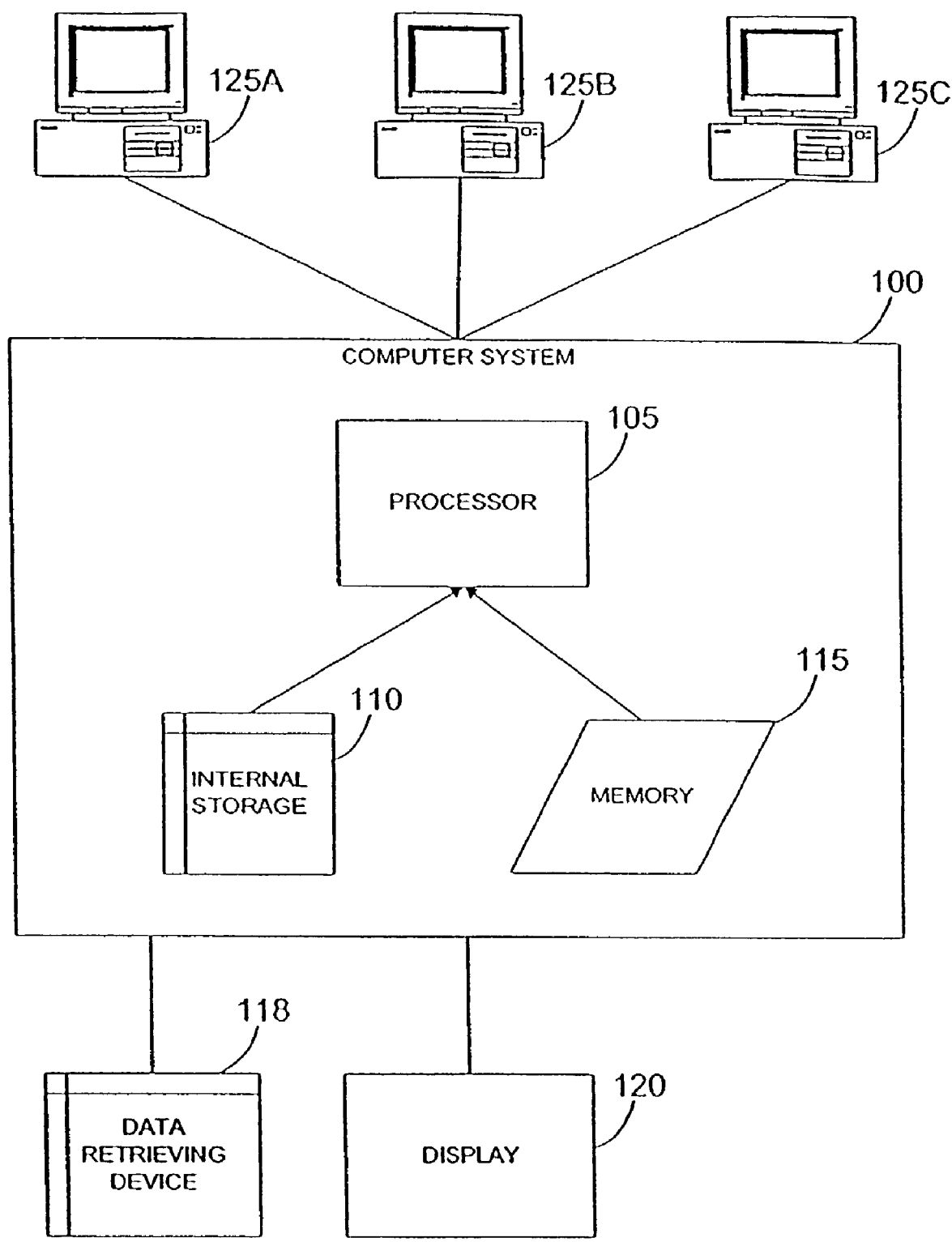
FIG. 1 is a block diagram of a computer system.

Embodiments of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components, and data storage components used to analyze a nucleotide sequence of a nucleic acid sequence as set forth in SEQ ID NO:1 nucleic acid sequences, and sequences substantially identical thereto, or a polypeptide sequence as set forth in the SEQ ID NO:2 amino acid sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for sunilarity method of person & Lipman, Proc. Nat'l. Acad. Sci. USA 85:2444, 1988, by computerized implementations of these algoritluns (GAP, BESTFIT, FASTA, and TEASTA in the Wisconsin Genetics Software Package, Genetics Computer Group, 575 Science Dr., Madison, Wis.), or by manual alignment and visual inspection. Other algorithms for detenriining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V. CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristeusky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases arc available, for example, a substantial portion of the human genome is available as part of the Human Genome Sequencing Project (Gibbs, 1995). At least twenty-one other genomes have already been sequenced, including, for example, *M. genitalium* (Fraser et at., 1995), *M. jannaschii* (Bult et al., 1996), *H. influenzae* (Fleischmann et al., 1995), *E. coli* (Blattner et al, 1997), and *yeast* (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at, supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are baited when: the cumulative aligmnent score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

Figure 2:
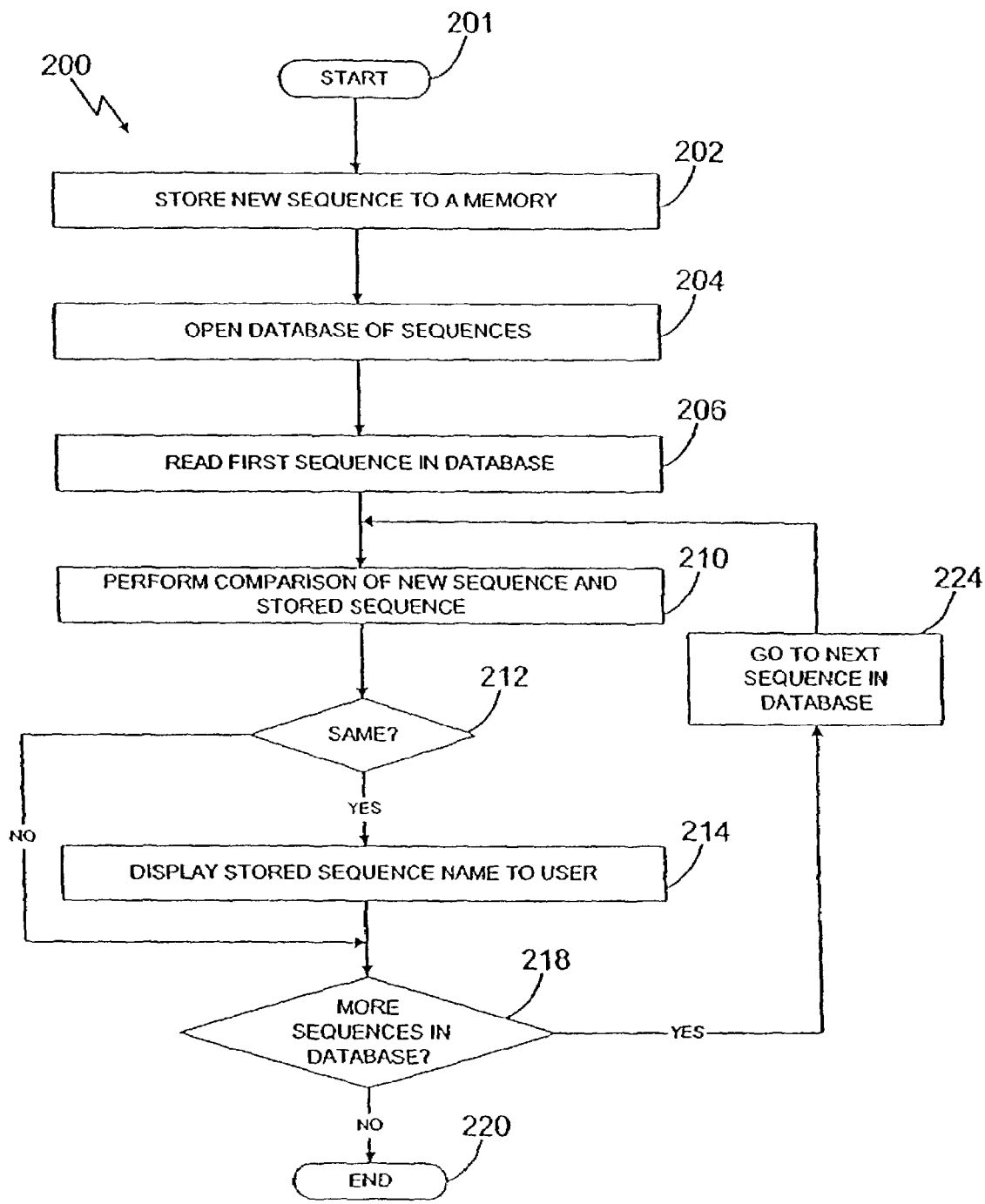
FIG. 2 is a flow diagram illustrating one embodiment of a process for comparing a new nucleotide or protein sequence with a database of sequences in order to determine the homology levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, a data storage device having retrievably stored thereon reference nucleotide sequences or polypeptide sequences to be compared to a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, and a sequence comparer for conducting the comparison. The sequence comparer may indicate a homology level between the sequences compared or identify structural motifs in the above described nucleic acid code of SEQ ID NO:1 nucleic acid sequences, and sequences substantially identical thereto, or a polypeptide sequence as set forth in SEQ ID NO:2 amino acid sequences, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in SEQ ID NO:1 nucleic acid sequences, and sequences substantially identical thereto, or the polypeptide sequences as set forth in SEQ ID NO:2 amino acid sequences, and sequences substantially identical thereto.

Another aspect of the invention is a method for determining the level of homology between a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the SEQ ID NO:1 nucleic acid sequences, or the polypeptide sequences as set forth in the SEQ ID NO:2 amino acid sequences through use of the computer program and determining homology between the nucleic acid codes or polypeptide codes and reference nucleotide sequences or polypeptide sequences.

Figure 3:
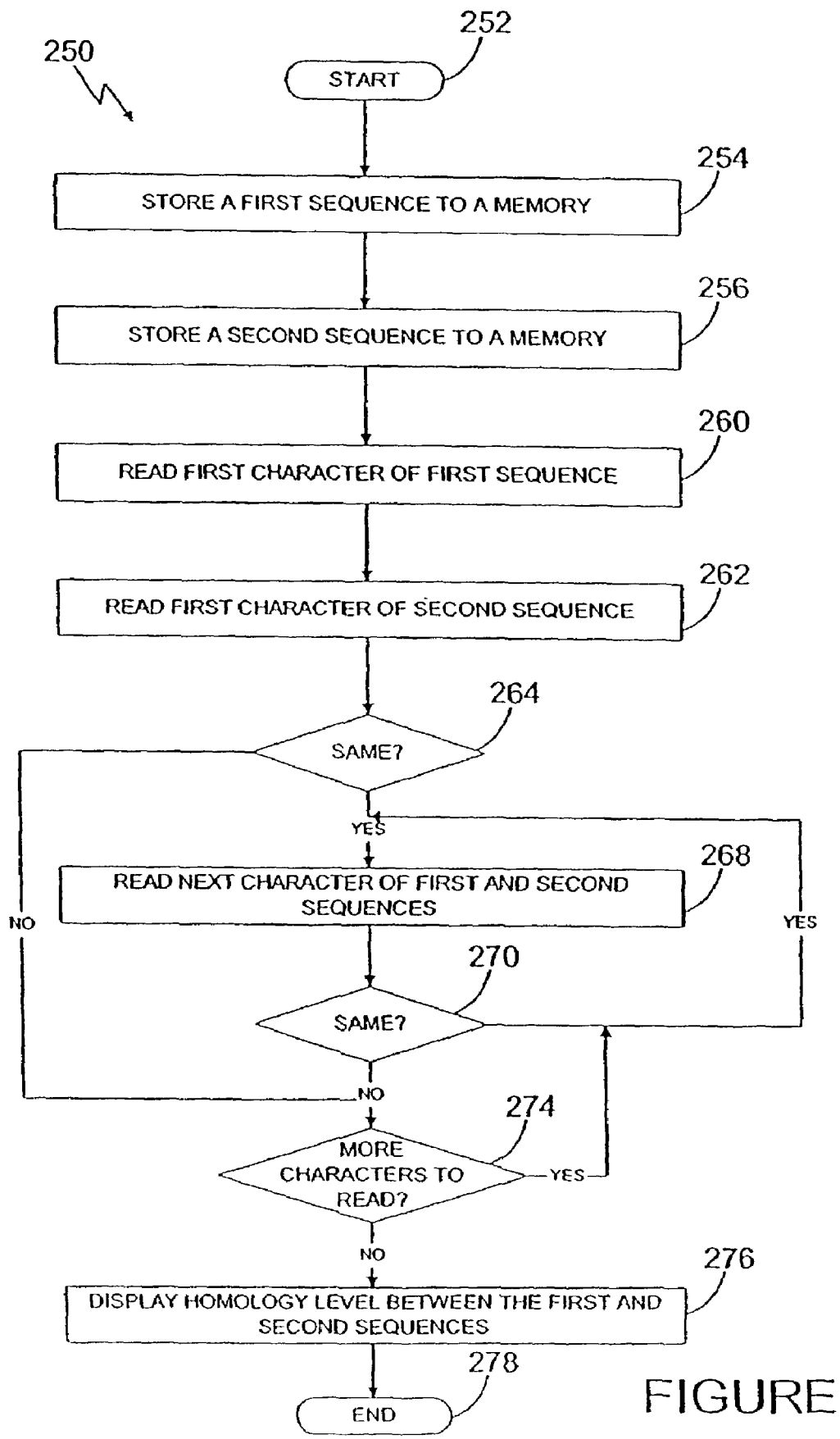
FIG. 3 is a flow diagram illustrating one embodiment of a process in a computer for determining whether two sequences are homologous.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of SEQ ID NO:1 nucleic acid sequences, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in SEQ ID NO:1 nucleic acid sequences, and sequences substantially identical thereto. In one embodiment, the computer program may be a program which determines whether a nucleic acid sequence as set forth in SEQ ID NO:1 nucleic acid sequences, and sequences substantially identical thereto, contains a single nucleotide polymorphism (SNP) with respect to a reference nucleotide sequence.

Accordingly, another aspect of the invention is a method for determining whether a nucleic acid sequence as set forth in SEQ ID NO:1 nucleic acid sequences, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in SEQ ID NO:1 nucleic acid sequences, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the SEQ ID NO:1 nucleic acid sequences or a polypeptide sequence as set forth in SEQ ID NO:2 amino acid sequences, and sequences substantially identical thereto.

An "identifier" refers to one or more programs which identifies certain features within a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto. In one embodiment, the identifier may comprise a program which identifies an open reading frame in a nucleic acid sequence as set forth in SEQ ID NO:1 nucleic acid sequences, and sequences substantially identical thereto.

Figure 4:
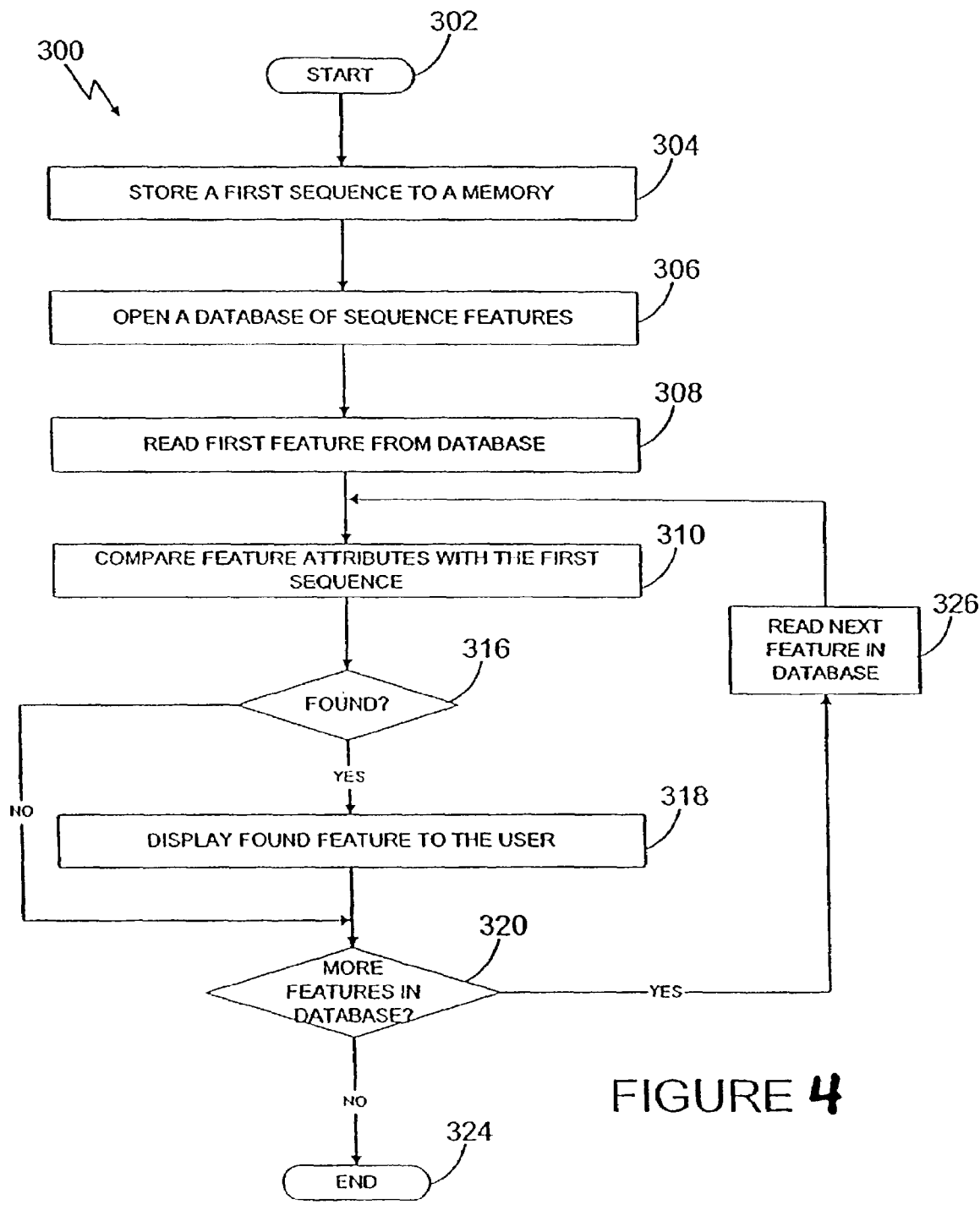
FIG. 4 is a flow diagram illustrating one embodiment of an identifier process 300 for detecting the presence of a feature in a sequence.

FIG. 4 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com). Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in SEQ ID NO:1 nucleic acid sequences, and sequences substantially identical thereto, or the polypeptide sequences as set forth in SEQ ID NO:2 amino acid sequences, and sequences substantially identical thereto, through the use of the computer program and identifying features within the nucleic acid codes or polypeptide codes with the computer program.

A nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, may be stored and manipulated in a variety of data processor programs in a variety of formats. For example, a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto, may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in SEQ ID NO:1 nucleic acid sequences, and sequences substantially identical thereto, or a polypeptide sequence as set forth in SEQ ID NO:2 amino acid sequences, and sequences substantially identical thereto. The following list is intended not to limit the invention but to provide guidance to programs and databases which are useful with the nucleic acid sequences as set forth in SEQ ID NO:1 nucleic acid sequences, and sequences substantially identical thereto, or the polypeptide sequences as set forth in SEQ ID NO:2 amino acid sequences, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular embodiment, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library, and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

The invention will be further described with reference to the following examples; however, it is to be understood that the invention is not limited to such examples.

EXAMPLES

Example 1

Identification and Characterization of Thermostable α-Amylases

The present example shows the identification of novel acid amylases. The screening program was carried out under neutral and low pH conditions. DNA libraries generated from low pH samples were targeted for discovery. This effort afforded the discovery of hundreds of clones having the ability to degrade starch. DNA sequence and bioinformatic analyses classified many of these genes as previously unidentified amylases.

Biochemical Studies

Biochemical analysis of the amylase genomic clones showed that many had pH optima of less than pH 6. Lysates of these genomic clones were tested for thermal tolerance by incubation at 70° C., 80° C., 90° C. or 100° C. for 10 minutes and measurement of residual activity at pH 4.5. Those clones retaining >50% activity after heat treatment at 80° C. were chosen for further analysis. These clones were incubated at 90° C. for 10 minutes at pH 6.0 and 4.5 and tested for residual activity at pH 4.5. A number of clones retained >40% of their activity following this treatment. For comparative purposes, residual activity of an evolved amylase, SEQ ID NO:2, was equivalent to the best of the second-generation enzymes; the specific activity of SEQ ID NO:2 was greater.

Thermal activity of the clones with residual activity after heat treatment at 90° C. at pH 4.5 was measured at room temperature, 70° C. and 90° C. at pH 4.5. Table 1 shows that the hydrolysis rates of SEQ ID NO.: 3 (*B. stearothermophilus* amylase) and SEQ ID NO.: 4 (*B. licheniformis* amylase) decrease at higher temperatures, whereas the rate for SEQ ID NO.: 5 continues to increase as the temperature is raised to 70° C. and only reduces by around 50% at 90° C.

Candidate Evaluation

Based on residual activity at pH 4.5 after a 90° C. heat treatment, specific activity and rate of starch hydrolysis at 90° C. when compared with *B. licheniformis* amylase, SEQ ID NO.: 5 is compared with the evolved amylase SEQ ID NO:2 in a starch liquefaction assay.

TABLE 1

Rates of dye labeled starch hydrolysis (relative fluorescence units/s) of three genomic clones at pH 4.5 and 3 different temperatures.

| | Room temperature | 70° C. | 90° |
|---|---|---|---|
| SEQ ID NO.: 3[1] | 1.25 | 1.43 | 0.33 |
| SEQ ID NO.: 4[2] | 3.3 | 1.9 | 0.39 |
| SEQ ID NO.: 5 | 1.9 | 47 | 19 |

[1]*B. stearothermophilus* amylase,
[2]*B. licheniformis* amylase

Example 2

Amylase Activity Assay: BCA Reducing Ends Assay

1. Prepare 2 substrate solutions, as follows:
    a) 2% soluble starch (potato) pH 8 solution by dissolving 2 gm potato starch in 100 ml 100 mM sodium phosphate pH 8).
    b) 2% soluble starch (potato) pH 10 solution by dissolving 2 gm potato starch in 100 ml 100 mM sodium carbonate.

Heat both solutions in a boiling water bath, while mixing, for 30-40 minutes until starch dissolves.
2. Prepare Solution A from 64 mg/ml sodium carbonate monohydrate, 24 mg/ml sodium bicarbonate and 1.95 mg/ml BCA (4,4'-dicarboxy-2,2'-biquinoline disodium salt (Sigma Chemical cat #D-8284). Added above to dH2O.
3. Prepare solution B by combining 1.24 mg/ml cupric sulfate pentahydrate and 1.26 mg/ml L-serine. Add mixture to to dH2O.
4. Prepare a working reagent of a 1:1 ration of solutions A and B.
5. Prepare a Maltose standard solution of 10 mM Maltose in dH2O, where the 10 mM maltose is combined in 2% soluble starch at desired pH to a final concentration of 0, 100, 200, 300, 400, 600 μM. The standard curve will be generated for each set of time-points. Since the curve is determined by adding 10 ul of the standards to the working reagent it works out to 0, 1, 2, 3, 4, 6 nmole maltose.
6. Aliquot 1 ml of substrate solution into microcentrifuge tubes, equilibrate to desired temperature (5 min) in heat block or heated water bath. Add 50 ul of enzyme solution to the inside of the tube lid.
7. While solution is equilibrating mix 5 ml of both solution A & B. Aliquot 100 ul to 96 well PCR plate. Set plate on ice.
8. After 5 minute temperature equilibration, close lid on tubes, invert and vortex 3 times. Immediately aliquot 10 ul into plate as t=0 (zero time point). Leave enzyme mixture in heat block and aliquot 10 ul at each desired time point (e.g. 0, 5, 10, 15, 20, 30 minutes).
9. Ensure that 12 wells are left empty (only working reagent aliquotted) for the addition of 10 ul of standards, for the standard curve.
10. When all time points are collected and standards are added, cover plate and heated to 80° C. for 35 min. Cool plate on ice for 10 min. Add 100 ul H2O to all wells. Mix and aliquot 100 ul into flat bottomed 96-well plate and read absorbance at 560 nm.
11. Zero each sample's time points against its own t=0 (subtract the average t=0 A560 value from other average A560 values). Convert the $A^{560}_{(experimental)}$ to umole (Divide $A^{560}_{(experimental)}$ by the slope of the standard curve (A560/umole). Generate a slope of the time points and the umole (in umole/min), multiply by 100 (as the umole value only accounts for the 10 ul used in the assay, not the amount made in the 1 ml rxn). To get the specific activity divide the slope (in umole/min) by the mg of protein. All points should be done at a minimum in duplicate with three being best. An example standard curve is set forth in FIG. 5.

TABLE 2

| | | Sample data: | | | | |
|---|---|---|---|---|---|---|
| Clone | Dilution | Minutes | A560-1 | A560-2 | Avg A 560 | Zeroed A 560 | (A560exp/std slope) umole |
| ENZ | 50 | 0 | 0.1711 | 0.1736 | 0.17235 | 0 | 0.0000 |
| | | 5 | 0.2104 | 0.2165 | 0.21345 | 0.0411 | 0.0005 |
| | | 10 | 0.2492 | 0.2481 | 0.24865 | 0.0763 | 0.0009 |

TABLE 2-continued

Sample data:

| Clone | Dilution | Minutes | A560-1 | A560-2 | Avg A 560 | Zeroed A 560 | (A560exp/ std slope) umole |
|---|---|---|---|---|---|---|---|
| | | 15 | 0.2984 | 0.2882 | 0.2933 | 0.12095 | 0.0014 |
| | | 20 | 0.3355 | 0.3409 | 0.3382 | 0.16585 | 0.0020 |
| | | 30 | 0.3942 | 0.3805 | 0.38735 | 0.215 | 0.0026 |
| | | 40 | 0.4501 | 0.4412 | 0.44565 | 0.2733 | 0.0033 |

Example 3

Screening for α-Amylase Activity

The number of plaques screened, per plate, should be approximately 10,000 pfu's. For each DNA library: at least 50,000 plaques per isolated library and 200,000 plaques per non-isolated library should be screened depending upon the pfu titer for the λ Zap Express amplified lysate.

Titer Determination of Lambda Library
1) μL of Lambda Zap Express amplified library stock added to 600 μL $E.$ $coli$ MRF' cells ($OD_{600}$=1.0). To dilute MRF' stock, 10 mM $MgSO_4$ is used.
2) Incubate at 37° C. for 15 minutes.
3) Transfer suspension to 5-6 mL of NZY top agar at 50° C. and gently mix.
4) Immediately pour agar solution onto large (150 mm) NZY media plate.
5) Allow top agar to solidify completely (approximately 30 minutes), then invert plate.
6) Incubate the plate at 39° C. for 8-12 hours.
7) Number of plaques is approximated. Phage titer determined to give 10,000 pfu/plate. Dilute an aliquot of Library phage with SM buffer if needed.

Substrate Screening
1) Lambda Zap Express (50,000 pfu) from amplified library added to 600 μL of $E.$ $coli$ MRF' cells (OD600=1.0). For non-environment libraries, prepare 4 tubes (50,000 pfu per tube).
2) Incubate at 37° C. for 15 minutes.
3) While phage/cell suspension are incubating, 1.0 mL of red starch substrate (1.2% w/v) is added to 6.0 mL NZY top agar at 50° C. and mixed thoroughly. Keep solution at 50° C. until needed.
4) Transfer ⅕ (10,000 pfu) of the cell suspension to substrate/top agar solution and gently mixed.
5) Solution is immediately poured onto large (150 mm) NZY media plate.
6) Allow top agar to solidify completely (approximately 30 minutes), then invert plate.
7) Repeat procedures 4-6 4 times for the rest of the cell suspension (⅕ of the suspension each time).
8) Incubate plates at 39° C. for 8-12 hours.
9) Plate observed for clearing zones (halos) around plaques.
10) Plaques with halos are cored out of agar and transferred to a sterile micro tube. A large bore 200 μL pipette tip works well to remove (core) the agar plug containing the desired plaque.
11) Phages are re-suspended in 500 μL SM buffer. 20 μL Chloroform is added to inhibit any further cell growth.
12) Pure phage suspension is incubated at room temperature for 4 hours or overnight before next step.

Isolation of Pure Clones
1) 10 μL of re-suspended phage suspension is added to 500 μL of $E.$ $coli$ MRF' cells (OD600=1.0).
2) Incubate at 37° C. for 15 minutes.
3) While phage/cell suspension is incubating, 1 mL of red starch substrate (1.2% w/v) is added to 6.0 mL NZY top agar at 50° C. and mixed thoroughly. Keep solution at 50° C. until needed.
4) Cell suspension is transferred to substrate/top agar solution and gently mixed.
5) Solution is immediately poured onto large (150 mm) NZY media plate.
6) Allow top agar to solidify completely (approximately 30 minutes), then invert plate.
7) Plate incubated at 39° C. for 8-12 hours.
8) Plate observed for a clearing zone (halo) around a single plaque (pure clone). If a single plaque cannot be isolated, adjust titer and re-plate phage suspension.
9) Single plaque with halo is cored out of agar and transferred to a sterile micro tube. A large bore 200 μL pipette tip works well to remove (core) the agar plug containing the desired plaque. To amplify the titer, core 5 single active plaques into a micro tube.
10) Phages are re-suspended in 500 μL SM buffer. 20 μL Chloroform is added to inhibit any further cell growth.
11) Pure phage suspension is incubated at room temperature for 4 hours or overnight before next step. The pure phage suspension is stored at −80° C. by adding DMSO into the phage suspension (7% v/v).

Excision of Pure Clone
1) 100 μL of pure phage suspension is added to 200 μL $E.$ $coli$ MRF' cells (OD600=1.0). To this, 1.0 μL of ExAssist helper phage (>1×106 pfu/mL;Stratagene) is added. Use 2059 Falcon tube for excision.
2) Suspension is incubated at 37° C. for 15 minutes.
3) 3.0 mL of 2×YT media is added to cell suspension.
4) Incubate at 30° C. for at least 6 hours or overnight while shaking.
5) Tube transferred to 70° C. for 20 minutes. The phagemid suspension can be stored at 4° C. for 1 to 2 months.
6) 100 μL of phagemid suspension transferred to a micro tube containing 200 μL of $E.$ $coli$ Exp 505 cells (OD600=1.0).
7) Suspension incubated at 37° C. for 15 minutes.
8) 300 μL of SOB is added to the suspension.
9) Suspension is incubated at 37° C. for 30 to 45 minutes.
10) 100 μL of suspension is transferred to a small (90 mm) LB media plate containing Kanamycin (LB media with Kanamycin 50 μg/mL) for Zap Express DNA libraries or Ampicillin (LB media with Kanamycin 100 μg/mL) for Zap II DNA libraries.
11) The rest of suspension is transferred to another small LB media plate.
12) Use sterile glass beads to evenly distribute suspension on the plate.
13) Plates are incubated at 30° C. for 12 to 24 hours.
14) Plate observed for colonies.
15) Inoculate single colony into LB liquid media containing suitable antibiotic and incubate at 30° C. for 12 to 24 hours.
16) Glycerol stock can be prepared by adding 80% glycerol into liquid culture (15% v/v) and stored at −80° C.

Activity Verification
1) 50 μL of liquid culture is transferred to a micro tube. Add 500 μL of 8% pH7 Amylopectin Azure into the same tube. Prepare 2 tubes for each clone.

2) Activity is tested at 50° C. for 3 hours and overnight. Use pH 7 buffer as control.
3) Cool the test specimen at ice-water bath for 5 minutes.
4) Add 750 μL of Ethaqnol and mixed thoroughly.
5) Centrifuge at 13000 rpm (16000 g's) for 5 minutes.
6) Measure OD of the supernatant at 595 nm.

RFLP Analysis 1) 1.0 mL of liquid culture is transferred to a sterile micro tube.
2) Centrifuge at 13200 rpm (16000 g's) for 1 minute.
3) Discard the supernatant. Add another 1.0 mL of liquid culture into the same sterile micro tube.
4) Centrifuge at 13200 rpm (16000 g's) for 1 minute.
5) Discard the supernatant.
6) Follow QlAprep spin mini kit protocol for plasmid isolation.
7) Check DNA concentration using BioPhotometer.
8) Use Sac I and Kpn I for first double digestion. Incubate at 37° C. for 1 hour.
9) Use Pst I and Xho I for second double digestion. Incubate at 37° C. for 1 hour.
10) Add Loading dye into the digested sample.
11) Run the digested sample on a 1.0% agarose gel for 1-1.5 hours at 120 volts.
12) View gel with gel imager. All clones with a different digest pattern will be sent for sequence analysis.

Example 4

Assay for Amylases

Preparation of Host Cultures

1. Start an overnight culture of XL1-Blue MRF' host cells. Use a single colony from a streak plate to inoculate 10 mL LB supplemented with 20 ug/mL tetracycline. Grow overnight culture shaking at 37° C. for at least 16 hours.
2. Using aseptic technique, inoculate a fresh 100 mL of $LB_{Tet}$ day culture with XL1-Blue MRF' host from the overnight $LB_{Tet}$ culture.
3. Grow in a 37° C. shaker until the OD reaches 0.75-1.0.
4. Pellet host cells at 1000×g for 10 minutes and gently resuspend in 10 mM $MgSO_4$ at OD5.
5. Dilute a small amount of host cells to OD1 for use in titering and pintooling.
6. Host preparations can be used for up to 1 week when stored on ice or at 4° C.
   Comments
   To shorten growth time for the day culture, use ½× the usual Tet concentration in LB (½×=10 ug/mL), or omit the antibiotic altogether.
   Do not use NZY when selecting with Tetracycline. The high $Mg^{++}$ concentration in NZY medium renders Tet inactive.

Titering Lambda Libraries

7. Placed three sterile microfuge tubes in a rack.
8. Aliquoted 995 uL prepared host cells in one tube and 45 uL prepared OD1 host cells into each of the two remaining tubes.
9. Added 5 uL of lambda library to the tube containing 995 uL host cells and mixed by vortexing. This resulted in a dilution factor of 200.
10. Prepared ½,000 and ½0,000 dilutions by consecutively adding 5 uL of previous dilution to the remaining two tubes containing 45 uL prepared host cells. Mixed by vortexing after each dilution was made.
11. Phage allowed to adsorb to host by incubating at 37° C. for 15 minutes.
12. Meanwhile, pipetted 100 uL of prepared OD1 host cells to each of three Falcon 2059 tubes.
13. Added 5 uL of each dilution to a separate 2059 tube containing host cells.
14. Plated each by adding 3 mL top agar to each tube and quickly pouring over 90 mm NZY plates. Ensured a smooth, even distribution before the top agar hardens.
15. Inverted plates and incubated at 37° C. overnight.
16. Counted plaques and calculated titer of the library stock (in plaque forming units (pfu) per uL).

1.

Lambda Microtiter Screening For Amylases
Preparation
Prepare a sufficient amount of XL1-Blue MRF' host culture, as described above, for the amount of screening planned.

1. Autoclave several bottles compatible with the QFill2 dispenser. These are the wide-mouth Corning bottles, 250 mL containing a sealing ring around the lip.
2. Make sure there are sufficient amounts of plates, top agar, BODIPY starch, red starch solution, etc. available for the screen.
3. Schedule the Day 2 robot run with a representative from Automation.

Day 1

1. Label the 1536-well plates (black) with library screen and plate number. Tough-Tags™ tube stickers, cut in half width-wise, are ideal for labeling 1536 well plates.
2. Calculate volumes of library, host cells and NZY medium necessary for the screen. This is easily done with an Excel spreadsheet.
3. Combine the calculated volumes of lambda library and OD5 host cells in a sterile 250 mL wide-mouth Corning bottle (containing a sealing ring).
4. Allow adsorption to occur at 37° C. for 15 minutes.
5. Add the calculated volume of NZY medium and mix well. This is referred to as the cell-phage-medium suspension.
6. Perform a concomitant titer by combining 50 uL of the cell-phage-medium suspension with 250 uL of OD1 host cells in a Falcon 2059 tube, then plating with 9 mL of top agar onto a 150 mm NZY plate. Incubate concomitant titer plate at 37° C. overnight.
7. Load the dispenser with the remainder of the suspension and array each labeled 1536-well plate at 4 uL per well. If the dispenser leaves air bubbles in some wells, they can be removed by centrifuging the plates at 200×g for 1 minute.
8. Add 0.5 uL of positive control phage to well position AD46 of at least two of the assay plates. Use a strong amylase-positive lambda clone for this purpose.
9. Incubate assay plates at 37° C. overnight in a humidified (≧95%) incubator.

Day2

17. Count the pfu on the concomitant titer plate and determine the average seed density per well (in pfu per well).
18. Pintool at least 2 plates of each library screen (preferably the 2 containing positive controls) as follows:
    a) Prepare 2 host lawn plates to act as a surface on which to pintool: combine 250 uL of OD1 host cells with 2 mL 2% red starch and plate with 9 mL top agar onto 150 mm NZY plates. Hold each plate as level as possible as the top agar solidifies in order to produce an even hue of red across the plate.
  b) Using a twice flame-sterilized 1536 position pintool, replicate at least 2 of the screening plates onto the host lawn plates.
  c) Place the pintooled recipient plates in a laminar flow hood with the lids off for about 15-30 minutes (to vent off excess moisture).
  d) Replace the lids and incubate inverted at 37° C. overnight.
19. Prepare the 2× BODIPY starch substrate buffer as follows:
  a) Calculate the total volume of 2× substrate buffer solution needed for all screening plates at 4 uL per well (including any extra deadspace volume required by the dispenser) and measure this amount of 100 mM CAPS pH 10.4 into a vessel appropriate for the dispenser used.
  b) Retrieve enough 0.5 mg tubes of BODIPY starch to produce the required volume of 2× substrate buffer [calculated in step a) above] at a final concentration of 20-30 ug/mL.
  c) Dissolve each 0.5 mg tube in 50 uL DMSO at room temperature, protected from light, with frequent vortexing. This takes more than 15 minutes; some production lots of BODIPY starch dissolve better than others.
  d) Add 50 uL 100 mM CAPS buffer pH 10.4 to each tube and mix by vortexing.
  e) Pool the contents of all tubes and remove any undissolved aggregates by centrifuging for 1 minute at maximum speed in a microfuge.
  f) Add the supernatant to the rest of the 100 mM CAPS buffer measured in step a) above.
  g) Protect the 2× substrate buffer from light by wrapping in foil.
20. Take plates and substrate buffer to the automation room and program the robot with the following parameters:
  a) dispense 4 uL substrate buffer per well
  b) $1^{st}$ read at 1 hour post-substrate, $2^{nd}$ read at 9 hours, and third read at 17 hours; with 37° C. incubation between reads
  c) excitation filter: 485 nm; emission filter: 535 nm
  d) set the Spectrafluor gain at 70.
  e) ensure that the incubator used will protect assay plates from light.

Day 3
1. Check pintooled plates for clearings in the bacterial lawn at all positions corresponding to wells on the associated assay plate. Also check for clearings in the red starch in any of the pin positions. If plates containing positive controls were used for pintooling, you should be able to see a large clearing zone in the red background. Be wary of contaminants that also form clearing zones in red starch (see comment "Contaminants That Form Clearing Zones in Red Starch" at end of Example 7).
  2. Identify putative hits from the data file produced by the robot computer. The KANAL program produced by Engineering simplifies data analysis. As a rule of thumb, a putative hit is characterized as a well having signal intensity rising at least 1.5 fold over background.
  3. For each putative, remove 2 uL from the well and add to a tube containing 500 uL SM buffer and 50 uL CHCl3. Vortex to mix and store at 4° C. This solution will be referred to hereafter as the 4e-3 stock. The original screening plates should be stored at 4° C., protected from light, at least until breakouts are complete.

This is the recommended method of breaking out putative hits. It is a liquid phase assay that relies on confirmation of activity on BODIPY starch. Alternatively, putative hits can be plated directly onto solid phase plates containing red starch such that 2,000-3,000 pfu per hit are examined for clearing zones. However, inability to observe clearing zones on red starch is not necessarily an indication that a putative hit was a false positive. It would then need to be assayed using the format in which it was originally identified (i.e., liquid phase using BODIPY starch as substrate). In addition, very weak positives are more easily identified using the method detailed below.

Day 1
1. In a sterile 50 mL conical tube, combine 0.5 mL OD5 host cells with 45.5 mL NZY. This will be referred to as the host-medium suspension.
2. For each putative hit to be analyzed, aliquot 1 mL of host-medium suspension into each of 3 three sterile microfuge tubes.
3. Set the 12-channel pipetman in multidispense mode with an aliquot size of 20 uL and an aliquot number of 2×. Mount the pipetman with a clean set of sterile tips.
4. Pour about 1 mL of host-medium suspension into a new sterile solution basin and load the multichannel pipetman.
5. Dispense 20 uL per well into the last row (row P) of a black 384-well plate (12 channels×2=24 wells). This row will be used later for the controls.
6. Expel the remaining liquid in the tips by touching the tips against the surface of the basin and pressing the RESET button on the pipetman. Lay the pipetman down in a way to prevent contamination of the tips. There is no need to change the tips at this point.
7. Pour the remainder of the fluid in the basin into a waste container (like a beaker) taking care to avoid splash-back contamination.
8. For the first putative to be analyzed, take 111 uL of the 4e-3 stock (see Day 2 in *Lambda Microtiter Screening for Amylases*) and add it to the first in a set of three tubes containing 1 mL host-medium suspension (step 2). Vortex to mix. This is Dilution A.
9. Take 111 uL of Dilution A and add to the next tube in the set. Vortex to mix. This is Dilution B.
10. Take 111 uL of Dilution B and add to the last tube in the set. Vortex to mix. This is Dilution C. You should now have three dilutions of phage, where concentrations of each differ by a factor of 10.
11. Pour the contents of Dilution C (the most dilute of the 3 samples) into the solution basin and load the multichannel pipetman.
12. Dispense 20 uL per well into the first row of the 384-well plate (12 channels×2=24 wells).
13. Expel the remaining liquid in the tips by touching the tips against the surface of the basin and pressing the RESET button on the pipetman. Lay the pipetman down in a way to prevent contamination of the tips. There is no need to change the tips at this point.
14. Empty the basin as described above.
15. Pour the contents of Dilution B into the same basin and load the multichannel pipetman.
16. Dispense 20 uL per well into the second row of the 384-well plate.
17. Perform steps 13-16 similarly to dispense Dilution A into the third row of the plate.
18. After all three dilutions have been arrayed into the first 3 rows of the plate, discard all tips and the solution basin into the biohazardous waste container.
19. Mount the pipetman with a clean set of sterile tips and open a new sterile solution basin.
20. Repeat steps 8-19 for each remaining putative hit, using remaining rows on the plate up to row O. Five putative hits can be analyzed on one 384-well plate, with the last row (row P) saved for the controls.
21. Add 0.5 uL of each control to a separate well. Use at least 2-3 separate controls, preferably covering a range of activity.
22. Incubate assay plates at 37° C. overnight in a humidified (≧95%) incubator.

Day 2
1. Pintool all breakout plates onto a host lawn with red starch using the same method described for Day 2 in *Lambda Microtiter Screening for Amylases*, except that a 384 position pintool is used.
2. Prepare the 2× BODIPY starch substrate buffer as follows:
   a) Calculate the total volume of 2× substrate buffer solution needed for all breakout plates at 20 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
3. Dispense 20 uL per well into all breakout plates.
4. Wrap all plates in aluminum foil and incubate at room temperature for 2-6 hours.
5. Read each plate in the Spectrafluor with the following settings:
   a) fluorescence read (excitation filter: 485 nm; emission filter: 535 nm)
   b) plate definition: 384 well black
   c) read from the top
   d) optimal gain
   e) number of flashes: 3
6. On the resulting Excel spreadsheet, chart each putative's 3 rows in a separate graph and check for activity. Ensure that the positives controls produced signals over background.
7. For each putative that appears to have a real signal among the wells, harvest a sample from a positive well as follows:
   a) Select a positive well from a row representing the highest initial dilution.
   b) Transfer 2 uL from that well into a tube containing 500 uL SM and 50 uL $CHCl_3$. This is referred to as the breakout stock.
   c) Store at 4° C.
8. Using methods previously described, plate about 10 uL of each breakout stock onto 150 mm NZY plates using red starch. The objective is to obtain several (at least 20) well-separated plaques from which to core isolates.

Day 3
1. Check pintooled plates for an acceptable incidence of clearings in the bacterial lawn corresponding to wells on the associated assay plate. Also check for clearings in the red starch in the positive controls and in any tested putatives. Be wary of contaminants that also form clearing zones in red starch (see below).
2. From the solid phase plates containing dilutions of breakout stocks, core several isolated plaques, each into 500 uL SM with 50 uL $CHCl_3$. This is referred to as the isolate stock.
3. The isolate stocks can then be individually tested on BODIPY starch using methods described above. This step can be skipped if the plaque that was cored in step 2 produced a clearing zone in the red starch background. The isolate stocks were then be individually tested on BODIPY starch using methods described above. However, this step may be skipped if the plaque that was cored in step 2 produced a clearing zone in the red starch background.

Excisions
Day 1
1. In a Falcon 2059 tube, mix 200 uL OD1 XL1-Blue MRF' host, 100 uL lambda isolate stock and 1 uL ExAssist phage stock.
2. Incubate in 37° C. shaker for 15 minutes.
3. Add 3 mL NZY medium.
4. Incubate in 30° C. shaker overnight.

Day 2
1. Heat to excision tube to 70° C. for 20 minutes.
2. Centrifuge 1000×g for 10 minutes.
3. In a Falcon 2059 tube, combine 50 uL supernatant with 200 uL EXP505 OD1 host.
4. Incubate in 37° C. shaker for 15 minutes.
5. Add 300 uL SOB medium.
6. Incubate in 37 C. shaker for 30-45 minutes.
7. Plate 50 uL on large $LB_{Kan50}$ plate using sterile glass beads. If the plates are "dry", extra SOB medium can be added to help disburse the cells.
8. Incubate plate at 30° C. for at least 24 hours.
9. Culture an isolate for sequencing and/or RFLP.

Growth at 30° C. reduces plasmid copy number and is used to mitigate the apparent toxicity of some amylase clones.

a. Contaminants that Form Clearing Zones in Red Starch

When using red starch on solid medium to assay phage for amylase activity, it is common to see contaminating colony forming units (cfu) that form clearing zones in the red starch. For pintooled plates, it is important to distinguish amylase-positive phage clones from these contaminants whenever they align with a particular well position. The source of the contaminating microbes is presumably the 2% red starch stock solution, which cannot be sterilized by autoclaving or by filtering after preparation. It is thought that they are opportunistic organisms that survive by metabolizing the red starch. In order to reduce these contaminants, use sterile technique when making 2% red starch solutions and store the stocks either at 4° C. or on ice. Replace the stocks every 1-2 weeks or whenever a high incidence of contaminants is observed.

Example 5

Amylase Ligation Reassembly

Nine fragments (each about 150 bp) were amplified from each of the parent clones SEQ ID NO.: 6, SEQ ID NO.: 66, SEQ ID NO.: 67, covering the whole open reading frame. The primers are provided in Table 3.

TABLE 3

| | SEQ ID NO: | |
|---|---|---|
| GAACACTAGTAGGAGGTAACTTATGGCAAAGTATTCCGAGCTCGAAG | 11 | SpeI |
| GAACGGTCTCATTCCGCCAGCCAGCAAGGGGATGAGCGG | 12 | BsaI |
| GAACCGTCTCAAAACACGGCCCATGCCTACGGC | 13 | BsmBI |
| GAACGTCTCACCTCGACTTCCACCCCAACGAGGTCAAG | 14 | BsmAI |
| GAACGTCTCAGGCGCTTTGACTACGTGAAGGGC | 15 | BsmAI |
| GAACGGTCTCAACAAGATGGATGAGGCCTTTG | 16 | BsaI |
| GAACCGTCTCACGATATAATCTGGAACAAGTACCTTGC | 17 | BsmBI |
| GAACCGTCTCAGAAGCACGAGCATAGTTTACTACG | 18 | BsmBI |
| GAACCGTCTCAAAGGTGGGTTTATGTGCCG | 19 | BsmBI |
| GAACGTCTCAGGAATCCAAATGGCGGATATTCCCGC | 20 | BsmAI |
| GAACGGTCTCAGTTTATCATATTGATGAGCTCC | 21 | BsaI |
| GAACCGTCTCAGAGGTAGTTGGCAGTATATTTG | 22 | BsmBI |
| GAACGTCTCACGCCAGGCATCAACGCCGATG | 23 | BsmAI |
| GAACGTCTCATTGTAGTAGAGCGGGAAGTC | 24 | BsmAI |
| GAACGGTCTCAATCGGTGTCGTGGTTTGCTAC | 25 | BsaI |
| GAACCGTCTCACTTCCACCTGCGAGGTGGTC | 26 | BsmBI |
| GAACCGTCTCACCTTCCAACCTTGCTCGAGC | 27 | BsmBI |
| TCGAGACTGACTCTCACCCAACACCGCAATAGC | 28 | |
| GAACACTAGTAGGAGGTAACTTATGGCCAAGTACCTGGAGCTCGAAGAGG | 29 | SpeI |
| GAACGGTCTCATTCCCCGGCGAGCAAGGGC | 30 | BsaI |
| GAACCGTCTCAAAACACCGCCCACGCCTACGG | 31 | BsmBI |
| GAACGTCTCACCTCGACTTCCACCCCAAC | 32 | BsmAI |
| GAACGTCTCAGGCGCTTCGACTACGTCAAGG | 33 | BsmAI |
| GAACGGTCTCAACAAGATGGACGCGGCCTTTGAC | 34 | BsaI |
| GAACCGTCTCACGATATAATTTGGAACAAGTACCC | 35 | BsmBI |
| GAACCGTCTCAGAAGCACCGACATAGTCTAC | 36 | BsmBI |
| GAACCGTCTCAAAGGTGGGTCTACGTTCCG | 37 | BsmBI |
| GAACGTCTCAGGAATCCATATTGCGGAGATTCCGGC | 38 | BsmAI |
| GAACGGTCTCAGTTTATCATGTTCACGAGCTC | 39 | BsaI |
| GAACCGTCTCAGAGGTAGTTGGCCGTGTACTTG | 40 | BsmBI |
| GAACGTCTCAGCCATGCGTCAACGCCGATG | 41 | BsmAI |
| GAACGTCTCATTGTAGTAGAGCGGGAAGTCG | 42 | BsmAI |
| GAACGGTCTCAATCGGTGTCGTGGTTTGCAACG | 43 | BsaI |
| GAACCGTCTCACTTCCACCGGCGAGGTGGTCGTG | 44 | BsmBI |
| GAACCGTCTCACCTTCCGGCCTTGCTCGAGCC | 45 | BsmBI |
| TCGAGACTGACTCTCAGCCCACCCCGCAGTAGCTC | 46 | |
| GAACACTAGTAGGAGGTAACTTATGGCCAAGTACTCCGAGCTGGAAGAGG | 47 | SpeI |
| GAACGGTCTCATTCCTCCCGCGAGCAAGGG | 48 | BsaI |
| GAACCGTCTCAAAACACCGCCCACGCCTATG | 49 | BsmBI |
| GAACGTCTCACCTCGACTTCCACCCGAACGAGC | 50 | BsmAI |
| GAACGTCTCAGGCGCTTCGACTACGTCAAGG | 51 | BsmAI |
| GAACGGTCTCAACAAGATGGACGAGGCCTTCG | 52 | BsaI |
| GAACCGTCTCACGATATAATCTGGAACAAG | 53 | BsmBI |
| GAACCGTCTCAGAAGCACTGACATCGTTTACTACG | 54 | BsmBI |
| GAACCGTCTCAAAGGTGGGTTTACGTTCCG | 55 | BsmBI |
| GAACGTCTCAGGAATCCATATCGCCGAAAT | 56 | BsmAI |
| GAACGGTCTCAGTTTATCATGTTTATGAGC | 57 | BsaI |
| GAACCGTCTCAGAGGTAGTTGGCCGTGTATTTAC | 58 | BsmBI |
| GAACGTCTCACGCCAGGCATCGATGCCGAT | 59 | BsmAI |
| GAACGTCTCATTGTAGTAGAGGGCGAAGTCAAAG | 60 | BsmAI |
| GAACGGTCTCAATCGGTATCGTGGTTGGCTACAAAC | 61 | BsaI |
| GAACCGTCTCACTTCCTCCGGCGAGGTTGTCATG | 62 | BsmBI |
| GAACCGTCTCACCTTCCGGCTTTGCTTGAGGC | 63 | BsmBI |
| TCGAGACTGACTCTCACCCAACACCGCAGTAGCTCC | 64 | |
| CACACAGCAGCAACCAACCTCGAGACTGACTCTCASCC | 65 | BbvI |

Conditions used for PCR were as follows: 3 min 94° C., (30 sec 94° C.; 30 sec 55° C., 30 sec 68° C.)×30 cycles, followed by 10 min 68° C. PCR products corresponding to homologous regions from the three parents were pooled (1:1:1), cut with the appropriate restriction enzyme (see Table 3), and gel-purified. Equal amounts of fragment pools were combined and ligated (16° C.; over night). The resulting 450 bp ligation products were gel purified and ligated to yield full length amylase genes. The resulting full length products were gel-purified and PCR amplified using a mixture of F1 primers SEQ ID NO.: 6, SEQ ID NO.: 66, SEQ ID NO.: 67 and primer SEQ ID NO:65. Conditions used for PCR were as follows: 3 min 94° C., (30 sec 94° C.; 30 sec 50° C., 60 sec 68° C.)×30 cycles, followed by 10 min 68° C.

The resulting PCR products (~1.4 kbp) were purified, cut with SpeI and BbvI, gel-purified, ligated into pMYC (vector from Mycogen, cut with SpeI/XhoI), and transformed into E. coli Top 10. Plasmid DNA from a pool of ~21000 colonies was isolated and transformed into Pseudomonas.

Screening of Reassembled α-Amylase

The transformed Pseudomonas fluorescens (MB214) containing pMYC derived from the parent clones SEQ ID NO:6, SEQ ID NO:66, SEQ ID NO:68 were sorted to 96- or 384-well plates by FACS and treated with 6M urea. Primary screening using RBB-starch and/or FITC-starch as substrates was carried out as described more fully below. Elevated active clones were screened using RBB-starch as substrate using induced cultures and by liquefaction assay.

Stock and sequencing new elevated active clones based on liquefaction data was performed.

The transformed reassembled amylase library (MB214 (Pf)), were collected and sorted into 96-well plates (or 384-well plates) at 1 cell/well in 50 μl of LB+Tet. The plates were incubated for 24 hours at 30° C. Replicate plates were made corresponding to each well for storage. Forty-five (45) μl of 12M urea was added to each well and the plates were shaken for 10 minutes. Plates were kept at room temp for at least 1 hour and the lysate stored at 4° C.

Assay Using RBB-Starch

75 μl of RBB-starch substrate (1% RBB-insoluble corn starch in 50 mM NaAc buffer, pH=4.5) was added into each well of a new 96-well plate (V-bottom). Five micro-liters of enzyme lysate was transfered into each well with substrate using Biomek or Zymark. The plates were sealed with aluminum sealing tape and shaken briefly on the shaker. The plates were incubated at 90° C. for 30 minutes, followed by cooling at room temperature for about 5 to 10 minutes. One hundred micro-liters of 100% ethanol was added to each well, the plates sealed and shaken briefly on the shaker. The plates were then centrifuged 400 rpm for 20 minutes using bench-top centrifuge. 100 μl of the supernatant was transferred into a new 96-well plate (flat bottom) by Biomek and read $OD_{595}$. Controls: SEQ ID NO:6, SEQ ID NO:66, SEQ ID NO:68.

Assay Using FITC-Starch

Added 50 μl of substrate (0.01% FITC-starch in 100 mM NaAc buffer, pH=4.5) into each well of a new 384-well plate. Transfered 5 μl of enzyme lysate into each well with substrate and incubated the plate at room temperature overnight. The polarization change of the substrate, excitation 485 nm, emission 535 nm, was read for each well. Controls: SEQ ID NO:6, SEQ ID NO:66, SEQ ID NO:68. Preferably 96 well plates are used for all assays.

Confirmation of New Active Clones

Each positive clone from screening was grown and induced using a standard protocol. Each clone was examined for growth (i.e., cell density over time), activity at per cell level (RBB-starch assay and liquefaction assay), expression (protein gel) and solubility of protein (by microscope analysis). The confirmed new elevated clones were transferred for fermentation. One of the clones have amylase activity greater than that of the parent includes the enzyme set forth in SEQ ID NO:2 (encoded by SEQ ID NO:1).

Example 6

Amylase Liquefaction

This example characterizes the liquefaction oligosaccharide patterns resulting from the invention enzymes, SEQ ID NO:6 and SEQ ID NO:2 vs commercial *Bacillus licheniformis* and *Bacillus stearothermophilus* amylases. These results looked at the saccharification progress and final dextrose levels from syrups generated by invention and commercial amylases.

Three commercial enzymes, Genencor Spezyme AA, and two others all required more than double the recommended dosage to achieve the target Dextrose equivalent (DE). Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

This confirms the "double dosage" effect for all Bacillus amylases and gives more credence to the proposal that the observed dosage for SEQ ID NO:2 in the trials is also twice the value which would be required under more normal conditions. The projected "normal" dosage, 60-70 Units/kilo starch at pH 4.5 to reach a 19 DE, is consistent with the laboratory liquefaction data.

The oligosaccharide pattern generated by invention amylases is different from the Bacillus profiles. The molecular weight distribution for the Bacillus amylases (gel permeation chromatography with detection by light scattering and viscosity) is bimodal with a substantial fraction at the very high molecular weight range (>300,000) even at an 18 DE. The SEQ ID NO:2 at 18 DE exhibits a uniform distribution with nothing greater than 20,000. This is consistent with the lower viscosity for Invention syrups. The DP (degrees of polymerization) profiles as measured by HPLC also reflects this difference in action pattern.

In this study, as well as in the previous studies, the final glucose level after saccharification of Invention amylase liquefied syrups vs the Bacillus syrups is the same for both cases. However, we have now acquired sufficient saccharification data from internal as well as from the GPC studies to confirm that the non-dextrose residuals for the invention amylases are different from the Bacillus amylase syrups. Although the dextrose and maltose levels are essentially the same for both, the Invention amylases have a higher DP3 fraction but lower amount of the "highers" vs. the Bacillus enzyme. Consistent with the absence of high molecular weight fragments after liquefaction, the post saccharification Invention syrups have a lower content of the >DP7 fraction.

|  | Glucose | DP2 | DP3 | >DP7 |
|---|---|---|---|---|
| SEQ ID NO: 2 | 95.25 | 2.39 | 1.13 | 0.91 |
| Commercial | 94.16 | 2.10 | 0.39 | 2.91 |
| SEQ ID NO: 6 | 94.77 | 2.27 | 1.48 | 0.82 |

SEQ ID NO:2 amylase concentrate was prepared from fermentation broths by heat treatment, cell washing, alkaline extraction using microfiltration and ultraflitration (48% overall yield). The UF concentrate was neutralized with acetic acid and formulated with 30% glycerol at pH 4.5. The activity level of the slurry formulation was representative of a commercial product (120 $U^1$/g–0.5 kg/ton starch).

Standard Amylase Activity Assay

A 1 mL cuvette containing 950 μL of 50 mM MOPS pH 7.0 containing 5 mM PNP-α-D-hexa-(1→4)-glucopyranoside was placed in the Peltier temperature controller of the Beckman DU-7400 spectrophotometer preheated to 80° C. The spectrophotometer was blanked at 405 nm and 50 μL of the enzyme solution was added to the cuvette, mixed well and the increase in the OD405 nm was monitored over a one-minute interval. The $\Delta OD_{405\ nm/min}$ rate is converted to a standard unit of μmole/minute from the $OD_{405\ nm}$ response of 50 μL of 1 μmole/mL PNP in 950 mL 50 mM MOPS at pH 7.0-80° C. One standard Diversa unit of thermostable alpha amylase (DTAA) is equal to the amount of enzyme that will catalyze the release of 1 μmole/mL/minute of pNP under the defined conditions of the assay.

Standard Glucoamylase Activity Assay

A 1 mL cuvette containing 950 μL of 50 mM MOPS pH 7.0 containing 5 mM pNP-α-D-glucopyranoside was placed in the Peltier temperature controller of the Beckman DU-7400 spectrophotometer preheated to 60° C. The spectrophotometer was blanked at 405 nm and 50 µL of the enzyme solution was added to the cuvette, mixed well and the increase in the $OD_{405\ nm}$ was monitored over a one-minute interval. The $\Delta OD_{405\ nm}$/min rate is converted to a standard unit of pmole/minute from the $OD_{405\ nm}$ response of 50 µL of 1 µmole/mL pNP in 950 mL 50 mM MOPS at pH 7.0-60° C. One standard Diversa unit of glucoamylase (DGA) is equal to the amount of enzyme that will catalyze the release of 1 µmole/mL/minute of pNP under the defined conditions of the assay.

Dextrose Equivalent Determination

The neocuproine method was used to measure the DE. Selected samples were measured by both the Invention procedure and by a GPC analyst using the GPC Fehlings procedure.

Neocuproine Assay

A 100 µl sample was added to 2.0 ml of neocuproine solution A (40 g/L sodium carbonate, 16 g/L glycine, 0.45 g/L copper sulfate). To this was added 2.0 ml of neocuproine solution B (1.2 g/L neocuproine hydrochloride-Sigma N-1626). The tubes were mixed and heated in a boiling water bath for 12 minutes; cooled, diluted to 10 ml volume with DI water and the OD read at 450 nm on the spectrophotometer. The glucose equivalent in the sample was extrapolated from the response of a 0.2 mg/ml glucose standard run simultaneously.

The starch sample is diluted ~1 to 16 with DI water with the exact dilution recorded. Ten milliliters of the diluted sample was added to 20 mls of DI water. Ten milliliters of Fehlings solution A and B were added to the diluted starch. The sample was boiled for 3 minutes and cooled on ice. Ten milliliters of 30% KI and 10 ml of 6N $H_2SO_4$ was added. The solution was titrated against 0.1N sodium thiosulfate. The titrant volume is recorded and used to calculate the DE.

Residual Starch Determination

Post-saccharification samples were checked for residual starch using the Staley iodine procedure Twenty grams of sample was weighed into a large weigh dish. 45 µL of Iodine solution is added to the weigh dish and the starch solution is mixed well. Dark blue indicates the presence of starch, a light blue-green indicates slight starch, light green indicates a trace of starch and yellow-red, absence of starch. Iodine solution is prepared by dissolving 21.25 grams of iodine and 40.0 grams of potassium iodide in one liter of water.

Oligosaccharide Profile

Liquefaction and saccharification carbohydrate profiles were measured by HPLC (Bio-Rad Aminex HPX-87C column in calcium form –80 C.) using refractive index detection.

Gel Permeation Chromatography

The molecular weight distribution was determined by chromatography on a PL Aquagel-OH column with mass detection by refractive index (Waters Model 2410). A Viscotek Model T60 detector was used for continuous viscosity and light scattering measurements.

Capillary Electrophoresis

Beckman Coulter P/ACE MDQ Glycoprotein System—separation of APTS derivatized oligosaccharides on a fused silica capillary—detection by laser-induced fluorescence.

Primary Liquefaction

Line starch directly from the GPC process is pumped into a 60 liter feed tank where pH, DS (dry solids) and calcium level can be adjusted before liquefaction. The amylase is added to the slurry. The 32% DS slurry is pumped at 0.7 liter/minute by a positive displacement pump to the jet—a pressurized mixing chamber where the starch slurry is instantaneously heated to greater than 100 C. by steam injection. The gelatinized partially liquefied starch is pumped through a network of piping (still under pressure) to give the desired dwell time (5 minutes) at temperature. The pressure is released into a flash tank and samples can be taken. Samples were taken in duplicate.

Secondary Liquefaction

The liquefied starch was collected in one liter glass bottles and held in a water bath at 95 C. for 90 minutes.

Saccharification

Liquefied starch was cooled to 60 C., the pH adjusted to 4.5 and the samples treated with glucoamylase. Saccharification progress was monitored over time by HPLC.

Preparation of Liquefied Syrups for Analysis

These trials were run to obtain liquefied syrups at DE's of 12 and 18 for three amylases; SEQ ID NO:6, SEQ ID NO:2, commercial *B. licheniformis* amylase. The syrups were saccharified with three levels of glucoamylase. The liquefied syrups were also analyzed by HPLC and gel permeation chromatography.

Saccharification

The liquefied syrups produced with each amylase were adjusted to approximately pH 2.5 with 6N HCl immediately after the 90 minute secondary liquefaction to inactivate any residual amylase. The syrups were then adjusted to pH 4.5, placed in a 60 C. water bath and saccharified with three levels of glucoamylase. The extent of saccharification was monitored by HPLC at 18-88 hour time points.

The liquefied syrups were saccharified with the standard dosage—0.04% of a double-strength glucoamylase—and two lower dosages (50% and 25%) to monitor any differences in the saccharification progress. As the previous plots and the tables below indicate, the glucose levels are higher at earlier time points with the SEQ ID NO:2 syrups. Some of the difference is due to a higher starting point but the molecular weight profile difference is also a contributing factor (the oligosaccharides in the SEQ ID NO:2 liquefied syrups—being smaller and more uniform—should be, and apparently are, better substrates for glucoamylase).

| Saccharification Progress-% dextrose development vs time-0.04% glucoamylase | | | | | |
|---|---|---|---|---|---|
| Amylase | 18 hr | 24 hr | 40 hr | 44 hr | 88 hr |
| Commercial | 70.2 | 78.4 | 86.1 | 86.7 | 94.2 |
| SEQ ID NO: 2 | 79 | 88.6 | 92.5 | 92.8 | 95.3 |
| SEQ ID NO: 6 | 74.1 | 85.9 | 91.9 | 91.6 | 94.8 |

| Saccharification Progress-% dextrose development vs time-0.02% glucoamylase | | | | | |
|---|---|---|---|---|---|
| Amylase | 18 hr | 24 hr | 40 hr | 44 hr | 88 hr |
| B. licheniformis Amylase | 54.5 | 66.7 | 76.1 | 77.2 | 90.9 |
| SEQ ID NO: 2 | 60.1 | 72 | 84.8 | 85.3 | 93.6 |
| SEQ ID NO: 6 | 57.1 | 70 | 84 | 86.5 | 92.5 |

Post-Saccharification Sugar Profile

In these studies and all previous saccharification studies, the final glucose level achieved after saccharification of Invention amylase and *B. licheniformis* liquefied syrups is essentially identical. The DP2 (maltose) level is also similar. These large fragments are poor substrates for glucoamylase and tend to be converted slowly, if at all, into smaller fragments and ultimately, glucose).

|            | Glucose | 'DP 2 | DP3  | >DP7 |
|------------|---------|-------|------|------|
| SEQ ID NO: 2 | 95.25   | 2.39  | 1.13 | 0.91 |
| Commercial | 94.16   | 2.10  | 0.39 | 2.91 |
| SEQ ID NO: 6 | 94.77   | 2.27  | 1.48 | 0.82 |

Molecular Weight Distribution

The molecular weight distribution of syrups liquefied to DE's of 12 and 18 by Invention amylases (SEQ ID NO:6 and SEQ ID NO:2) and commercial *Bacillus licheniformis* and commercial *Bacillus stearothermophilus* were measured by gel permeation chromatography using detection by refractive index, light scattering and viscosity. Both the *licheniformis* and *stearothermophilus* amylases generate a bimodal distribution—the primary peak centered at 2000, a secondary peak at 32,000 with a shoulder extending past the 160,000 range. The lower molecular weight peak represents approximately 60% of the total mass of the sample. The Invention amylases exhibit a single peak at 2000 with very little above 30,000.

HPLC

The DE 12 and 18 syrups produced by the Invention and commercial amylases were analyzed by HPLC. Both techniques (chromatograms/electropherograms shown in Appendices) produce fingerprints characteristic of each class of amylase; the oligosaccharide patterns are different for *licheniformis* vs *stearothermophilus* vs the Invention amylases. The Invention liquefied syrups exhibit evidence of greater branching in the oligosaccharides. HPLC only resolve the oligosaccharides in the <DP15 range—larger fragments are not visible in these techniques. Bacillus amylases are known to liquefy starch in a manner such that the amylopectin fraction is hydrolyzed less extensively than the amylose fraction. These >DP30 amylopectin fragments are contained in the high molecular weight fraction centered at 32,000 and consequently, little evidence of branching is seen in the HPLC analyses of the Bacillus liquefied syrups. The <DP15 oligosaccharides from Invention amylases contain fragments from both amylose and amylopectin.

Although the invention has been described with reference to the presently preferred embodiment, it should be understood that various modifications can be made without departing from the spirit of the invention. Accordingly, the invention is limited only by the following claims.

What is claimed is:

1. An isolated, synthetic or recombinant nucleic acid comprising (a) a sequence having at least or about 95% sequence identity to SEQ ID NO:1, wherein the nucleic acid encodes a polypeptide having alpha amylase activity; and (b) sequences fully complementary to (a).

2. An isolated, synthetic or recombinant nucleic acid comprising (a) a sequence encoding a polypeptide having alpha amylase activity, wherein the complement of said sequence hybridizes under highly stringent conditions to SEQ ID NO:1, and (b) sequences fully complementary to (a), wherein the highly stringent conditions comprise a hybridization under conditions comprising a buffer comprising 50% formamide at about 37° C. to 42° C.; or, 42° C. in 50% formamide, 5× SSPE, 0.3% SDS, and a wash step comprising use of a buffer comprising 0.15 NaCl for 15 min at 72° C.

3. The isolated, synthetic or recombinant nucleic acid of claim 1, wherein said sequence has at least about 97% sequence identity to SEQ ID NO:1.

4. The isolated, synthetic or recombinant nucleic acid of claim 3, wherein said sequence has at least about 98% sequence identity to SEQ ID NO:1.

5. The isolated, synthetic or recombinant nucleic acid of claim 1, wherein the sequence identity is determined using a sequence comparison algorithm comprising FASTA version 3.0t78 with the default parameters.

6. An isolated, synthetic or recombinant nucleic acid encoding a polypeptide having an amino acid sequence having at least about 95% sequence identity to SEQ ID NO:2, wherein the polypeptide is capable of hydrolyzing a starch to a sugar.

7. A method of producing a recombinant polypeptide comprising the steps of introducing a nucleic acid encoding the polypeptide into an isolated host cell under conditions that allow expression of the polypeptide, wherein the nucleic acid comprises the sequence of claim 1.

8. A method of producing and recovering a recombinant polypeptide comprising the steps of: introducing the nucleic acid of claim 1 operably linked to a promoter, into an isolated host cell under conditions that allow expression of the polypeptide, and recovering the recombinant polypeptide.

9. A method of generating an amylase-encoding polynucleotide comprising: obtaining the amylase-encoding nucleic acid of claim 1 or claim 2 and modifying one or more nucleotides in said polynucleotide to another nucleotide, deleting one or more nucleotides in said polynucleotide, or adding one or more nucleotides to said polynucleotide to obtain a modified nucleic acid sequence, wherein the modified nucleic acid sequence encodes an polypeptide having an amylase activity.

10. The method of claim 9, wherein the modifications are introduced by a method selected from the group consisting of: effor-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM) and any combination of these methods.

11. The method of claim 10, wherein the modifications are introduced by effor-prone PCR.

12. The method of claim 10, wherein the modifications are introduced by shuffling.

13. The method of claim 10, wherein the modifications are introduced by oligonucleotide-directed mutagenesis.

14. The method of claim 10, wherein the modifications are introduced by assembly PCR.

15. The method of claim 10, wherein the modifications are introduced by sexual PCR mutagenesis.

16. The method of claim 10, wherein the modifications are introduced by in vivo mutagenesis.

17. The method of claim 10, wherein the modifications are introduced by cassette mutagenesis.

18. The method of claim 10, wherein the modifications are introduced by recursive ensemble mutagenesis.

19. The method of claim 10, wherein the modifications are introduced by exponential ensemble mutagenesis.

20. The method of claim 10, wherein the modifications are introduced by site-specific mutagenesis.

21. The method of claim 10, wherein the modifications are introduced by gene reassembly.

22. The method of claim 10, wherein the modifications are introduced by Gene Site Saturation Mutagenesis (GSSM).

23. A method for comparing a first sequence to a second sequence comprising the steps of: reading the first sequence and the second sequence through use of a computer program which compares sequences; and determining differences between the first sequence and the second sequence with the computer program, wherein said first sequence comprises the nucleic acid sequence of claim 1 or claim 2.

24. The method of claim 23, wherein the step of determining differences between the first sequence and the second sequence further comprises the step of identifying polymorphisms.

25. A method for identifying a feature in a sequence comprising the steps of: reading the sequence using a computer program which identifies one or more features in a sequence; and identifying one or more features in the sequence with the computer program, wherein the sequence comprises the nucleic acid sequence of claim 1 or claim 2.

26. A nucleic acid probe for identifying or isolating an amylase-encoding nucleic acid, comprising a nucleic acid that specifically hybridizes under highly stringent hybridization conditions to the amylase-encoding nucleic acid of claim 1 or claim 2, or its fully complementary sequence, wherein the highly stringent hybridization conditions comprise a hybridization under conditions comprising 50% formamide at about 37° C. to 42° C.; or, 42° C. in 50% formamide, 5× SSPE, 0.3% SDS, and a wash step comprising use of a buffer comprising 0.15 NaCl for 15 min at 72° C.

27. The probe of claim 26, wherein the nucleic acid comprises DNA or RNA.

28. The probe of claim 26, wherein the probe further comprises a detectable isotopic label or a detectable non-isotopic label.

29. The probe of claim 28, wherein the probe further comprises a detectable non-isotopic label selected from the group consisting of a fluorescent molecule, a chemiluminescent molecule, an enzyme, a cofactor, an enzyme substrate, and a hapten.

30. A cloning vector comprising the nucleic acid of claim 1 or claim 2.

31. An isolated host cell transformed or transfected with the nucleic acid of claim 1 or claim 2.

32. An expression vector capable of replicating in a host cell comprising the nucleic acid of claim 1 or claim 2.

33. A cloning vector as claimed in claim 30, wherein the cloning vector comprises a viral vector, a plasmid, a phage, a phagemid, a cosmids, a fosmid, a bacteriophage, an artificial chromosome, an adenovirus vector, a retroviral vector, or an adeno-associated viral vector.

34. An isolated host cell transformed or transfected with the expression vector of claim 32.

35. An isolated host cell as claimed in claim 31, wherein the host is selected from the group consisting of prokaryotes, eukaryotes, funguses, yeasts, plants and non-human metabolically rich hosts.

36. A method of producing a recombinant polypeptide comprising the steps of
(a) introducing a nucleic acid encoding the polypeptide into an isolated host cell under conditions that allow expression of the polypeptide, wherein the nucleic acid comprises the sequence of claim 2, or,
(b) introducing the nucleic acid of claim 2 into an isolated host cell under conditions that allow expression of the polypeptide, thereby producing a recombinant polypeptide.

37. An expression vector comprising the nucleic acid of claim 1 or claim 2, wherein the expression vector comprises a viral vector, a plasmid, a phage, a phagemid, a cosmids, a fosmid, a bacteriophage, an artificial chromosome, an adenovirus vector, a retroviral vector, or an adeno-associated viral vector.

38. An isolated host cell transformed the nucleic acid of claim 1 or claim 2, wherein the cell is a prokaryote cell, a eukaryote cell, a fungus cell, a yeast cell, a plant cell or a non-human metabolically rich host cell.

* * * * *

SEQUENCE LISTING

```
<160> NUMBER OF SEQ ID NOS: 69

<210> SEQ ID NO 1
<211> LENGTH: 1311
<212> TYPE: DNA
<213> ORGANISM: Artificial Sequence
<220> FEATURE:
<223> OTHER INFORMATION: Synthetically generated

<400> SEQUENCE: 1
atggccaagt actccgagct ggaaaagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360 aacccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600 gtcaaggct atgctccctg ggtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg cgacccgttc     840
```

```
aaggccgtaa cctttgtagc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgagaacct cgccggagga   1020
agcaccgaca tagtctacta cgataacgat gaactcatct tcgtcaggaa cggctacggg   1080
gacaagccgg ggcttataac ctacatcaac ctaggctcga gcaaggccgg aaggtgggtt   1140
tatgtgccga agttcgcggg cgcgtgcatc acgagtata ctggtaacct cggaggctgg    1200
gtagacaagt acgtctactc aagcggctgg gtctatctcg aagctccagc ttacgaccct   1260
gccaacgggc agtatggcta ctccgtgtgg agctactgcg gggtgggctg a            1311
```

<210> SEQ ID NO 2
<211> LENGTH: 436
<212> TYPE: PRT
<213> ORGANISM: Artificial Sequence
<220> FEATURE:
<223> OTHER INFORMATION: Synthetically engineered

<400> SEQUENCE: 2

```
Met Ala Lys Tyr Ser Glu Leu Glu Lys Gly Gly Val Ile Met Gln Ala
 1               5                  10                  15

Phe Tyr Trp Asp Val Pro Ser Gly Ile Trp Trp Asp Thr Ile Arg
                20                  25                  30

Gln Lys Ile Pro Glu Trp Tyr Asp Ala Gly Ile Ser Ala Ile Trp Ile
             35                  40                  45

Pro Pro Ala Ser Lys Gly Met Gly Gly Ala Tyr Ser Met Gly Tyr Asp
 50                  55                  60

Pro Tyr Asp Phe Phe Asp Leu Gly Glu Tyr Asp Gln Lys Gly Thr Val
 65                  70                  75                  80

Glu Thr Arg Phe Gly Ser Lys Gln Glu Leu Val Asn Met Ile Asn Thr
                 85                  90                  95

Ala His Ala Tyr Gly Met Lys Val Ile Ala Asp Ile Val Ile Asn His
                100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285
```

```
His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 3
<211> LENGTH: 1419
<212> TYPE: DNA
<213> ORGANISM: Unknown
<220> FEATURE:
<223> OTHER INFORMATION: Obtained from an environmental sample

<400> SEQUENCE: 3
atgttcctgc tcgcgttttt gctcactgcc tcgctgttct gcccaacagg acagcccgcc     60
aaggctgccg caccgtttaa cggcaccatg atgcagtatt ttgaatggta cttgccggat    120
gatggcacgt tatggaccaa agtggccaat gaagccaaca acttatccag ccttggcatc    180
accgctcttt ggctgccgcc cgcttacaaa ggaacaagcc gcagcgacgt agggtacgga    240
gtatacgact tgtatgacct cggcgaattc aatcaaaaag ggaccgtccg cacaaaatac    300
ggaacaaaag ctcaatatct tcaagccatt caagccgccc acgccgctgg aatgcaagtg    360
tacgccgatg tcgtgttcga ccataaaggc ggcgctgacg cacggaatgg gtggacgcc    420
gtcgaagtca atccgtccga ccgcaaccaa gaaatctcgg gcacctatca atccaagca    480
tggacgaaat ttgattttcc cgggcgggc aacacctact ccagctttaa gtggcgctgg    540
taccattttg acggcgttga ttgggacgaa agccgaaaat tgagccgcat ttacaaattc    600
cgcggcatcg gcaaagcgtg ggattgggaa gtagacacgg aaaacggaaa ctatgactac    660
ttaatgtatg ccgaccttga tatggatcat cccgaagtcg tgaccgagct gaaaaactgg    720
gggaaatggt atgtcaacac aacgaacatt gatgggttcc ggcttgatgc cgtcaagcat    780
attaagttca gtttttttcc tgattggttg tcgtatgtgc gttctcagac tggcaagccg    840
ctatttaccg tcggggaata ttggagctat gacatcaaca agttgcacaa ttacattacg    900
aaaacagacg gaacgatgtc tttgtttgat gccccgttac acaacaaatt ttataccgct    960
tccaaatcag ggggcgcatt tgatatgcgc acgttaatga ccaatactct catgaaagat   1020
caaccgacat tggccgtcac cttcgttgat aatcatgaca ccgaacccgg ccaagcgctg   1080
cagtcatggg tcgacccatg gttcaaaccg ttggcttacg cctttattct aactcggcag   1140
```

```
gaaggatacc cgtgcgtctt ttatggtgac tattatggca ttccacaata taacattcct    1200
tcgctgaaaa gcaaaatcga tccgctcctc atcgcgcggg ggattatgc ttacggaacg    1260 caacatgatt atcttgatca ctccgacatc atcggtgga caagggaagg ggtcactgaa    1320
aaaccaggat ccgggctggc cgcactgatc accgatgggc cggaggaag caaatggatg    1380 tactgttggc aaacaacacg ctggaaaagt gttctatga                          1419

<210> SEQ ID NO 4
<211> LENGTH: 1539
<212> TYPE: DNA
<213> ORGANISM: Unknown
<220> FEATURE:
<223> OTHER INFORMATION: Obtained from an environmental sample

<400> SEQUENCE: 4
atgaaacaac aaaaacggct ttacgcccga ttgctgacgc tgttatttgc gctcatcttc      60
ttgctgcctc attctgcagc agcggcggca aatcttaatg ggacgctgat gcagtatttt    120
gaatggtaca tgcccaatga cggccaacat tggaagcgct tgcaaaacga ctcggcatat    180
ttggctgaac acgtattac tgccgtctgg attcccccgg catataaggg aacgagccaa     240
gcggatgtgg gctacggtgc ttacgacctt tatgatttag gggagtttca tcaaaaaggg    300
acggttcgga caaagtacgg cacaaaagga gagctgcaat ctgcgatcaa agtcttcat     360 tcccgcgaca ttaacgttta cggggatgtg gtcatcaacc acaaaggcgg cgctgatgcg    420
accgaagatg taaccgcggt tgaagtcgat cccgctgacc gcaaccgcgt aatttcagga    480
gaacaccgaa ttaaagcctg gacacatttt catttccgg ggcgcggcag cacatacagc    540
gattttaaat ggcattggta ccatttgac ggaaccgatt gggacgagtc ccgaaagctg    600
aaccgcatct ataagtttca aggaaaggct tgggattggg aagtttccaa tgaaaacggc    660
aactatgatt atttgatgta tgccgacatc gattatgacc atcctgatgt cgcagcagaa    720
attaagagat ggggcacttg gtatgccaat gaactgcaat tggacggttt ccgtcttgat    780
gctgtcaaac acattaaatt ttctttttg cgggattggg ttaatcatgt cagggaaaaa    840
acggggaagg aaatgtttac ggtagctgaa tattggcaga atgacttggg cgcgctggaa    900
aactatttga caaaacaaa tttttaatcat tcagtgtttg acgtgccgct tcattatcag    960
ttccatgctg catcgacaca gggaggcggc tatgatatga ggaaattgct gaacggtacg   1020
gtcgtttcca agcatccgtt gaaagcggtt acatttgtcg ataaccatga tacacagccg   1080
gggcaatcgc ttgagtcgac tgtccaaaca tggtttaagc cgcttgctta cgctttcatt   1140
ctcacaaggg aatctggata ccctcaggtt ttctacgggg atatgtacgg gacgaaagga   1200
gactcccagc gcgaaattcc tgccttgaaa cacaaaattg aaccgatctt aaaagcgaga   1260
aaacagtatg cgtacggagc acagcatgat tatttcgacc accatgacat tgtcggctgg   1320
acaagggaag cgacagctc ggttgcaaat tcaggtttgg cggcattaat aacagacgga   1380
cccggtgggg caaagcgaat gtatgtcggc cggcaaaacg ccggtgagac atggcatgac   1440
attaccggaa accgttcgga gccggttgtc atcaattcgg aaggctgggg agagtttcac   1500
gtaaacggcg ggtcggtttc aatttatgtt caaagatag                          1539

<210> SEQ ID NO 5
<211> LENGTH: 1395
<212> TYPE: DNA
<213> ORGANISM: Unknown
<220> FEATURE:
<223> OTHER INFORMATION: Obtained from an environmental sample
```

<400> SEQUENCE: 5

```
gtggtgcaca tgaagttgaa gtaccttgcc ttagttttgt tggctgtggc ttcgataggc    60
ctactctcga ctccagtggg tgctgccaag tactccgaac tcgaagaggg cggtgttata   120
atgcaggcct tctactggga tgttcccgga gggggaatct ggtgggacac cataagacag   180
aaaatcccgg agtggtacga cgctggaatc tcggcgatat ggattcctcc agctagcaaa   240
gggatgggcg gtggttattc catgggctac gatccctacg atttctttga cctcggcgag   300
tactatcaga agggaacagt tgagacgcgc ttcggctcaa aggaggaact ggtgaacatg   360
ataaacaccg cacactccta tggcataaag gtgatagcgg acatagtcat aaaccaccgc   420
gccggtggag accttgagtg gaacccctt gtaaacaact atacttggac agacttctcc   480
aaggtcgcct ccggtaaata cacggccaac taccttgact tccacccaaa cgaggtcaag   540
tgctgcgatg agggtacatt tggtgacttt ccggacatcg cccacgagaa gagctgggat   600
cagtactggc tctgggcaag caatgagagc tacgccgcat atctccggag catagggatc   660
gatgcatggc gtttcgacta cgtcaaaggt tacgagcgt gggttgttaa tgactggctc   720
agctggtggg gaggctgggc cgttggagag tactgggaca cgaacgttga tgcactcctt   780
aactgggcat acgacagcgg tgccaaggtc tttgacttcc cgctctacta caagatggac   840
gaagcctttg caacaccaa catccccgct ttggtttacg ccctccagaa cggaggaaca   900
gtcgtttccc gcgatccctt caaggcagta actttcgttg ccaaccacga tacagatata   960
atctggaaca agtatccggc ttatgcgttc atccttacct atgagggaca gcctgttata  1020
ttttaccgcg actacgagga gtggctcaac aaggataagc ttaacaacct tatctggata  1080
cacgagcacc ttgccggagg aagtaccaag atcctctact acgataacga tgagctaata  1140
ttcatgaggg agggctacgg gagcaagccg ggcctcataa cctacataaa cctcggaaac  1200
gactgggcca gcgctgggt gaacgtcggc tcaaagtttg ccggctacac aatccatgaa  1260
tacacaggca atctcggtgg ctgggttgac aggtgggttc agtacgatgg atgggttaaa  1320
ctgacggcac ctcctcatga tccagccaac ggatattacg gctactcagt ctggagctac  1380
gcaggcgtcg gatga                                                   1395
```

<210> SEQ ID NO 6
<211> LENGTH: 1386
<212> TYPE: DNA
<213> ORGANISM: Unknown
<220> FEATURE:
<223> OTHER INFORMATION: Obtained from an environmental sample

<400> SEQUENCE: 6

```
atgaagaagt ttgtcgccct gttcataacc atgttttcg tagtgagcat ggcagtcgtt    60
gcacagccag ctagcgccgc aaagtattcc gagctcgaag aaggcggcgt tataatgcag   120
gccttctact gggacgtccc aggtggagga atctggtggg acaccatcag gagcaagata   180
ccggagtggt acgaggcggg aatatccgcc atttggattc cgccagccag caaggggatg   240
agcggcggtt actcgatggg ctacgatccc tacgatttct ttgacctcgg cgagtacaac   300
cagaagggaa ccatcgaaac gcgctttggc tctaaacagg agctcatcaa tatgataaac   360
acggcccatg cctacggcat aaaggtcata gcggacatcg tcataaacca ccgcgcaggc   420
ggagacctcg agtggaaccc gttcgttggg gactacacct ggacggactt ctcaaaggtg   480
gcctcgggca aatatactgc caactacctc gacttccacc caacgaggt caagtgctgt   540
```

```
gacgagggca catttggagg cttcccagac atagcccacg agaagagctg ggaccagcac    600
tggctctggg cgagcgatga gagctacgcc gcctacctaa ggagcatcgg cgttgatgcc    660
tggcgctttg actacgtgaa gggctacgga gcgtgggtcg tcaaggactg gctcaactgg    720
tggggcggct gggccgttgg cgagtactgg gacaccaacg ttgatgcact cctcaactgg    780
gcctactcga gcggcgccaa ggtcttcgac ttcccgctct actacaagat ggatgaggcc    840
tttgacaaca aaacattcc agcgctcgtc tctgcccttc agaacggcca gactgttgtc     900
tcccgcgacc cgttcaaggc cgtaacctttt gtagcaaacc acgacaccga tataatctgg    960
aacaagtacc ttgcttatgc tttcatcctc acctacgaag ccagcccgt catattctac     1020 cgcgactacg aggagtggct caacaaggac aggttgaaca acctcatatg gatacacgac    1080
cacctcgcag gtggaagcac gagcatagtc tactacgaca cgcgacgagat gatcttcgtg   1140 aggaacggct atggaagcaa gcctggcctt ataacttaca tcaacctcgg ctcgagcaag   1200
gttggaaggt gggtttatgt gccgaagttc gcgggcgcgt gcatccacga gtatactggt   1260
aacctcggag gctgggtaga caagtacgtc tactcaagcg gctgggtcta tctcgaagct   1320
ccagcttacg accctgccaa cgggcagtat ggctactccg tgtggagcta ttgcggtgtt   1380
gggtga                                                              1386
```

```
<210> SEQ ID NO 7
<211> LENGTH: 472
<212> TYPE: PRT
<213> ORGANISM: Unknown
<220> FEATURE:
<223> OTHER INFORMATION: Obtained from an environmental sample

<400> SEQUENCE: 7

Met Phe Leu Leu Ala Phe Leu Leu Thr Ala Ser Leu Phe Cys Pro Thr
 1               5                  10                  15

Gly Gln Pro Ala Lys Ala Ala Pro Phe Asn Gly Thr Met Met Gln
             20                  25                  30

Tyr Phe Glu Trp Tyr Leu Pro Asp Asp Gly Thr Leu Trp Thr Lys Val
         35                  40                  45

Ala Asn Glu Ala Asn Asn Leu Ser Ser Leu Gly Ile Thr Ala Leu Trp
     50                  55                  60

Leu Pro Pro Ala Tyr Lys Gly Thr Ser Arg Ser Asp Val Gly Tyr Gly
 65                  70                  75                  80

Val Tyr Asp Leu Tyr Asp Leu Gly Glu Phe Asn Gln Lys Gly Thr Val
                 85                  90                  95

Arg Thr Lys Tyr Gly Thr Lys Ala Gln Tyr Leu Gln Ala Ile Gln Ala
            100                 105                 110

Ala His Ala Ala Gly Met Gln Val Tyr Ala Asp Val Phe Asp His
        115                 120                 125

Lys Gly Gly Ala Asp Gly Thr Glu Trp Val Asp Ala Val Glu Val Asn
    130                 135                 140

Pro Ser Asp Arg Asn Gln Glu Ile Ser Gly Thr Tyr Gln Ile Gln Ala
145                 150                 155                 160

Trp Thr Lys Phe Asp Phe Pro Gly Arg Gly Asn Thr Tyr Ser Ser Phe
                165                 170                 175

Lys Trp Arg Trp Tyr His Phe Asp Gly Val Asp Trp Asp Glu Ser Arg
            180                 185                 190

Lys Leu Ser Arg Ile Tyr Lys Phe Arg Gly Ile Gly Lys Ala Trp Asp
        195                 200                 205
```

-continued

```
Trp Glu Val Asp Thr Glu Asn Gly Asn Tyr Asp Tyr Leu Met Tyr Ala
    210                 215                 220

Asp Leu Asp Met Asp His Pro Glu Val Val Thr Glu Leu Lys Asn Trp
225                 230                 235                 240

Gly Lys Trp Tyr Val Asn Thr Thr Asn Ile Asp Gly Phe Arg Leu Asp
                245                 250                 255

Ala Val Lys His Ile Lys Phe Ser Phe Phe Pro Asp Trp Leu Ser Tyr
            260                 265                 270

Val Arg Ser Gln Thr Gly Lys Pro Leu Phe Thr Val Gly Glu Tyr Trp
        275                 280                 285

Ser Tyr Asp Ile Asn Lys Leu His Asn Tyr Ile Thr Lys Thr Asp Gly
    290                 295                 300

Thr Met Ser Leu Phe Asp Ala Pro Leu His Asn Lys Phe Tyr Thr Ala
305                 310                 315                 320

Ser Lys Ser Gly Gly Ala Phe Asp Met Arg Thr Leu Met Thr Asn Thr
                325                 330                 335

Leu Met Lys Asp Gln Pro Thr Leu Ala Val Thr Phe Val Asp Asn His
            340                 345                 350

Asp Thr Glu Pro Gly Gln Ala Leu Gln Ser Trp Val Asp Pro Trp Phe
        355                 360                 365

Lys Pro Leu Ala Tyr Ala Phe Ile Leu Thr Arg Gln Glu Gly Tyr Pro
    370                 375                 380

Cys Val Phe Tyr Gly Asp Tyr Gly Ile Pro Gln Tyr Asn Ile Pro
385                 390                 395                 400

Ser Leu Lys Ser Lys Ile Asp Pro Leu Leu Ile Ala Arg Arg Asp Tyr
                405                 410                 415

Ala Tyr Gly Thr Gln His Asp Tyr Leu Asp His Ser Asp Ile Ile Gly
            420                 425                 430

Trp Thr Arg Glu Gly Val Thr Glu Lys Pro Gly Ser Gly Leu Ala Ala
        435                 440                 445

Leu Ile Thr Asp Gly Pro Gly Gly Ser Lys Trp Met Tyr Cys Trp Gln
    450                 455                 460

Thr Thr Arg Trp Lys Ser Val Leu
465                 470
```

```
<210> SEQ ID NO 8
<211> LENGTH: 512
<212> TYPE: PRT
<213> ORGANISM: Unknown
<220> FEATURE:
<223> OTHER INFORMATION: Obtained from an environmental sample

<400> SEQUENCE: 8
```

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95
```

-continued

```
His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Arg Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ala Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
    370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
    450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510
```

```
<210> SEQ ID NO 9
<211> LENGTH: 464
<212> TYPE: PRT
<213> ORGANISM: Unknown
<220> FEATURE:
<223> OTHER INFORMATION: Obtained from an environmental sample

<400> SEQUENCE: 9
```

Val Val His Met Lys Leu Lys Tyr Leu Ala Leu Val Leu Leu Ala Val
 1               5                  10                  15

Ala Ser Ile Gly Leu Leu Ser Thr Pro Val Gly Ala Ala Lys Tyr Ser
            20                  25                  30

Glu Leu Glu Glu Gly Gly Val Ile Met Gln Ala Phe Tyr Trp Asp Val
        35                  40                  45

Pro Gly Gly Gly Ile Trp Trp Asp Thr Ile Arg Gln Lys Ile Pro Glu
    50                  55                  60

Trp Tyr Asp Ala Gly Ile Ser Ala Ile Trp Ile Pro Pro Ala Ser Lys
65                  70                  75                  80

Gly Met Gly Gly Gly Tyr Ser Met Gly Tyr Asp Pro Tyr Asp Phe Phe
                85                  90                  95

Asp Leu Gly Glu Tyr Tyr Gln Lys Gly Thr Val Glu Thr Arg Phe Gly
            100                 105                 110

Ser Lys Glu Glu Leu Val Asn Met Ile Asn Thr Ala His Ser Tyr Gly
        115                 120                 125

Ile Lys Val Ile Ala Asp Ile Val Ile Asn His Arg Ala Gly Gly Asp
130                 135                 140

Leu Glu Trp Asn Pro Phe Val Asn Asn Tyr Thr Trp Thr Asp Phe Ser
145                 150                 155                 160

Lys Val Ala Ser Gly Lys Tyr Thr Ala Asn Tyr Leu Asp Phe His Pro
                165                 170                 175

Asn Glu Val Lys Cys Cys Asp Glu Gly Thr Phe Gly Asp Phe Pro Asp
            180                 185                 190

Ile Ala His Glu Lys Ser Trp Asp Gln Tyr Trp Leu Trp Ala Ser Asn
        195                 200                 205

Glu Ser Tyr Ala Ala Tyr Leu Arg Ser Ile Gly Ile Asp Ala Trp Arg
    210                 215                 220

Phe Asp Tyr Val Lys Gly Tyr Gly Ala Trp Val Val Asn Asp Trp Leu
225                 230                 235                 240

Ser Trp Trp Gly Gly Trp Ala Val Gly Glu Tyr Trp Asp Thr Asn Val
                245                 250                 255

Asp Ala Leu Leu Asn Trp Ala Tyr Asp Ser Gly Ala Lys Val Phe Asp
            260                 265                 270

Phe Pro Leu Tyr Tyr Lys Met Asp Glu Ala Phe Asp Asn Thr Asn Ile
        275                 280                 285

Pro Ala Leu Val Tyr Ala Leu Gln Asn Gly Gly Thr Val Val Ser Arg
    290                 295                 300

Asp Pro Phe Lys Ala Val Thr Phe Val Ala Asn His Asp Thr Asp Ile
305                 310                 315                 320

Ile Trp Asn Lys Tyr Pro Ala Tyr Ala Phe Ile Leu Thr Tyr Glu Gly
                325                 330                 335

Gln Pro Val Ile Phe Tyr Arg Asp Tyr Glu Glu Trp Leu Asn Lys Asp
            340                 345                 350

Lys Leu Asn Asn Leu Ile Trp Ile His Glu His Leu Ala Gly Gly Ser
        355                 360                 365

Thr Lys Ile Leu Tyr Tyr Asp Asn Asp Glu Leu Ile Phe Met Arg Glu

```
                    370                 375                 380
Gly Tyr Gly Ser Lys Pro Gly Leu Ile Thr Tyr Ile Asn Leu Gly Asn
385                 390                 395                 400

Asp Trp Ala Glu Arg Trp Val Asn Val Gly Ser Lys Phe Ala Gly Tyr
                405                 410                 415

Thr Ile His Glu Tyr Thr Gly Asn Leu Gly Gly Trp Val Asp Arg Trp
                420                 425                 430

Val Gln Tyr Asp Gly Trp Val Lys Leu Thr Ala Pro His Asp Pro
                435                 440                 445

Ala Asn Gly Tyr Gly Tyr Ser Val Trp Ser Tyr Ala Gly Val Gly
    450                 455                 460

<210> SEQ ID NO 10
<211> LENGTH: 461
<212> TYPE: PRT
<213> ORGANISM: Unknown
<220> FEATURE:
<223> OTHER INFORMATION: Obtained from an environmental sample

<400> SEQUENCE: 10

Met Lys Lys Phe Val Ala Leu Phe Ile Thr Met Phe Phe Val Val Ser
 1               5                  10                  15

Met Ala Val Val Ala Gln Pro Ala Ser Ala Lys Tyr Ser Glu Leu
             20                  25                  30

Glu Glu Gly Gly Val Ile Met Gln Ala Phe Tyr Trp Asp Val Pro Gly
             35                  40                  45

Gly Gly Ile Trp Trp Asp Thr Ile Arg Ser Lys Ile Pro Glu Trp Tyr
         50                  55                  60

Glu Ala Gly Ile Ser Ala Ile Trp Ile Pro Pro Ala Ser Lys Gly Met
65                  70                  75                  80

Ser Gly Gly Tyr Ser Met Gly Tyr Asp Pro Tyr Asp Phe Phe Asp Leu
                 85                  90                  95

Gly Glu Tyr Asn Gln Lys Gly Thr Ile Glu Thr Arg Phe Gly Ser Lys
            100                 105                 110

Gln Glu Leu Ile Asn Met Ile Asn Thr Ala His Ala Tyr Gly Ile Lys
        115                 120                 125

Val Ile Ala Asp Ile Val Ile Asn His Arg Ala Gly Gly Asp Leu Glu
    130                 135                 140

Trp Asn Pro Phe Val Gly Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln His Trp Leu Trp Ala Ser Asp Glu Ser
        195                 200                 205

Tyr Ala Ala Tyr Leu Arg Ser Ile Gly Val Asp Ala Trp Arg Phe Asp
    210                 215                 220

Tyr Val Lys Gly Tyr Gly Ala Trp Val Val Lys Asp Trp Leu Asn Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Gly Ala Lys Val Phe Asp Phe Pro
            260                 265                 270

Leu Tyr Tyr Lys Met Asp Glu Ala Phe Asp Asn Lys Asn Ile Pro Ala
```

```
                275                 280                 285
Leu Val Ser Ala Leu Gln Asn Gly Gln Thr Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Leu Ala Tyr Ala Phe Ile Leu Thr Tyr Glu Gly Gln Pro
                325                 330                 335

Val Ile Phe Tyr Arg Asp Tyr Glu Glu Trp Leu Asn Lys Asp Arg Leu
                340                 345                 350

Asn Asn Leu Ile Trp Ile His Asp His Leu Ala Gly Gly Ser Thr Ser
                355                 360                 365

Ile Val Tyr Tyr Asp Ser Asp Glu Met Ile Phe Val Arg Asn Gly Tyr
            370                 375                 380

Gly Ser Lys Pro Gly Leu Ile Thr Tyr Ile Asn Leu Gly Ser Ser Lys
385                 390                 395                 400

Val Gly Arg Trp Val Tyr Val Pro Lys Phe Ala Gly Ala Cys Ile His
                405                 410                 415

Glu Tyr Thr Gly Asn Leu Gly Gly Trp Val Asp Lys Tyr Val Tyr Ser
            420                 425                 430

Ser Gly Trp Val Tyr Leu Glu Ala Pro Ala Tyr Asp Pro Ala Asn Gly
        435                 440                 445

Gln Tyr Gly Tyr Ser Val Trp Ser Tyr Cys Gly Val Gly
    450                 455                 460

<210> SEQ ID NO 11
<211> LENGTH: 47
<212> TYPE: DNA
<213> ORGANISM: Artificial Sequence
<220> FEATURE:
<223> OTHER INFORMATION: Primer

<400> SEQUENCE: 11
gaacactagt aggaggtaac ttatggcaaa gtattccgag ctcgaag                47

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
gaacggtctc attccgccag ccagcaaggg gatgagcgg                         39

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gaaccgtctc aaaacacggc ccatgcctac ggc                               33

<210> SEQ ID NO 14
<211> LENGTH: 38
<212> TYPE: DNA
<213> ORGANISM: Artificial Sequence
<220> FEATURE:
<223> OTHER INFORMATION: Primer
```

```
<400> SEQUENCE: 14
gaacgtctca cctcgacttc caccccaacg aggtcaag                              38

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gaacgtctca ggcgctttga ctacgtgaag ggc                                   33

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
gaacggtctc aacaagatgg atgaggcctt tg                                    32

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
gaaccgtctc acgatataat ctggaacaag taccttgc                              38

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
gaaccgtctc agaagcacga gcatagttta ctacg                                 35

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
gaaccgtctc aaaggtgggt ttatgtgccg                                       30

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
gaacgtctca ggaatccaaa tggcggatat tcccgc                                36

<210> SEQ ID NO 21
<211> LENGTH: 33
```

```
<212> TYPE: DNA
<213> ORGANISM: Artificial Sequence
<220> FEATURE:
<223> OTHER INFORMATION: Primer

<400> SEQUENCE: 21
gaacggtctc agtttatcat attgatgagc tcc                            33

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
gaaccgtctc agaggtagtt ggcagtatat ttg                            33

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
gaacgtctca cgccaggcat caacgccgat g                              31

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
gaacgtctca ttgtagtaga gcgggaagtc                                30

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
gaacggtctc aatcggtgtc gtggtttgct ac                             32

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gaaccgtctc acttccacct gcgaggtggt c                              31

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
```

```
gaaccgtctc accttccaac cttgctcgag c                                    31
```

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28

```
tcgagactga ctctcaccca acaccgcaat agc                                  33
```

<210> SEQ ID NO 29
<211> LENGTH: 50
<212> TYPE: DNA
<213> ORGANISM: Artificial Sequence
<220> FEATURE:
<223> OTHER INFORMATION: Primer

<400> SEQUENCE: 29

```
gaacactagt aggaggtaac ttatggccaa gtacctggag ctcgaagagg                50
```

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30

```
gaacggtctc attccccgg cgagcaaggg c                                     31
```

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31

```
gaaccgtctc aaaacaccgc ccacgcctac gg                                   32
```

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32

```
gaacgtctca cctcgacttc caccccaac                                       29
```

<210> SEQ ID NO 33
<211> LENGTH: 31
<212> TYPE: DNA
<213> ORGANISM: Artificial Sequence
<220> FEATURE:
<223> OTHER INFORMATION: Primer

<400> SEQUENCE: 33

```
gaacgtctca ggcgcttcga ctacgtcaag g                                    31
```

<210> SEQ ID NO 34
<211> LENGTH: 34
<212> TYPE: DNA
<213> ORGANISM: Artificial Sequence

```
<220> FEATURE:
<223> OTHER INFORMATION: Primer

<400> SEQUENCE: 34
gaacggtctc aacaagatgg acgcggcctt tgac                            34

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
gaaccgtctc acgatataat ttggaacaag taccc                           35

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
gaaccgtctc agaagcaccg acatagtcta c                               31

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
gaaccgtctc aaaggtgggt ctacgttccg                                 30

<210> SEQ ID NO 38
<211> LENGTH: 36
<212> TYPE: DNA
<213> ORGANISM: Artificial Sequence
<220> FEATURE:
<223> OTHER INFORMATION: Primer

<400> SEQUENCE: 38
gaacgtctca ggaatccata ttgcggagat tccggc                          36

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
gaacggtctc agtttatcat gttcacgagc tc                              32

<210> SEQ ID NO 40
<211> LENGTH: 33
<212> TYPE: DNA
<213> ORGANISM: Artificial Sequence
<220> FEATURE:
<223> OTHER INFORMATION: Primer

<400> SEQUENCE: 40
gaaccgtctc agaggtagtt ggccgtgtac ttg                             33
```

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
gaacgtctca gccatgcgtc aacgccgatg                                    30

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
gaacgtctca ttgtagtaga gcgggaagtc g                                  31

<210> SEQ ID NO 43
<211> LENGTH: 33
<212> TYPE: DNA
<213> ORGANISM: Artificial Sequence
<220> FEATURE:
<223> OTHER INFORMATION: Primer

<400> SEQUENCE: 43
gaacggtctc aatcggtgtc gtggtttgca acg                                33

<210> SEQ ID NO 44
<211> LENGTH: 34
<212> TYPE: DNA
<213> ORGANISM: Artificial Sequence
<220> FEATURE:
<223> OTHER INFORMATION: Primer

<400> SEQUENCE: 44
gaaccgtctc acttccaccg gcgaggtggt cgtg                               34

<210> SEQ ID NO 45
<211> LENGTH: 32
<212> TYPE: DNA
<213> ORGANISM: Artificial Sequence
<220> FEATURE:
<223> OTHER INFORMATION: Primer

<400> SEQUENCE: 45
gaaccgtctc accttccggc cttgctcgag cc                                 32

<210> SEQ ID NO 46
<211> LENGTH: 35
<212> TYPE: DNA
<213> ORGANISM: Artificial Sequence
<220> FEATURE:
<223> OTHER INFORMATION: Primer

<400> SEQUENCE: 46
tcgagactga ctctcagccc accccgcagt agctc                              35

<210> SEQ ID NO 47
<211> LENGTH: 50
<212> TYPE: DNA
<213> ORGANISM: Artificial Sequence
<220> FEATURE:
<223> OTHER INFORMATION: Primer

```
<400> SEQUENCE: 47
gaacactagt aggaggtaac ttatggccaa gtactccgag ctggaagagg           50

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
gaacggtctc attcctcccg cgagcaaggg                                30

<210> SEQ ID NO 49
<211> LENGTH: 31
<212> TYPE: DNA
<213> ORGANISM: Artificial Sequence
<220> FEATURE:
<223> OTHER INFORMATION: Primer

<400> SEQUENCE: 49
gaaccgtctc aaaacaccgc ccacgcctat g                              31

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
gaacgtctca cctcgacttc cacccgaacg agc                            33

<210> SEQ ID NO 51
<211> LENGTH: 31
<212> TYPE: DNA
<213> ORGANISM: Artificial Sequence
<220> FEATURE:
<223> OTHER INFORMATION: Primer

<400> SEQUENCE: 51
gaacgtctca ggcgcttcga ctacgtcaag g                              31

<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52
gaacggtctc aacaagatgg acgaggcctt cg                             32

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
gaaccgtctc acgatataat ctggaacaag                                30

<210> SEQ ID NO 54
```

```
<211> LENGTH: 35
<212> TYPE: DNA
<213> ORGANISM: Artificial Sequence
<220> FEATURE:
<223> OTHER INFORMATION: Primer

<400> SEQUENCE: 54
gaaccgtctc agaagcactg acatcgttta ctacg                        35

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
gaaccgtctc aaaggtgggt ttacgttccg                              30

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
gaacgtctca ggaatccata tcgccgaaat                              30

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
gaacggtctc agtttatcat gtttatgagc                              30

<210> SEQ ID NO 58
<211> LENGTH: 34
<212> TYPE: DNA
<213> ORGANISM: Artificial Sequence
<220> FEATURE:
<223> OTHER INFORMATION: Primer

<400> SEQUENCE: 58
gaaccgtctc agaggtagtt ggccgtgtat ttac                         34

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
gaacgtctca cgccaggcat cgatgccgat                              30

<210> SEQ ID NO 60
<211> LENGTH: 34
<212> TYPE: DNA
<213> ORGANISM: Artificial Sequence
<220> FEATURE:
<223> OTHER INFORMATION: Primer

<400> SEQUENCE: 60
```

```
gaacgtctca ttgtagtaga gggcgaagtc aaag                                34
```

<210> SEQ ID NO 61
<211> LENGTH: 36
<212> TYPE: DNA
<213> ORGANISM: Artificial Sequence
<220> FEATURE:
<223> OTHER INFORMATION: Primer

<400> SEQUENCE: 61

```
gaacggtctc aatcggtatc gtggttggct acaaac                              36
```

<210> SEQ ID NO 62
<211> LENGTH: 34
<212> TYPE: DNA
<213> ORGANISM: Artificial Sequence
<220> FEATURE:
<223> OTHER INFORMATION: Primer

<400> SEQUENCE: 62

```
gaaccgtctc acttcctccg gcgaggttgt catg                                34
```

<210> SEQ ID NO 63
<211> LENGTH: 32
<212> TYPE: DNA
<213> ORGANISM: Artificial Sequence
<220> FEATURE:
<223> OTHER INFORMATION: Primer

<400> SEQUENCE: 63

```
gaaccgtctc accttccggc tttgcttgag gc                                  32
```

<210> SEQ ID NO 64
<211> LENGTH: 36
<212> TYPE: DNA
<213> ORGANISM: Artificial Sequence
<220> FEATURE:
<223> OTHER INFORMATION: Primer

<400> SEQUENCE: 64

```
tcgagactga ctctcaccca acaccgcagt agctcc                              36
```

<210> SEQ ID NO 65
<211> LENGTH: 38
<212> TYPE: DNA
<213> ORGANISM: Artificial Sequence
<220> FEATURE:
<223> OTHER INFORMATION: Primer

<400> SEQUENCE: 65

```
cacacagcag caaccaacct cgagactgac tctcascc                            38
```

<210> SEQ ID NO 66
<211> LENGTH: 1299
<212> TYPE: DNA
<213> ORGANISM: Unknown
<220> FEATURE:
<223> OTHER INFORMATION: Obtained from an environmental sample

<400> SEQUENCE: 66

```
atggctctgg aagagggcgg gctcataatg caggccttct actgggacgt ccccatggga    60
ggaatctggt gggacacgat agcccagaag atacccgact gggcaagcgc cgggatttcg   120
gcgatatgga tccctcccgc gagcaagggt atgagcggcg gctattcgat gggctacgac   180
```

```
ccctacgatt attttgacct cggtgagtac taccagaagg gaacggtgga aacgaggttc      240
ggctcaaagc aggagctcat aaacatgata aacaccgccc acgcctatgg catgaaggta      300
atagccgata tagtcatcaa ccaccgcgcc ggcggtgacc tggagtggaa ccccttcgtg      360
aacgactata cctggaccga cttctcaaag gtcgcgtcgg gtaaatacac ggccaactac      420
ctcgacttcc acccgaacga gctccatgcg ggcgattccg gaacatttgg aggctatccc      480
gacatatgcc acgacaagag ctgggaccag tactggctct gggccagcca ggagagctac      540
gcggcatatc tcaggagcat cggcatcgat gcctggcgct tcgactacgt caagggctat      600
gctcccctgg tcgtcaagga ctggctgaac tggtggggag gctgggcggt tggagagtac      660
tgggacacca acgtcgacgc tgttctcaac tgggcatact cgagcggtgc caaggtcttt      720
gacttcgccc tctactacaa gatggacgag gccttcgata caacaacat tcccgccctg      780
gtggacgccc tcagatacgg tcagacagtg gtcagccgcg acccgttcaa ggctgtgacg      840
tttgtagcca accacgatac cgacataatc tggaacaagt atccagccta cgcgttcatc      900
ctcacctacg agggccagcc gacaatattc taccgcgact acgaggagtg gctcaacaag      960
gataagctca agaacctcat ctggatacat gacaacctcg ccggagggag cactgacatc      1020
gtttactacg acaacgacga gctgatattc gtgagaaacg gctacggaag caagccggga      1080
ctgataacat acatcaacct cgcctcaagc aaagccggaa ggtgggttta cgttccgaag      1140
ttcgcaggct cgtgcataca cgagtacacc ggcaatctcg gcggctgggt ggacaagtgg      1200
gtggactcaa gcggctgggt ctacctcgag gctcctgccc acgacccggc caacggccag      1260
tacggctact ccgtctggag ctactgcggt gttgggtga                            1299
```

<210> SEQ ID NO 67
<211> LENGTH: 432
<212> TYPE: PRT
<213> ORGANISM: Unknown
<220> FEATURE:
<223> OTHER INFORMATION: Obtained from an environmental sample

<400> SEQUENCE: 67

```
Met Ala Leu Glu Glu Gly Gly Leu Ile Met Gln Ala Phe Tyr Trp Asp
 1               5                  10                  15

Val Pro Met Gly Gly Ile Trp Trp Asp Thr Ile Ala Gln Lys Ile Pro
             20                  25                  30

Asp Trp Ala Ser Ala Gly Ile Ser Ala Ile Trp Ile Pro Pro Ala Ser
         35                  40                  45

Lys Gly Met Ser Gly Gly Tyr Ser Met Gly Tyr Asp Pro Tyr Asp Tyr
     50                  55                  60

Phe Asp Leu Gly Glu Tyr Tyr Gln Lys Gly Thr Val Glu Thr Arg Phe
 65                  70                  75                  80

Gly Ser Lys Gln Glu Leu Ile Asn Met Ile Asn Thr Ala His Ala Tyr
                 85                  90                  95

Gly Met Lys Val Ile Ala Asp Ile Val Ile Asn His Arg Ala Gly Gly
            100                 105                 110

Asp Leu Glu Trp Asn Pro Phe Val Asn Asp Tyr Thr Trp Thr Asp Phe
        115                 120                 125

Ser Lys Val Ala Ser Gly Lys Tyr Thr Ala Asn Tyr Leu Asp Phe His
    130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln Tyr Trp Leu Trp Ala Ser
```

```
                    165                 170                 175
Gln Glu Ser Tyr Ala Ala Tyr Leu Arg Ser Ile Gly Ile Asp Ala Trp
            180                 185                 190
Arg Phe Asp Tyr Val Lys Gly Tyr Ala Pro Trp Val Lys Asp Trp
        195                 200                 205
Leu Asn Trp Trp Gly Gly Trp Ala Val Gly Glu Tyr Trp Asp Thr Asn
    210                 215                 220
Val Asp Ala Val Leu Asn Trp Ala Tyr Ser Ser Gly Ala Lys Val Phe
225                 230                 235                 240
Asp Phe Ala Leu Tyr Tyr Lys Met Asp Glu Ala Phe Asp Asn Asn Asn
                245                 250                 255
Ile Pro Ala Leu Val Asp Ala Leu Arg Tyr Gly Gln Thr Val Val Ser
            260                 265                 270
Arg Asp Pro Phe Lys Ala Val Thr Phe Val Ala Asn His Asp Thr Asp
        275                 280                 285
Ile Ile Trp Asn Lys Tyr Pro Ala Tyr Ala Phe Ile Leu Thr Tyr Glu
    290                 295                 300
Gly Gln Pro Thr Ile Phe Tyr Arg Asp Tyr Glu Glu Trp Leu Asn Lys
305                 310                 315                 320
Asp Lys Leu Lys Asn Leu Ile Trp Ile His Asp Asn Leu Ala Gly Gly
                325                 330                 335
Ser Thr Asp Ile Val Tyr Tyr Asp Asn Asp Glu Leu Ile Phe Val Arg
            340                 345                 350
Asn Gly Tyr Gly Ser Lys Pro Gly Leu Ile Thr Tyr Ile Asn Leu Ala
        355                 360                 365
Ser Ser Lys Ala Gly Arg Trp Val Tyr Val Pro Lys Phe Ala Gly Ser
    370                 375                 380
Cys Ile His Glu Tyr Thr Gly Asn Leu Gly Gly Trp Val Asp Lys Trp
385                 390                 395                 400
Val Asp Ser Ser Gly Trp Val Tyr Leu Glu Ala Pro Ala His Asp Pro
                405                 410                 415
Ala Asn Gly Gln Tyr Gly Tyr Ser Val Trp Ser Tyr Cys Gly Val Gly
            420                 425                 430
```

<210> SEQ ID NO 68
<211> LENGTH: 1386
<212> TYPE: DNA
<213> ORGANISM: Unknown
<220> FEATURE:
<223> OTHER INFORMATION: Obtained from an environmental sample

<400> SEQUENCE: 68

```
atgaagcctg cgaaactcct cgtctttgtg ctcgtagtct ctatcctcgc ggggctctac      60
gcccagcccg cggggcggc caagtacctg gagctcgaag agggcggcgt cataatgcag     120
gcgttctact gggacgtgcc ttcaggagga atatggtggg acacaatacg gcagaagata     180
ccggagtggt acgatgccgg aatctccgca atatggattc ccccggcgag caagggcatg     240
ggcggcgcct attcgatggg ctacgacccc tacgacttct ttgacctcgg tgagtacgac     300
cagaagggaa cggtagagac gcgctttggc tccaagcagg agctcgtgaa catgataaac     360
accgcccacg cctacggcat caaggtcatc gcagacatag taatcaacca ccgcgccgga     420
ggagaccttg agtggaaccc cttcgtcaat gactacacct ggacggactt ctcgaaggtc     480
gcttccggca agtacacggc caactacctc gacttccacc caacgaggt caagtgctgc     540 gacgagggca cctttggagg gttcccggac atagcccacg agaagagctg ggaccagtac     600
```

-continued

```
tggctctggg cgagcaacga gagctacgcc gcctacctca ggagcatcgg cgttgacgca      660
tggcgcttcg actacgtcaa gggctacgga gcgtgggtcg tcaaggactg gctggactgg      720
tggggaggct gggccgtcgg ggagtactgg gacacaaacg ttgatgcact gctcaactgg      780
gcctactcga gcgatgcaaa agtcttcgac ttcccgctct actacaagat ggacgcggcc      840
tttgacaaca gaacattcc cgcactcgtc gaggccctca gaacggggg cacagtcgtc        900 agccgcgacc cgtttaaggc cgtaaccttc gttgcaaacc acgacacgga cataatttgg      960
aacaagtacc cggcctacgc cttcatcctc acctacgagg ccagccgac gatattctac      1020 cgcgactacg aggagtggct caacaaggac aggctcaaga acctcatctg gatacacgac     1080
cacctcgccg gtggaagcac cgacatagtc tactacgata cgatgaact catcttcgtc      1140 aggaacggct acggggacaa gccggggctt ataacctaca tcaacctagg ctcgagcaag     1200
gccgggaggt gggtctacgt tccgaagttc gcgggagcgt gcatccacga gtacaccggc     1260
aacctcggcg gctgggtgga caagtgggtg gactcaagcg ggtgggtgta cctcgaggcc     1320
cctgcccacg acccggccaa cggctattac ggctactccg tctggagcta ctgcggggtg     1380
ggctga                                                                1386
```

<210> SEQ ID NO 69
<211> LENGTH: 461
<212> TYPE: PRT
<213> ORGANISM: Unknown
<220> FEATURE:
<223> OTHER INFORMATION: Obtained from an environmental sample

<400> SEQUENCE: 69

```
Met Lys Pro Ala Lys Leu Leu Val Phe Val Leu Val Ser Ile Leu
 1               5                  10                  15

Ala Gly Leu Tyr Ala Gln Pro Ala Gly Ala Lys Tyr Leu Glu Leu
                20                  25                  30

Glu Glu Gly Gly Val Ile Met Gln Ala Phe Tyr Trp Asp Val Pro Ser
            35                  40                  45

Gly Gly Ile Trp Trp Asp Thr Ile Arg Gln Lys Ile Pro Glu Trp Tyr
        50                  55                  60

Asp Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
            100                 105                 110

Gln Glu Leu Val Asn Met Ile Asn Thr Ala His Ala Tyr Gly Ile Lys
        115                 120                 125

Val Ile Ala Asp Ile Val Ile Asn His Arg Ala Gly Gly Asp Leu Glu
    130                 135                 140

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln Tyr Trp Leu Trp Ala Ser Asn Glu Ser
        195                 200                 205

Tyr Ala Ala Tyr Leu Arg Ser Ile Gly Val Asp Ala Trp Arg Phe Asp
```

-continued

```
                    210                     215                     220
Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Asp Ala Lys Val Phe Asp Phe Pro
                260                 265                 270

Leu Tyr Tyr Lys Met Asp Ala Ala Phe Asp Asn Lys Asn Ile Pro Ala
        275                 280                 285

Leu Val Glu Ala Leu Lys Asn Gly Gly Thr Val Val Ser Arg Asp Pro
        290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
            355                 360                 365

Ile Val Tyr Tyr Asp Asn Asp Glu Leu Ile Phe Val Arg Asn Gly Tyr
        370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
                405                 410                 415

Glu Tyr Thr Gly Asn Leu Gly Gly Trp Val Asp Lys Trp Val Asp Ser
                420                 425                 430

Ser Gly Trp Val Tyr Leu Glu Ala Pro Ala His Asp Pro Ala Asn Gly
            435                 440                 445

Tyr Tyr Gly Tyr Ser Val Trp Ser Tyr Cys Gly Val Gly
450                 455                 460
```